(12) United States Patent
Maine et al.

(10) Patent No.: US 6,221,619 B1
(45) Date of Patent: Apr. 24, 2001

(54) **METHOD OF USING P35 ANTIGEN OF *TOXOPLASMA GONDII* IN DISTINGUISHING ACUTE FROM CHRONIC TOXOPLASMOSIS**

(75) Inventors: Gregory T. Maine, Gurnee; Jeffrey C. Hunt, Mundelein, both of IL (US); Susan Brojanac, Brookfield, WI (US); Michael Jyh-Tsing Sheu, Gurnee, IL (US); Linda E. Chovan, Kenosha, WI (US); Joan D. Tyner, Beach Park; Lawrence V. Howard, Libertyville, both of IL (US); Stephen F. Parmley, San Jose, CA (US); Jack S. Remington, Menlo Park, CA (US); Fausto Araujo, Palo Alto, CA (US); Yashuhiro Suzuki, Menlo Park, CA (US); Shuli Li, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/303,064

(22) Filed: Apr. 30, 1999

Related U.S. Application Data

(63) Continuation-in-part of application No. 09/086,503, filed on May 28, 1998.

(51) Int. Cl.[7] ............................. G01N 33/53; C12N 15/09
(52) U.S. Cl. ..................... 435/7.22; 435/7.92; 435/7.1; 435/69.3
(58) Field of Search .................................. 435/7.22, 7.1, 435/7.92, 69.3, 810, 967, 975; 436/808; 530/806, 822, 820, 861, 300, 350

(56) References Cited

FOREIGN PATENT DOCUMENTS

| 0 472 207 | 2/1992 | (EP) . |
| 0 782 860 | 7/1997 | (EP) . |
| WO 93/08208 | 4/1993 | (WO) . |

OTHER PUBLICATIONS

Huskinson et al. J. Clin. Microbiol. 27: 2031–2038, 1989.*
Gutierrez et al. Clin. Microbiol. Infect. 3: 658–662, Dec. 1997.*
Fischer et al: "GRA7, an excretory 29 kDa Toxoplasma gondii dense granule antigen released by infected host cells" Molecular and Biochemical Parasitology, vol. 91, Mar. 15, 1998, pp. 251–262, XP002127971.
Jacobs et al.: "Identification and heterologous expression of a new dense granule protein (GRA7) from Toxoplasma gondii" Molecular and Biochemical Parasitology, vol. 91, Mar. 15, 1998, pp. 237–249, X 002127972.
Kohler et al.: "Continuous cultures of fused cells secreting antibody of predefined specificity" Nature, GB Macmillan Journals Ltd. London, vol. 256, pp. 495–497, XP002044294 ISSN: 0028–0836.
Sabin, A.B. and Feldman, H.A. (1948) Science 108, 660–663.
Naot, Y. and Remington, J.S. (1980) J. Infect. Dis. 142, 757–766.
Prince et al. (1990) Mol. Biochem, Parasitol 43, 97–106.
Cesbron–Delauw et al. (1989) Proc. Natl. Acad. Sci. 86, 7537–7541.
Johnson et al. (1991) Gene 99, 127–132.
Prince et al. (1989) Mol. Biochem. Parasitol. 34, 3–14.
Burg et al. (1988) J. Immunol. 141, 3584–3591.
Mevelec et al. (1992) Mol. Biochem. Parasitol 56, 227–238.
Saavedra et al. (1991) J. Immunol. 147, 1975–1982.
Walton, B.C. et al. (1966) Am. J. Trop. Med. Hyg. 15, 149–152.
Liesenfeld et al., *Journal of Clinical Microbiology* 35:174–78 (1997).
Wilson et al., *Journal of Clinical Microbiology* 35:3112–15 (1997).
Wong et al., *Clinical Infectious Diseases* 18:853–62 (1994).
Potasman et al., Journal of Infectious Diseases 153:650–57 (1986).
Potasman et al., *Journal of Clinical Microbiology* 25:1926–31 (1987).

* cited by examiner

Primary Examiner—Lynette R. F. Smith
Assistant Examiner—S. Devi
(74) Attorney, Agent, or Firm—Cheryl L. Becker

(57) ABSTRACT

The present invention relates to combinations or mixtures of antigens which may be used in the detection of IgM and/or IgG antibodies to *Toxoplasma gondii* as well as to the P35 antigen which may be used to distinguish acute from chronic toxoplasmosis. Furthermore, the present invention also relates to methods of using these combinations of antigens, antibodies raised against these combinations of antigens or against the novel P29 antigen thereof, as well as kits and vaccines containing the antigens present in the combinations.

3 Claims, 61 Drawing Sheets pGM613

```
          10          20          30          40
  1234567890  1234567890  1234567890  1234567890
  GAATTCGGCA  CGAGGCGAAC  TGGGGCAAAG  CCGCCGCCAC        40
   AsnSerAla  ArgGlyGluL  euGlyGlnSe  rArgArgHis

CAGTTCGCTA  CCGCGGCCAC  CGCGTCAGAT  GACGAACTGA        80
   GlnPheAlaT  hrAlaAlaTh  rAlaSerAsp  AspGluLeuM

TGAGTCGAAT  CCGAAATTCT  GACTTTTTCG  ATGGTCAAGC       120
   etSerArgIl  eArgAsnSer  AspPhePheA  spGlyGlnAl

ACCCGTTGAC  AGTCTCAGAC  CGACGAACGC  CGGTGTCGAC       160
   aProValAsp  SerLeuArgP  roThrAsnAl  aGlyValAsp

TCGAAAGGGA  CCGACGATCA  CCTCACCACC  AGCATGGATA       200
   SerLysGlyT  hrAspAspHi  sLeuThrThr  SerMetAspL

AGGCATCTGT  AGAGAGTCAG  CTTCCGAGAA  GAGAGCCATT       240
   ysAlaSerVa  lGluSerGln  LeuProArgA  rgGluProLe

GGAGACGGAG  CCAGATGAAC  AAGAAGAAGT  TCATTTCAGG       280
   uGluThrGlu  ProAspGluG  lnGluGluVa  lHisPheArg

AAGCGAGGCG  TCCGTTCCGA  CGCTGAAGTG  ACTGACGACA       320
   LysArgGlyV  alArgSerAs  pAlaGluVal  ThrAspAspA

ACATCTACGA  GGAGCACACT  GATCGTAAGG  TGGTTCCGAG       360
   snIleTyrGl  uGluHisThr  AspArgLysV  alValProAr

GAAGTCGGAG  GGCAAGCGAA  GCTTCAAAGA  CTTGCTGAAG       400
   gLysSerGlu  GlyLysArgS  erPheLysAs  pLeuLeuLys

AAGCTCGCGC  TGCCGGCTGT  TGGTATGGGT  GCATCGTATT       440
   LysLeuAlaL  euProAlaVa  lGlyMetGly  AlaSerTyrP

TTGCCGCTGA  TAGACTTGTG  CCGGAACTAA  CAGAGGAGCA       480
   heAlaAlaAs  pArgLeuVal  ProGluLeuT  hrGluGluGl

ACAGAGAGGC  GACGAACCCC  TAACCACCGG  CCAGAATGTG       520
   nGlnArgGly  AspGluProL  euThrThrGl  yGlnAsnVal
```

FIG.1A pGM613

|  | 10 | 20 | 30 | 40 |  |
|---|---|---|---|---|---|
|  | 1234567890 | 1234567890 | 1234567890 | 1234567890 |  |
|  | GGCACTGTGT | TAGGCTTCGC | AGCGCTTGCT | GCTGCCGCAG | 560 |
|  | GlyThrValL | euGlyPheAl | aAlaLeuAla | AlaAlaAlaA | |
|  | CGTTCCTTGG | CATGGGTCTC | ACGAGGACGT | ACCGACATTT | 600 |
|  | laPheLeuGl | yMetGlyLeu | ThrArgThrT | yrArgHisPh | |
|  | TTCCCCACGC | AAAAACAGAT | CACGGCAGCC | TGCACTCGAG | 640 |
|  | eSerProArg | LysAsnArgS | erArgGlnPr | oAlaLeuGlu | |
|  | CAAGAGGTGC | CTGAATCAGG | CGAAGATGGG | GAGGATGCCC | 680 |
|  | GlnGluValP | roGluSerGl | yGluAspGly | GluAspAlaA | |
|  | GCCAGTAGGA | TATGGGGGCT | AATAAAAGTG | AGTAGGAGCT | 720 |
|  | rgGln | | | | |
|  | CGAGGACAGT | GTCCCGAACG | CGCCTGAGAG | GCAGACAGAC | 760 |
|  | ACAGAAGAGT | GAAGAAAAAC | AACATGGTAT | TACGTGCGGT | 800 |
|  | GAGTGTTTGC | TGTCACGTGT | TTTTTGCGCC | ACAAAGACAG | 840 |
|  | CTTGTGTTGT | ATGCATGGGA | TCGACAGTTC | ATGGACGGCG | 880 |
|  | CTACCCAGAG | AGGCGGCATT | TGCGTACACC | GTGGGTCGTC | 920 |
|  | ATGAGTACCG | GGACATCGTG | TTCGTGTTTA | TTTGTTCATG | 960 |
|  | TCGAAGTGCA | CTAAGACACG | AGACGAAAGG | GTGGTTCCGC | 1000 |
|  | CCCTGGCAGC | ATCACGTAGT | GGTTTCTTTG | TCGAGAACAG | 1040 |

FIG. 1B pGM613

|  10  |  20  |  30  |  40  | |
|---|---|---|---|---|
| 1234567890 | 1234567890 | 1234567890 | 1234567890 | |
| CGGCAGTCCG | AGGCCACTTG | AGACAGGATG | TTTGAGTGTA | 1080 |
| TACAGACAAC | GTGGTCACAG | CATGAGGCAA | AGCTGTCTAA | 1120 |
| GCAGCCATTT | GCGCGAGCGA | AGTCATCCAT | GCCGACTGTG | 1160 |
| TGAGCCTCTT | TCGTCACTTT | GAATGAGACA | GAAACTAAGA | 1200 |
| CTCGCAGCAG | GTCTGAATAT | TGCGAATAAT | CTACTTTTAA | 1240 |
| AACCAAAAAA | AAAAAAAAAA | AACTCGAG | | 1268 |

FIG. 1C pTXG1-2

|  10 | 20 | 30 | 40 | |
|---|---|---|---|---|
| 1234567890 | 1234567890 | 1234567890 | 1234567890 | |
| AGACCCCGCC | ACCGCCCGTG | ACGAACCACG | AACCGCGGCG | 40 |
| AACGGCGAGC | TCACCGGGTT | TTCAGAGACG | CGCGAGATCC | 80 |
| CTGATTTCGT | TTACCATTGA | CGCCCGCCGC | CGTCGACGTC | 120 |
| TTTGGAACGT | GTTTCACGTT | TGAGTTGCAC | TGTTACTTTC | 160 |
| TTCGGATTAC | ATTCTTCCAC | TAAAAGCTGG | TTTTGTCCAG | 200 |
| TATCCATTCG | TCGCTACCGT | TGCGCAGTCA | CGTTGAATTT | 240 |
| TGCAGCGGCA | AAACATCTTG | TGTAAAATTC | GAGTTTTGTT | 280 |
| GATGATTGAA | GTACCCTATA | TTGGGGCTTG | CTAACGTTTT | 320 |
| GTATTAAAAG | GGATTACTGC | GGCGTCTCAT | TTCCAAAATG | 360 |
| GCCCGACACG | CAATTTTTTC | CGCGCTTTGT | GTTTTAGGCC | 400 |
| TGGTGGCGGC | GGCTTTGCCC | CAGTTCGCTA | CCGCGGCCAC | 440 |
| CGCGTCAGAT | GACGAACTGA | TGAGTCGAAT | CCGAAAT | 477 |

FIG. 2

Composite P29 Gene Sequence

```
         10         20         30         40
1234567890 1234567890 1234567890 1234567890
AGACCCCGCC ACCGCCCGTG ACGAACCACG AACCGCGGCG           40

AACGGCGAGC TCACCGGGTT TTCAGAGACG CGCGAGATCC           80

CTGATTTCGT TTACCATTGA CGCCCGCCGC CGTCGACGTC          120

TTTGGAACGT GTTTCACGTT TGAGTTGCAC TGTTACTTTC          160

TTCGGATTAC ATTCTTCCAC TAAAAGCTGG TTTTGTCCAG          200

TATCCATTCG TCGCTACCGT TGCGCAGTCA CGTTGAATTT          240

TGCAGCGGCA AAACATCTTG TGTAAAATTC GAGTTTTGTT          280

GATGATTGAA GTACCCTATA TTGGGGCTTG CTAACGTTTT          320

GTATTAAAAG GGATTACTGC GGCGTCTCAT TTCCAAAATG          360
                                         Met

GCCCGACACG CAATTTTTTC CGCGCTTTGT GTTTTAGGCC          400
AlaArgHisA laIlePheSe rAlaLeuCys ValLeuGlyL

TGGTGGCGGC GGCTTTGCCC CAGTTCGCTA CCGCGGCCAC          440
euValAlaAl aAlaLeuPro GlnPheAlaT hrAlaAlaTh

CGCGTCAGAT GACGAACTGA TGAGTCGAAT CCGAAATTCT          480
rAlaSerAsp AspGluLeuM etSerArgIl eArgAsnSer

GACTTTTTCG ATGGTCAAGC ACCCGTTGAC AGTCTCAGAC          520
AspPhePheA spGlyGlnAl aProValAsp SerLeuArgP
```

FIG. 3A

Composite P29 Gene Sequence

```
         10         20         30         40
1234567890 1234567890 1234567890 1234567890
CGACGAACGC CGGTGTCGAC TCGAAAGGGA CCGACGATCA      560
roThrAsnAl aGlyValAsp SerLysGlyT hrAspAspHi

CCTCACCACC AGCATGGATA AGGCATCTGT AGAGAGTCAG      600
sLeuThrThr SerMetAspL ysAlaSerVa lGluSerGln

CTTCCGAGAA GAGAGCCATT GGAGACGGAG CCAGATGAAC      640
LeuProArgA rgGluProLe uGluThrGlu ProAspGluG

AAGAAGAAGT TCATTTCAGG AAGCGAGGCG TCCGTTCCGA      680
lnGluGluVa lHisPheArg LysArgGlyV alArgSerAs

CGCTGAAGTG ACTGACGACA ACATCTACGA GGAGCACACT      720
pAlaGluVal ThrAspAspA snIleTyrGl uGluHisThr

GATCGTAAGG TGGTTCCGAG GAAGTCGGAG GGCAAGCGAA      760
AspArgLysV alValProAr gLysSerGlu GlyLysArgS

GCTTCAAAGA CTTGCTGAAG AAGCTCGCGC TGCCGGCTGT      800
erPheLysAs pLeuLeuLys LysLeuAlaL euProAlaVa

TGGTATGGGT GCATCGTATT TTGCCGCTGA TAGACTTGTG      840
lGlyMetGly AlaSerTyrP heAlaAlaAs pArgLeuVal

CCGGAACTAA CAGAGGAGCA ACAGAGAGGC GACGAACCCC      880
ProGluLeuT hrGluGluGl nGlnArgGly AspGluProL

TAACCACCGG CCAGAATGTG GGCACTGTGT TAGGCTTCGC      920
euThrThrGl yGlnAsnVal GlyThrValL euGlyPheAl

AGCGCTTGCT GCTGCCGCAG CGTTCCTTGG CATGGGTCTC      960
aAlaLeuAla AlaAlaAlaA laPheLeuGl yMetGlyLeu

ACGAGGACGT ACCGACATTT TTCCCCACGC AAAAACAGAT     1000
ThrArgThrT yrArgHisPh eSerProArg LysAsnArgS

CACGGCAGCC TGCACTCGAG CAAGAGGTGC CTGAATCAGG     1040
erArgGlnPr oAlaLeuGlu GlnGluValP roGluSerGl
```

FIG.3B

Composite P29 Gene Sequence

```
           10         20         30         40
       1234567890 1234567890 1234567890 1234567890
       CGAAGATGGG GAGGATGCCC GCCAGTAGGA TATGGGGGCT    1080
       yGluAspGly GluAspAlaA rgGln

AATAAAAGTG AGTAGGAGCT CGAGGACAGT GTCCCGAACG    1120

CGCCTGAGAG GCAGACAGAC ACAGAAGAGT GAAGAAAAAC    1160

AACATGGTAT TACGTGCGGT GAGTGTTTGC TGTCACGTGT    1200

TTTTTGCGCC ACAAAGACAG CTTGTGTTGT ATGCATGGGA    1240

TCGACAGTTC ATGGACGGCG CTACCCAGAG AGGCGGCATT    1280

TGCGTACACC GTGGGTCGTC ATGAGTACCG GACATCGTG     1320

TTCGTGTTTA TTTGTTCATG TCGAAGTGCA CTAAGACACG    1360

AGACGAAAGG GTGGTTCCGC CCCTGGCAGC ATCACGTAGT    1400

GGTTTCTTTG TCGAGAACAG CGGCAGTCCG AGGCCACTTG    1440

AGACAGGATG TTTGAGTGTA TACAGACAAC GTGGTCACAG    1480

CATGAGGCAA AGCTGTCTAA GCAGCCATTT GCGCGAGCGA    1520

AGTCATCCAT GCCGACTGTG TGAGCCTCTT TCGTCACTTT    1560
```

FIG.3C

Composite P29 Gene Sequence

|  |  |  |  |  |
|---|---|---|---|---|
| 10 | 20 | 30 | 40 | |
| 1234567890 | 1234567890 | 1234567890 | 1234567890 | |
| GAATGAGACA | GAAACTAAGA | CTCGCAGCAG | GTCTGAATAT | 1600 |
| TGCGAATAAT | CTACTTTTAA | AACCAAAAAA | AAAAAAAAAA | 1640 |
| AACTCGAG | | | | 1648 |

FIG. 3D

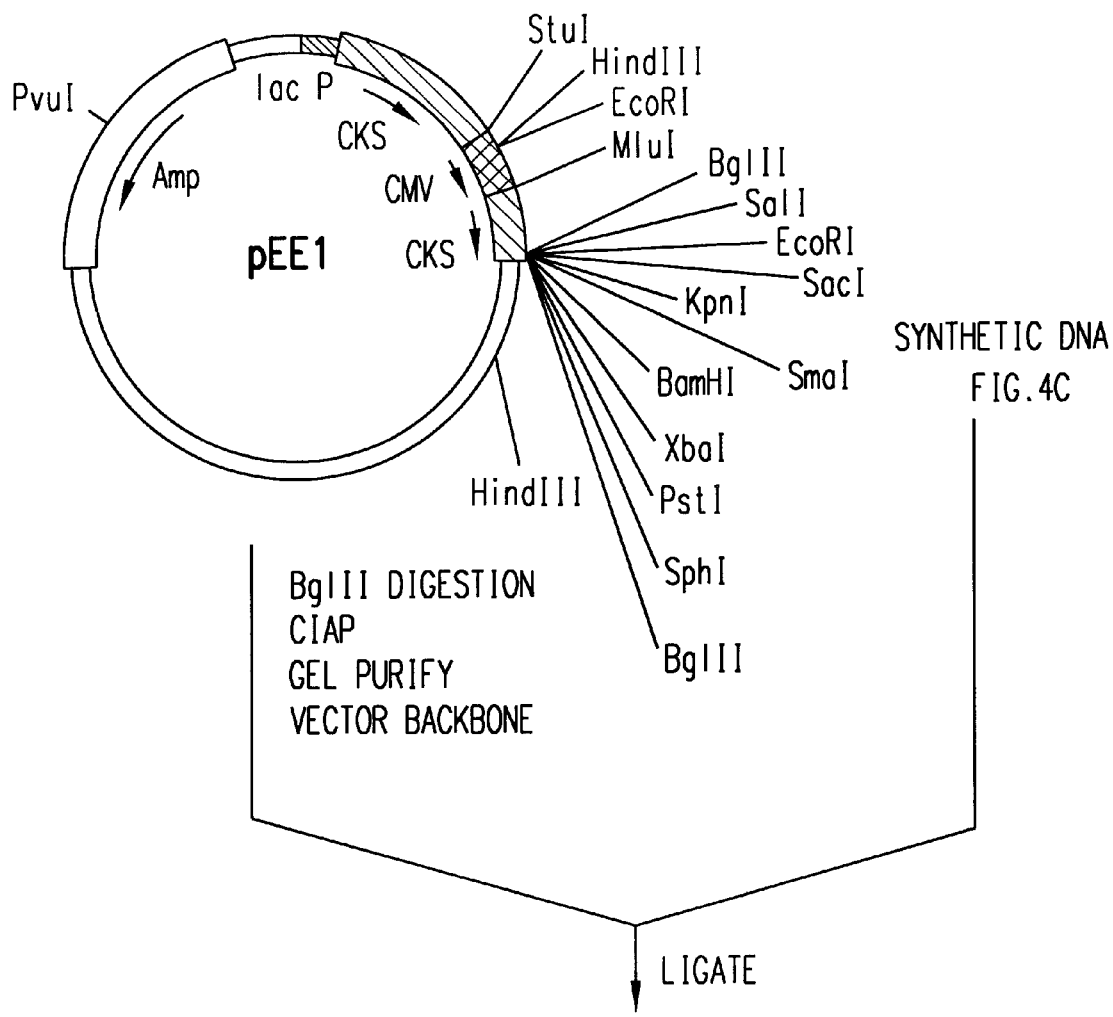
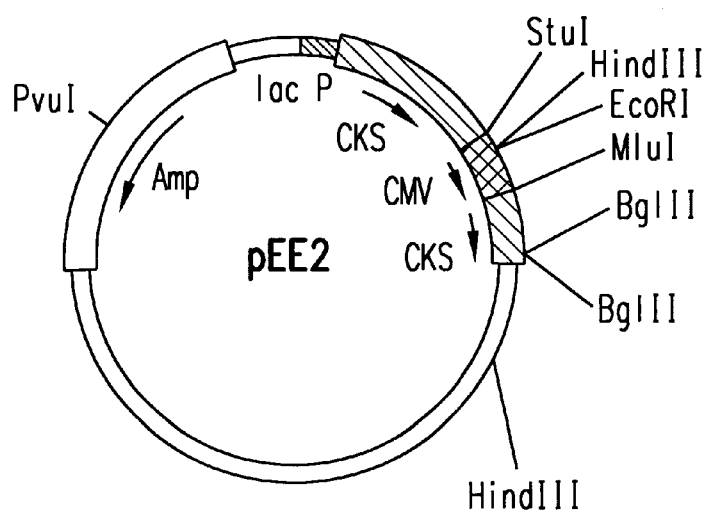
FIG.4A

Old Polylinker Sequence

```
         10          20          30          40
1234567890  1234567890  1234567890  1234567890

SmaI
BglII        SalI  EcoRI       SacI   KpnI
  ▼           ▼     ▼           ▼     ▼▼
AGATCTCGAC  CCGTCGACGA  ATTCGAGCTC  GGTACCCGGG    40
 AspLeuAsp   ProSerThrA  snSerSerSe  rValProGly

BamHI XbaI       PstI       SphI        BglII
  ▼    ▼          ▼          ▼            ▼
GATCCTCTAG  ACTGCAGGCA  TGCTAAGTAA  GTAGATCT      78
 AspProLeuA  spCysArgHi  sAlaLys
```

FIG.4B

New Sequence

```
         10         20         30         40
 1234567890 1234567890 1234567890 1234567890

BstYI
BglII                 BbsI
▼                     ▼
AGATCTCGAC CCATCTACCA ATTCGTCTTC TGTTCCGGGT        40
 AspLeuAsp ProSerThrA snSerSerSe rValProGly

BstYI
                                BglII
                                ▼
GATCCGCTAG ACTGCCGTCA CGCTAAGTAA GTAGATCT          78
 AspProLeuA spCysArgHi sAlaLys
```

FIG.4C pEE3 Polylinker Sequence

```
         10         20         30         40
1234567890 1234567890 1234567890 1234567890
```

```
           EcoRI                    MluI
  StuI           SacI BamHI         PstI
  ▼   ▼          ▼    ▼             ▼▼
AGGCCTGAAT TCGAGCTCTG GGATCCGTCT GCAGACGCGT          40
GlyLeuAsn  SerSerSerG lyIleArgLe uGlnThrArg
```

FIG.5B pToxo-P29

```
          10         20         30         40
    1234567890 1234567890 1234567890 1234567890
    GAATTAATTC CCATTAATGT GAGTTAGCTC ACTCATTAGG    40

CACCCCAGGC TTTACACTTT ATGTTCCGGC TCGTATTTTG    80

TGTGGAATTG TGAGCGGATA ACAATTGGGC ATCCAGTAAG   120

GAGGTTTAAA TGAGTTTTGT GGTCATTATT CCCGCGCGCT   160
             M etSerPheVa lValIleIle ProAlaArgT

ACGCGACGTC GCGTCTGCCC GGTAAACCAT TGGTTGATAT   200
    yrAlaThrSe rArgLeuPro GlyLysProL euValAspIl

TAACGGCAAA CCCATGATTG TTCATGTTCT TGAACGCGCG   240
    eAsnGlyLys ProMetIleV alHisValLe uGluArgAla

CGTGAATCAG GTGCCGAGCG CATCATCGTG GCAACCGATC   280
    ArgGluSerG lyAlaGluAr gIleIleVal AlaThrAspH

ATGAGGATGT TGCCCGCGCC GTTGAAGCCG CTGGCGGTGA   320
    isGluAspVa lAlaArgAla ValGluAlaA laGlyGlyGl

AGTATGTATG ACGCGCGCCG ATCATCAGTC AGGAACAGAA   360
    uValCysMet ThrArgAlaA spHisGlnSe rGlyThrGlu

CGTCTGGCGG AAGTTGTCGA AAAATGCGCA TTCAGCGACG   400
    ArgLeuAlaG luValValGl uLysCysAla PheSerAspA

ACACGGTGAT CGTTAATGTG CAGGGTGATG AACCGATGAT   440
    spThrValIl eValAsnVal GlnGlyAspG luProMetIl

CCCTGCGACA ATCATTCGTC AGGTTGCTGA TAACCTCGCT   480
    eProAlaThr IleIleArgG lnValAlaAs pAsnLeuAla

CAGCGTCAGG TGGGTATGAC GACTCTGGCG GTGCCAATCC   520
    GlnArgGlnV alGlyMetTh rThrLeuAla ValProIleH
```

FIG. 7A pToxo-P29

|  |  |  |  |  |
|---|---|---|---|---|
| 10 | 20 | 30 | 40 | |
| 1234567890 | 1234567890 | 1234567890 | 1234567890 | |
| ACAATGCGGA | AGAAGCGTTT | AACCCGAATG | CGGTGAAAGT | 560 |
| isAsnAlaGl | uGluAlaPhe | AsnProAsnA | laValLysVa | |
| GGTTCTCGAC | GCTGAAGGGT | ATGCACTGTA | CTTCTCTCGC | 600 |
| lValLeuAsp | AlaGluGlyT | yrAlaLeuTy | rPheSerArg | |
| GCCACCATTC | CTTGGGATCG | TGATCGTTTT | GCAGAAGGCC | 640 |
| AlaThrIleP | roTrpAspAr | gAspArgPhe | AlaGluGlyL | |
| TGAATTCGAT | GGCCCGACAC | GCAATTTTTT | CCGCGCTTTG | 680 |
| euAsnSerMe | tAlaArgHis | AlaIlePheS | erAlaLeuCy | |
| TGTTTTAGGC | CTGGTGGCGG | CGGCTTTGCC | CCAGTTCGCT | 720 |
| sValLeuGly | LeuValAlaA | laAlaLeuPr | oGlnPheAla | |
| ACCGCGGCCA | CCGCGTCAGA | TGACGAACTG | ATGAGTCGAA | 760 |
| ThrAlaAlaT | hrAlaSerAs | pAspGluLeu | MetSerArgI | |
| TCCGAAATTC | TGACTTTTTC | GATGGTCAAG | CACCCGTTGA | 800 |
| leArgAsnSe | rAspPhePhe | AspGlyGlnA | laProValAs | |
| CAGTCTCAGA | CCGACGAACG | CCGGTGTCGA | CTCGAAAGGG | 840 |
| pSerLeuArg | ProThrAsnA | laGlyValAs | pSerLysGly | |
| ACCGACGATC | ACCTCACCAC | CAGCATGGAT | AAGGCATCTG | 880 |
| ThrAspAspH | isLeuThrTh | rSerMetAsp | LysAlaSerV | |
| TAGAGAGTCA | GCTTCCGAGA | AGAGAGCCAT | TGGAGACGGA | 920 |
| alGluSerGl | nLeuProArg | ArgGluProL | euGluThrGl | |
| GCCAGATGAA | CAAGAAGAAG | TTCATTTCAG | GAAGCGAGGC | 960 |
| uProAspGlu | GlnGluGluV | alHisPheAr | gLysArgGly | |
| GTCCGTTCCG | ACGCTGAAGT | GACTGACGAC | AACATCTACG | 1000 |
| ValArgSerA | spAlaGluVa | lThrAspAsp | AsnIleTyrG | |
| AGGAGCACAC | TGATCGTAAG | GTGGTTCCGA | GGAAGTCGGA | 1040 |
| luGluHisTh | rAspArgLys | ValValProA | rgLysSerGl | |

FIG.7B pToxo-P29

```
          10         20         30         40
 1234567890 1234567890 1234567890 1234567890
 GGGCAAGCGA AGCTTCAAAG ACTTGCTGAA GAAGCTCGCG      1080
 uGlyLysArg SerPheLysA spLeuLeuLy sLysLeuAla

CTGCCGGCTG TTGGTATGGG TGCATCGTAT TTTGCCGCTG      1120
 LeuProAlaV alGlyMetGl yAlaSerTyr PheAlaAlaA

ATAGACTTGT GCCGGAACTA ACAGAGGAGC AACAGAGAGG      1160
 spArgLeuVa lProGluLeu ThrGluGluG lnGlnArgGl

CGACGAACCC CTAACCACCG GCCAGAATGT GGGCACTGTG      1200
 yAspGluPro LeuThrThrG lyGlnAsnVa lGlyThrVal

TTAGGCTTCG CAGCGCTTGC TGCTGCCGCA GCGTTCCTTG      1240
 LeuGlyPheA laAlaLeuAl aAlaAlaAla AlaPheLeuG

GCATGGGTCT CACGAGGACG TACCGACATT TTTCCCCACG      1280
 lyMetGlyLe uThrArgThr TyrArgHisP heSerProAr

CAAAAACAGA TCACGGCAGC CTGCACTCGA GCAAGAGGTG      1320
 gLysAsnArg SerArgGlnP roAlaLeuGl uGlnGluVal

CCTGAATCAG GCGAAGATGG GGAGGATGCC CGCCAGCGGA      1360
 ProGluSerG lyGluAspGl yGluAspAla ArgGlnArgI

TCCGTCTGCA GACGCGTCTT GAAACCGTTG GCGATAACTT      1400
 leArgLeuGl nThrArgLeu GluThrValG lyAspAsnPh

CCTGCGTCAT CTTGGTATTT ATGGCTACCG TGCAGGCTTT      1440
 eLeuArgHis LeuGlyIleT yrGlyTyrAr gAlaGlyPhe

ATCCGTCGTT ACGTCAACTG GCAGCCAAGT CCGTTAGAAC      1480
 IleArgArgT yrValAsnTr pGlnProSer ProLeuGluH

ACATCGAAAT GTTAGAGCAG CTTCGTGTTC TGTGGTACGG      1520
 isIleGluMe tLeuGluGln LeuArgValL euTrpTyrGl

CGAAAAAATC CATGTTGCTG TTGCTCAGGA AGTTCCTGGC      1560
 yGluLysIle HisValAlaV alAlaGlnGl uValProGly
```

FIG.7C pToxo-P29

|  10       |  20       |  30       |  40       |      |
|-----------|-----------|-----------|-----------|------|
| 1234567890| 1234567890| 1234567890| 1234567890|      |
| ACAGGTGTGG| ATACCCCTGA| AGATCTCGAC| CCATCTACCA| 1600 |
| ThrGlyValA| spThrProGl| uAspLeuAsp| ProSerThrA|      |
| ATTCGTCTTC| TGTTCCGGGT| GATCCGCTAG| ACTGCCGTCA| 1640 |
| snSerSerSe| rValProGly| AspProLeuA| spCysArgHi|      |
| CGCTAAGTAA| GTAGATCTTG| AGCGCGTTCG| CGCTGAAATG| 1680 |
| sAlaLys   |           |           |           |      |
| CGCTAATTTC| ACTTCACGAC| ACTTCAGCCA| ATTTTGGGAG| 1720 |
| GAGTGTCGTA| CCGTTACGAT| TTTCCTCAAT| TTTTCTTTTC| 1760 |
| AACAATTGAT| CTCATTCAGG| TGACATCTTT| TATATTGGCG| 1800 |
| CTCATTATGA| AAGCAGTAGC| TTTTATGAGG| GTAATCTGAA| 1840 |
| TGGAACAGCT| GCGTGCCGAA| TTAAGCCATT| TACTGGGCGA| 1880 |
| AAAACTCAGT| CGTATTGAGT| GCGTCAATGA| AAAAGCGGAT| 1920 |
| ACGGCGTTGT| GGGCTTTGTA| TGACAGCCAG| GGAAACCCAA| 1960 |
| TGCCGTTAAT| GGCAAGAAGC| TTAGCCCGCC| TAATGAGCGG| 2000 |
| GCTTTTTTTT| CGACGCGAGG| CTGGATGGCC| TTCCCCATTA| 2040 |
| TGATTCTTCT| CGCTTCCGGC| GGCATCGGGA| TGCCCGCGTT| 2080 |

FIG. 7D pToxo-P29

|  10        |  20        |  30        |  40        |      |
|------------|------------|------------|------------|------|
| 1234567890 | 1234567890 | 1234567890 | 1234567890 |      |
| GCAGGCCATG | CTGTCCAGGC | AGGTAGATGA | CGACCATCAG | 2120 |
| GGACAGCTTC | AAGGATCGCT | CGCGGCTCTT | ACCAGCCTAA | 2160 |
| CTTCGATCAC | TGGACCGCTG | ATCGTCACGG | CGATTTATGC | 2200 |
| CGCCTCGGCG | AGCACATGGA | ACGGGTTGGC | ATGGATTGTA | 2240 |
| GGCGCCGCCC | TATACCTTGT | CTGCCTCCCC | GCGTTGCGTC | 2280 |
| GCGGTGCATG | GAGCCGGGCC | ACCTCGACCT | GAATGGAAGC | 2320 |
| CGGCGGCACC | TCGCTAACGG | ATTCACCACT | CCAAGAATTG | 2360 |
| GAGCCAATCA | ATTCTTGCGG | AGAACTGTGA | ATGCGCAAAC | 2400 |
| CAACCCTTGG | CAGAACATAT | CCATCGCGTC | CGCCATCTCC | 2440 |
| AGCAGCCGCA | CGCGGCGCAT | CTCGGGCAGC | GTTGGGTCCT | 2480 |
| GGCCACGGGT | GCGCATGATC | GTGCTCCTGT | CGTTGAGGAC | 2520 |
| CCGGCTAGGC | TGGCGGGGTT | GCCTTACTGG | TTAGCAGAAT | 2560 |
| GAATCACCGA | TACGCGAGCG | AACGTGAAGC | GACTGCTGCT | 2600 |

FIG. 7E pToxo-P29

|  10        |  20        |  30        |  40        |      |
| ---------- | ---------- | ---------- | ---------- | ---- |
| 1234567890 | 1234567890 | 1234567890 | 1234567890 |      |
| GCAAAACGTC | TGCGACCTGA | GCAACAACAT | GAATGGTCTT | 2640 |
| CGGTTTCCGT | GTTTCGTAAA | GTCTGGAAAC | GCGGAAGTCA | 2680 |
| GCGCCCTGCA | CCATTATGTT | CCGGATCTGC | ATCGCAGGAT | 2720 |
| GCTGCTGGCT | ACCCTGTGGA | ACACCTACAT | CTGTATTAAC | 2760 |
| GAAGCGCTTC | TTCCGCTTCC | TCGCTCACTG | ACTCGCTGCG | 2800 |
| CTCGGTCGTT | CGGCTGCGGC | GAGCGGTATC | AGCTCACTCA | 2840 |
| AAGGCGGTAA | TACGGTTATC | CACAGAATCA | GGGGATAACG | 2880 |
| CAGGAAAGAA | CATGTGAGCA | AAAGGCCAGC | AAAAGGCCAG | 2920 |
| GAACCGTAAA | AAGGCCGCGT | TGCTGGCGTT | TTTCCATAGG | 2960 |
| CTCCGCCCCC | CTGACGAGCA | TCACAAAAAT | CGACGCTCAA | 3000 |
| GTCAGAGGTG | GCGAAACCCG | ACAGGACTAT | AAAGATACCA | 3040 |
| GGCGTTTCCC | CCTGGAAGCT | CCCTCGTGCG | CTCTCCTGTT | 3080 |
| CCGACCCTGC | CGCTTACCGG | ATACCTGTCC | GCCTTTCTCC | 3120 |

FIG. 7F pToxo-P29

| | | | | |
|---|---|---|---|---|
| 10 | 20 | 30 | 40 | |
| 1234567890 | 1234567890 | 1234567890 | 1234567890 | |
| CTTCGGGAAG | CGTGGCGCTT | TCTCAATGCT | CACGCTGTAG | 3160 |
| GTATCTCAGT | TCGGTGTAGG | TCGTTCGCTC | CAAGCTGGGC | 3200 |
| TGTGTGCACG | AACCCCCCGT | TCAGCCCGAC | CGCTGCGCCT | 3240 |
| TATCCGGTAA | CTATCGTCTT | GAGTCCAACC | CGGTAAGACA | 3280 |
| CGACTTATCG | CCACTGGCAG | CAGCCACTGG | TAACAGGATT | 3320 |
| AGCAGAGCGA | GGTATGTAGG | CGGTGCTACA | GAGTTCTTGA | 3360 |
| AGTGGTGGCC | TAACTACGGC | TACACTAGAA | GGACAGTATT | 3400 |
| TGGTATCTGC | GCTCTGCTGA | AGCCAGTTAC | CTTCGGAAAA | 3440 |
| AGAGTTGGTA | GCTCTTGATC | CGGCAAACAA | ACCACCGCTG | 3480 |
| GTAGCGGTGG | TTTTTTTGTT | TGCAAGCAGC | AGATTACGCG | 3520 |
| CAGAAAAAAA | GGATCTCAAG | AAGATCCTTT | GATCTTTTCT | 3560 |
| ACGGGGTCTG | ACGCTCAGTG | GAACGAAAAC | TCACGTTAAG | 3600 |
| GGATTTTGGT | CATGAGATTA | TCAAAAAGGA | TCTTCACCTA | 3640 |

FIG. 7G pToxo-P29

```
         10         20         30         40
1234567890 1234567890 1234567890 1234567890
GATCCTTTTA AATTAAAAAT GAAGTTTTAA ATCAATCTAA    3680

AGTATATATG AGTAAACTTG GTCTGACAGT TACCAATGCT    3720

TAATCAGTGA GGCACCTATC TCAGCGATCT GTCTATTTCG    3760

TTCATCCATA GTTGCCTGAC TCCCCGTCGT GTAGATAACT    3800

ACGATACGGG AGGGCTTACC ATCTGGCCCC AGTGCTGCAA    3840

TGATACCGCG AGACCCACGC TCACCGGCTC CAGATTTATC    3880

AGCAATAAAC CAGCCAGCCG GAAGGGCCGA GCGCAGAAGT    3920

GGTCCTGCAA CTTTATCCGC CTCCATCCAG TCTATTAATT    3960

GTTGCCGGGA AGCTAGAGTA AGTAGTTCGC CAGTTAATAG    4000

TTTGCGCAAC GTTGTTGCCA TTGCTACAGG CATCGTGGTG    4040

TCACGCTCGT CGTTTGGTAT GGCTTCATTC AGCTCCGGTT    4080

CCCAACGATC AAGGCGAGTT ACATGATCCC CCATGTTGTG    4120

CAAAAAAGCG GTTAGCTCCT TCGGTCCTCC GATCGTTGTC    4160
```

FIG.7H pToxo-P29

```
         10         20         30         40
  1234567890 1234567890 1234567890 1234567890
  AGAAGTAAGT TGGCCGCAGT GTTATCACTC ATGGTTATGG    4200

CAGCACTGCA TAATTCTCTT ACTGTCATGC CATCCGTAAG    4240

ATGCTTTTCT GTGACTGGTG AGTACTCAAC CAAGTCATTC    4280

TGAGAATAGT GTATGCGGCG ACCGAGTTGC TCTTGCCCGG    4320

CGTCAACACG GATAATACC  GCGCCACATA GCAGAACTTT    4360

AAAAGTGCTC ATCATTGGAA AACGTTCTTC GGGGCGAAAA    4400

CTCTCAAGGA TCTTACCGCT GTTGAGATCC AGTTCGATGT    4440

AACCCACTCG TGCACCCAAC TGATCTTCAG CATCTTTTAC    4480

TTTCACCAGC GTTTCTGGGT GAGCAAAAAC AGGAAGGCAA    4520

AATGCCGCAA AAAGGGAAT  AAGGGCGACA CGGAAATGTT    4560

GAATACTCAT ACTCTTCCTT TTTCAATATT ATTGAAGCAT    4600

TTATCAGGGT TATTGTCTCA TGAGCGGATA CATATTTGAA    4640

TGTATTTAGA AAAATAAACA AATAGGGGTT CCGCGCACAT    4680
```

FIG. 71 pToxo-P29

|  | 10 | 20 | 30 | 40 |  |
|---|---|---|---|---|---|
|  | 1234567890 | 1234567890 | 1234567890 | 1234567890 |  |
|  | TTCCCCGAAA | AGTGCCACCT | GACGTCTAAG | AAACCATTAT | 4720 |
|  | TATCATGACA | TTAACCTATA | AAAATAGGCG | TATCACGAGG | 4760 |
|  | CCCTTTCGTC | TTCAA |  |  | 4775 |

FIG.7J pToxo-P30

```
         10          20          30          40
    1234567890  1234567890  1234567890  1234567890
    ACAATGCGGA  AGAAGCGTTT  AACCCGAATG  CGGTGAAAGT      560
    isAsnAlaGl  uGluAlaPhe  AsnProAsnA  laValLysVa

GGTTCTCGAC  GCTGAAGGGT  ATGCACTGTA  CTTCTCTCGC      600
    lValLeuAsp  AlaGluGlyT  yrAlaLeuTy  rPheSerArg

GCCACCATTC  CTTGGGATCG  TGATCGTTTT  GCAGAAGGCC      640
    AlaThrIleP  roTrpAspAr  gAspArgPhe  AlaGluGlyL

TTAATTCGAT  GCTTGTTGCC  AATCAAGTTG  TCACCTGCCC      680
    euAsnSerMe  tLeuValAla  AsnGlnValV  alThrCysPr

AGATAAAAAA  TCGACAGCCG  CGGTCATTCT  CACACCGACG      720
    oAspLysLys  SerThrAlaA  laValIleLe  uThrProThr

GAGAACCACT  TCACTCTCAA  GTGCCCTAAA  ACAGCGCTCA      760
    GluAsnHisP  heThrLeuLy  sCysProLys  ThrAlaLeuT

CAGAGCCTCC  CACTCTTGCG  TACTCACCCA  ACAGGCAAAT      800
    hrGluProPr  oThrLeuAla  TyrSerProA  snArgGlnIl

CTGCCCAGCG  GGTACTACAA  GTAGCTGTAC  ATCAAAGGCT      840
    eCysProAla  GlyThrThrS  erSerCysTh  rSerLysAla

GTAACATTGA  GCTCCTTGAT  TCCTGAAGCA  GAAGATAGCT      880
    ValThrLeuS  erSerLeuIl  eProGluAla  GluAspSerT

GGTGGACGGG  GGATTCTGCT  AGTCTCGACA  CGGCAGGCAT      920
    rpTrpThrGl  yAspSerAla  SerLeuAspT  hrAlaGlyIl

CAAACTCACA  GTTCCAATCG  AGAAGTTCCC  CGTGACAACG      960
    eLysLeuThr  ValProIleG  luLysPhePr  oValThrThr

CAGACGTTTG  TGGTCGGTTG  CATCAAGGGA  GACGACGCAC     1000
    GlnThrPheV  alValGlyCy  sIleLysGly  AspAspAlaG

AGAGTTGTAT  GGTCACGGTG  ACAGTACAAG  CCAGAGCCTC     1040
    lnSerCysMe  tValThrVal  ThrValGlnA  laArgAlaSe
```

FIG.9A pToxo-P30

```
          10         20         30         40
      1234567890 1234567890 1234567890 1234567890
      ATCGGTCGTC AATAATGTCG CAAGGTGCTC CTACGGTGCA       1080
      rSerValVal AsnAsnValA laArgCysSe rTyrGlyAla

GACAGCACTC TTGGTCCTGT CAAGTTGTCT GCGGAAGGAC       1120
      AspSerThrL euGlyProVa lLysLeuSer AlaGluGlyP

CCACTACAAT GACCCTCGTG TGCGGGAAAG ATGGAGTCAA       1160
      roThrThrMe tThrLeuVal CysGlyLysA spGlyValLy

AGTTCCTCAA GACAACAATC AGTACTGTTC CGGGACGACG       1200
      sValProGln AspAsnAsnG lnTyrCysSe rGlyThrThr

CTGACTGGTT GCAACGAGAA ATCGTTCAAA GATATTTTGC       1240
      LeuThrGlyC ysAsnGluLy sSerPheLys AspIleLeuP

CAAAATTAAC TGAGAACCCG TGGCAGGGTA ACGCTTCGAG       1280
      roLysLeuTh rGluAsnPro TrpGlnGlyA snAlaSerSe

TGATAAGGGT GCCACGCTAA CGATCAAGAA GGAAGCATTT       1320
      rAspLysGly AlaThrLeuT hrIleLysLy sGluAlaPhe

CCAGCCGAGT CAAAAAGCGT CATTATTGGA TGCACAGGGG       1360
      ProAlaGluS erLysSerVa lIleIleGly CysThrGlyG

GATCGCCTGA GAAGCATCAC TGTACCGTGA AACTGGAGTT       1400
      lySerProGl uLysHisHis CysThrValL ysLeuGluPh

TGCCGGGGCT GCAGGGTCAG CAAAATCGGC TGCGGGAACA       1440
      eAlaGlyAla AlaGlySerA laLysSerAl aAlaGlyThr

GCCAGTCACG TTTCCATTTT TGCCATGGTG ATCGGACTTA       1480
      AlaSerHisV alSerIlePh eAlaMetVal IleGlyLeuI

TTGGCTCTAT CGCAGCTTGT GTCGCGACGC GTCTTGAAAC       1520
      leGlySerIL eAlaAlaCys ValAlaThrA rgLeuGluTh

CGTTGGCGAT AACTTCCTGC GTCATCTTGG TATTTATGGC       1560
      rValGlyAsp AsnPheLeuA rgHisLeuGl yIleTyrGLy
```

FIG.9B pToxo-P30

|     10     |     20     |     30     |     40     |      |
|------------|------------|------------|------------|------|
| 1234567890 | 1234567890 | 1234567890 | 1234567890 |      |
| TACCGTGCAG | GCTTTATCCG | TCGTTACGTC | AACTGGCAGC | 1600 |
| TyrArgAlaG | lyPheIleAr | gArgTyrVal | AsnTrpGlnP |      |
| CAAGTCCGTT | AGAACACATC | GAAATGTTAG | AGCAGCTTCG | 1640 |
| roSerProLe | uGluHisIle | GluMetLeuG | luGlnLeuAr |      |
| TGTTCTGTGG | TACGGCGAAA | AAATCCATGT | TGCTGTTGCT | 1680 |
| gValLeuTrp | TyrGlyGluL | ysIleHisVa | lAlaValAla |      |
| CAGGAAGTTC | CTGGCACAGG | TGTGGATACC | CCTGAAGATC | 1720 |
| GlnGluValP | roGlyThrGl | yValAspThr | ProGluAspL |      |
| TCGACCCGTC | GACGAATTCG | AGCTCGGTAC | CCGGGGATCC | 1760 |
| euAspProSe | rThrAsnSer | SerSerValP | roGlyAspPr |      |
| TCTAGACTGC | AGGCATGCTA | AGTAAGTAGA | TCTTGAGCGC | 1800 |
| oLeuAspCys | ArgHisAlaL | ys         |            |      |
| GTTCGCGCTG | AAATGCGCTA | ATTTCACTTC | ACGACACTTC | 1840 |
| AGCCAATTTT | GGGAGGAGTG | TCGTACCGTT | ACGATTTTCC | 1880 |
| TCAATTTTTC | TTTTCAACAA | TTGATCTCAT | TCAGGTGACA | 1920 |
| TCTTTTATAT | TGGCGCTCAT | TATGAAAGCA | GTAGCTTTTA | 1960 |
| TGAGGGTAAT | CTGAATGGAA | CAGCTGCGTG | CCGAATTAAG | 2000 |
| CCATTTACTG | GGCGAAAAAC | TCAGTCGTAT | TGAGTGCGTC | 2040 |
| AATGAAAAAG | CGGATACGGC | GTTGTGGGCT | TTGTATGACA | 2080 |

FIG.9C pToxo-P30

|  10       |  20       |  30       |  40       |      |
|-----------|-----------|-----------|-----------|------|
| 1234567890| 1234567890| 1234567890| 1234567890|      |
| GCCAGGGAAA| CCCAATGCCG| TTAATGGCAA| GAAGCTTAGC| 2120 |
| CCGCCTAATG| AGCGGGCTTT| TTTTTCGACG| CGAGGCTGGA| 2160 |
| TGGCCTTCCC| CATTATGATT| CTTCTCGCTT| CCGGCGGCAT| 2200 |
| CGGGATGCCC| GCGTTGCAGG| CCATGCTGTC| CAGGCAGGTA| 2240 |
| GATGACGACC| ATCAGGGACA| GCTTCAAGGA| TCGCTCGCGG| 2280 |
| CTCTTACCAG| CCTAACTTCG| ATCACTGGAC| CGCTGATCGT| 2320 |
| CACGGCGATT| TATGCCGCCT| CGGCGAGCAC| ATGGAACGGG| 2360 |
| TTGGCATGGA| TTGTAGGCGC| CGCCCTATAC| CTTGTCTGCC| 2400 |
| TCCCCGCGTT| GCGTCGCGGT| GCATGGAGCC| GGGCCACCTC| 2440 |
| GACCTGAATG| GAAGCCGGCG| GCACCTCGCT| AACGGATTCA| 2480 |
| CCACTCCAAG| AATTGGAGCC| AATCAATTCT| TGCGGAGAAC| 2520 |
| TGTGAATGCG| CAAACCAACC| CTTGGCAGAA| CATATCCATC| 2560 |
| GCGTCCGCCA| TCTCCAGCAG| CCGCACGCGG| CGCATCTCGG| 2600 |

FIG. 9D pToxo-P30

| 10 | 20 | 30 | 40 | |
|---|---|---|---|---|
| 1234567890 | 1234567890 | 1234567890 | 1234567890 | |
| GCAGCGTTGG | GTCCTGGCCA | CGGGTGCGCA | TGATCGTGCT | 2640 |
| CCTGTCGTTG | AGGACCCGGC | TAGGCTGGCG | GGGTTGCCTT | 2680 |
| ACTGGTTAGC | AGAATGAATC | ACCGATACGC | GAGCGAACGT | 2720 |
| GAAGCGACTG | CTGCTGCAAA | ACGTCTGCGA | CCTGAGCAAC | 2760 |
| AACATGAATG | GTCTTCGGTT | TCCGTGTTTC | GTAAAGTCTG | 2800 |
| GAAACGCGGA | AGTCAGCGCC | CTGCACCATT | ATGTTCCGGA | 2840 |
| TCTGCATCGC | AGGATGCTGC | TGGCTACCCT | GTGGAACACC | 2880 |
| TACATCTGTA | TTAACGAAGC | GCTTCTTCCG | CTTCCTCGCT | 2920 |
| CACTGACTCG | CTGCGCTCGG | TCGTTCGGCT | GCGGCGAGCG | 2960 |
| GTATCAGCTC | ACTCAAAGGC | GGTAATACGG | TTATCCACAG | 3000 |
| AATCAGGGGA | TAACGCAGGA | AAGAACATGT | GAGCAAAAGG | 3040 |
| CCAGCAAAAG | GCCAGGAACC | GTAAAAAGGC | CGCGTTGCTG | 3080 |
| GCGTTTTTCC | ATAGGCTCCG | CCCCCCTGAC | GAGCATCACA | 3120 |

FIG.9E pToxo-P30

|  10 | 20 | 30 | 40 | |
| --- | --- | --- | --- | --- |
| 1234567890 | 1234567890 | 1234567890 | 1234567890 | |
| AAAATCGACG | CTCAAGTCAG | AGGTGGCGAA | ACCCGACAGG | 3160 |
| ACTATAAAGA | TACCAGGCGT | TTCCCCCTGG | AAGCTCCCTC | 3200 |
| GTGCGCTCTC | CTGTTCCGAC | CCTGCCGCTT | ACCGGATACC | 3240 |
| TGTCCGCCTT | TCTCCCTTCG | GGAAGCGTGG | CGCTTTCTCA | 3280 |
| ATGCTCACGC | TGTAGGTATC | TCAGTTCGGT | GTAGGTCGTT | 3320 |
| CGCTCCAAGC | TGGGCTGTGT | GCACGAACCC | CCCGTTCAGC | 3360 |
| CCGACCGCTG | CGCCTTATCC | GGTAACTATC | GTCTTGAGTC | 3400 |
| CAACCCGGTA | AGACACGACT | TATCGCCACT | GGCAGCAGCC | 3440 |
| ACTGGTAACA | GGATTAGCAG | AGCGAGGTAT | GTAGGCGGTG | 3480 |
| CTACAGAGTT | CTTGAAGTGG | TGGCCTAACT | ACGGCTACAC | 3520 |
| TAGAAGGACA | GTATTTGGTA | TCTGCGCTCT | GCTGAAGCCA | 3560 |
| GTTACCTTCG | GAAAAAGAGT | TGGTAGCTCT | TGATCCGGCA | 3600 |
| AACAAACCAC | CGCTGGTAGC | GGTGGTTTTT | TTGTTTGCAA | 3640 |

FIG.9F pToxo-P30

|  10  |  20  |  30  |  40  |    |
|------|------|------|------|----|
| 1234567890 | 1234567890 | 1234567890 | 1234567890 | |
| GCAGCAGATT | ACGCGCAGAA | AAAAAGGATC | TCAAGAAGAT | 3680 |
| CCTTTGATCT | TTTCTACGGG | GTCTGACGCT | CAGTGGAACG | 3720 |
| AAAACTCACG | TTAAGGGATT | TTGGTCATGA | GATTATCAAA | 3760 |
| AAGGATCTTC | ACCTAGATCC | TTTTAAATTA | AAAATGAAGT | 3800 |
| TTTAAATCAA | TCTAAAGTAT | ATATGAGTAA | ACTTGGTCTG | 3840 |
| ACAGTTACCA | ATGCTTAATC | AGTGAGGCAC | CTATCTCAGC | 3880 |
| GATCTGTCTA | TTTCGTTCAT | CCATAGTTGC | CTGACTCCCC | 3920 |
| GTCGTGTAGA | TAACTACGAT | ACGGGAGGGC | TTACCATCTG | 3960 |
| GCCCCAGTGC | TGCAATGATA | CCGCGAGACC | CACGCTCACC | 4000 |
| GGCTCCAGAT | TTATCAGCAA | TAAACCAGCC | AGCCGGAAGG | 4040 |
| GCCGAGCGCA | GAAGTGGTCC | TGCAACTTTA | TCCGCCTCCA | 4080 |
| TCCAGTCTAT | TAATTGTTGC | CGGGAAGCTA | GAGTAAGTAG | 4120 |
| TTCGCCAGTT | AATAGTTTGC | GCAACGTTGT | TGCCATTGCT | 4160 |

FIG.9G pToxo-P30

|  10        |  20        |  30        |  40        |      |
|------------|------------|------------|------------|------|
| 1234567890 | 1234567890 | 1234567890 | 1234567890 |      |
| ACAGGCATCG | TGGTGTCACG | CTCGTCGTTT | GGTATGGCTT | 4200 |
| CATTCAGCTC | CGGTTCCCAA | CGATCAAGGC | GAGTTACATG | 4240 |
| ATCCCCCATG | TTGTGCAAAA | AAGCGGTTAG | CTCCTTCGGT | 4280 |
| CCTCCGATCG | TTGTCAGAAG | TAAGTTGGCC | GCAGTGTTAT | 4320 |
| CACTCATGGT | TATGGCAGCA | CTGCATAATT | CTCTTACTGT | 4360 |
| CATGCCATCC | GTAAGATGCT | TTTCTGTGAC | TGGTGAGTAC | 4400 |
| TCAACCAAGT | CATTCTGAGA | ATAGTGTATG | CGGCGACCGA | 4440 |
| GTTGCTCTTG | CCCGGCGTCA | ACACGGGATA | ATACCGCGCC | 4480 |
| ACATAGCAGA | ACTTTAAAAG | TGCTCATCAT | TGGAAAACGT | 4520 |
| TCTTCGGGGC | GAAAACTCTC | AAGGATCTTA | CCGCTGTTGA | 4560 |
| GATCCAGTTC | GATGTAACCC | ACTCGTGCAC | CCAACTGATC | 4600 |
| TTCAGCATCT | TTTACTTTCA | CCAGCGTTTC | TGGGTGAGCA | 4640 |
| AAAACAGGAA | GGCAAAATGC | CGCAAAAAAG | GAATAAGGG  | 4680 |

FIG.9H pToxo-P30

|  10 | 20 | 30 | 40 | |
|---|---|---|---|---|
| 1234567890 | 1234567890 | 1234567890 | 1234567890 | |
| CGACACGGAA | ATGTTGAATA | CTCATACTCT | TCCTTTTTCA | 4720 |
| ATATTATTGA | AGCATTTATC | AGGGTTATTG | TCTCATGAGC | 4760 |
| GGATACATAT | TTGAATGTAT | TTAGAAAAAT | AAACAAATAG | 4800 |
| GGGTTCCGCG | CACATTTCCC | CGAAAAGTGC | CACCTGACGT | 4840 |
| CTAAGAAACC | ATTATTATCA | TGACATTAAC | CTATAAAAAT | 4880 |
| AGGCGTATCA | CGAGGCCCTT | TCGTCTTCAA | | 4910 |

FIG.91 pToxo-P35S

```
         10          20          30          40
 1234567890  1234567890  1234567890  1234567890
 GAATTAATTC  CCATTAATGT  GAGTTAGCTC  ACTCATTAGG    40

CACCCCAGGC  TTTACACTTT  ATGTTCCGGC  TCGTATTTTG    80

TGTGGAATTG  TGAGCGGATA  ACAATTGGGC  ATCCAGTAAG   120

GAGGTTTAAA  TGAGTTTTGT  GGTCATTATT  CCCGCGCGCT   160
          M  etSerPheVa  lValIleIle  ProAlaArgT

ACGCGTCGAC  GCGTCTGCCC  GGTAAACCAT  TGGTTGATAT   200
 yrAlaSerTh  rArgLeuPro  GlyLysProL  euValAspIl

TAACGGCAAA  CCCATGATTG  TTCATGTTCT  TGAACGCGCG   240
 eAsnGlyLys  ProMetIleV  alHisValLe  uGluArgAla

CGTGAATCAG  GTGCCGAGCG  CATCATCGTG  GCAACCGATC   280
 ArgGluSerG  lyAlaGluAr  gIleIleVal  AlaThrAspH

ATGAGGATGT  TGCCCGCGCC  GTTGAAGCCG  CTGGCGGTGA   320
 isGluAspVa  lAlaArgAla  ValGluAlaA  laGlyGlyGl

AGTATGTATG  ACGCGCGCCG  ATCATCAGTC  AGGAACAGAA   360
 uValCysMet  ThrArgAlaA  spHisGlnSe  rGlyThrGlu

CGTCTGGCGG  AAGTTGTCGA  AAAATGCGCA  TTCAGCGACG   400
 ArgLeuAlaG  luValValGl  uLysCysAla  PheSerAspA

ACACGGTGAT  CGTTAATGTG  CAGGGTGATG  AACCGATGAT   440
 spThrValIl  eValAsnVal  GlnGlyAspG  luProMetIl

CCCTGCGACA  ATCATTCGTC  AGGTTGCTGA  TAACCTCGCT   430
 eProAlaThr  IleIleArgG  lnValAlaAs  pAsnLeuAla

CAGCGTCAGG  TGGGTATGAC  GACTCTGGCG  GTGCCAATCC   520
 GlnArgGlnV  alGlyMetTh  rThrLeuAla  ValProIleH
```

FIG. 11A pToxo-P35S

```
         10         20         30         40
1234567890 1234567890 1234567890 1234567890
ACAATGCGGA AGAAGCGTTT AACCCGAATG CGGTGAAAGT    560
isAsnAlaGl uGluAlaPhe AsnProAsnA laValLysVa

GGTTCTCGAC GCTGAAGGGT ATGCACTGTA CTTCTCTCGC    600
lValLeuAsp AlaGluGlyT yrAlaLeuTy rPheSerArg

GCCACCATTC CTTGGGATCG TGATCGTTTT GCAGAAGGCC    640
AlaThrIleP roTrpAspAr gAspArgPhe AlaGluGlyL

TTATGAACGG TCCTTTGAGT TATCATCCAA GCAGTTACGG    680
euMetAsnGl yProLeuSer TyrHisProS erSerTyrGl

AGCGTCGTAT CCGAATCCGA GTAATCCTCT GCATGGAATG    720
yAlaSerTyr ProAsnProS erAsnProLe uHisGlyMet

CCCAAGCCAG AGAACCCGGT GAGACCGCCT CCTCCCGGTT    760
ProLysProG luAsnProVa lArgProPro ProProGlyP

TCCATCCAAG CGTTATTCCC AATCCCCCGT ACCCGCTGGG    800
heHisProSe rValIlePro AsnProProT yrProLeuGl

CACTCCAGCG AGCATGCCAC AGCCAGAGGT TCCGCCACTT    840
yThrProAla SerMetProG lnProGluVa lProProLeu

CAGCATCCCC CGCCAACGGG TTCCCCTCCC GCGGCCGCTC    880
GlnHisProP roProThrGl ySerProPro AlaAlaAlaP

CCCAGCCTCC ATATCCAGTG GGTACTCCAG TAATGCCACA    920
roGlnProPr oTyrProVal GlyThrProV alMetProGl

GCCAGAGATA CCGCCTGTTC ATCGGCCGCC GCCTCCGGGT    960
nProGluIle ProProValH isArgProPr oProProGly

TTCCGTCCCG AAGTGGCTCC CGTGCCCCCG TATCCAGTGG   1000
PheArgProG luValAlaPr oValProPro TyrProValG

GCACTCCAAC GGGCATGCCC CAGCCGGAGA TACCGGCAGT   1040
lyThrProTh rGlyMetPro GlnProGluI leProAlaVa
```

FIG. 11B pToxo-P35S

|  |  |  |  |  |
|---|---|---|---|---|
| 10 | 20 | 30 | 40 | |
| 1234567890 | 1234567890 | 1234567890 | 1234567890 | |
| TCACCATACG | CGTCTTGAAA | CCGTTGGCGA | TAACTTCCTG | 1080 |
| lHisHisThr | ArgLeuGluT | hrValGlyAs | pAsnPheLeu | |
| CGTCATCTTG | GTATTTATGG | CTACCGTGCA | GGCTTTATCC | 1120 |
| ArgHisLeuG | lyIleTyrGl | yTyrArgAla | GlyPheIleA | |
| GTCGTTACGT | CAACTGGCAG | CCAAGTCCGT | TAGAACACAT | 1160 |
| rgArgTyrVa | lAsnTrpGln | ProSerProL | euGluHisIl | |
| CGAAATGTTA | GAGCAGCTTC | GTGTTCTGTG | GTACGGCGAA | 1200 |
| eGluMetLeu | GluGlnLeuA | rgValLeuTr | pTyrGlyGlu | |
| AAAATCCATG | TTGCTGTTGC | TCAGGAAGTT | CCTGGCACAG | 1240 |
| LysIleHisV | alAlaValAl | aGlnGluVal | ProGlyThrG | |
| GTGTGGATAC | CCCTGAAGAT | CTCGACCCGT | CGACGAATTC | 1280 |
| lyValAspTh | rProGluAsp | LeuAspProS | erThrAsnSe | |
| GAGCTCGGTA | CCCGGGGATC | CTCTAGACTG | CAGGCATGCT | 1320 |
| rSerSerVal | ProGlyAspP | roLeuAspCy | sArgHisAla | |
| AAGTAAGTAG | ATCTTGAGCG | CGTTCGCGCT | GAAATGCGCT | 1360 |
| Lys | | | | |
| AATTTCACTT | CACGACACTT | CAGCCAATTT | TGGGAGGAGT | 1400 |
| GTCGTACCGT | TACGATTTTC | CTCAATTTTT | CTTTTCAACA | 1440 |
| ATTGATCTCA | TTCAGGTGAC | ATCTTTTATA | TTGGCGCTCA | 1480 |
| TTATGAAAGC | AGTAGCTTTT | ATGAGGGTAA | TCTGAATGGA | 1520 |
| ACAGCTGCGT | GCCGAATTAA | GCCATTTACT | GGGCGAAAAA | 1560 |

FIG. 11C pToxo-P35S

|  10  |  20  |  30  |  40  |  |
|---|---|---|---|---|
| 1234567890 | 1234567890 | 1234567890 | 1234567890 | |
| CTCAGTCGTA | TTGAGTGCGT | CAATGAAAAA | GCGGATACGG | 1600 |
| CGTTGTGGGC | TTTGTATGAC | AGCCAGGGAA | ACCCAATGCC | 1640 |
| GTTAATGGCA | AGAAGCTTAG | CCCGCCTAAT | GAGCGGGCTT | 1680 |
| TTTTTTCGAC | GCGAGGCTGG | ATGGCCTTCC | CCATTATGAT | 1720 |
| TCTTCTCGCT | TCCGGCGGCA | TCGGGATGCC | CGCGTTGCAG | 1760 |
| GCCATGCTGT | CCAGGCAGGT | AGATGACGAC | CATCAGGGAC | 1800 |
| AGCTTCAAGG | ATCGCTCGCG | GCTCTTACCA | GCCTAACTTC | 1840 |
| GATCACTGGA | CCGCTGATCG | TCACGGCGAT | TTATGCCGCC | 1880 |
| TCGGCGAGCA | CATGGAACGG | GTTGGCATGG | ATTGTAGGCG | 1920 |
| CCGCCCTATA | CCTTGTCTGC | CTCCCCGCGT | TGCGTCGCGG | 1960 |
| TGCATGGAGC | CGGGCCACCT | CGACCTGAAT | GGAAGCCGGC | 2000 |
| GGCACCTCGC | TAACGGATTC | ACCACTCCAA | GAATTGGAGC | 2040 |
| CAATCAATTC | TTGCGGAGAA | CTGTGAATGC | GCAAACCAAC | 2080 |

FIG. 11D pToxo-P35S

```
         10         20         30         40
    1234567890 1234567890 1234567890 1234567890
    CCTTGGCAGA ACATATCCAT CGCGTCCGCC ATCTCCAGCA    2120

GCCGCACGCG GCGCATCTCG GGCAGCGTTG GGTCCTGGCC    2160

ACGGGTGCGC ATGATCGTGC TCCTGTCGTT GAGGACCCGG    2200

CTAGGCTGGC GGGGTTGCCT TACTGGTTAG CAGAATGAAT    2240

CACCGATACG CGAGCGAACG TGAAGCGACT GCTGCTGCAA    2280

AACGTCTGCG ACCTGAGCAA CAACATGAAT GGTCTTCGGT    2320

TTCCGTGTTT CGTAAAGTCT GGAAACGCGG AAGTCAGCGC    2360

CCTGCACCAT TATGTTCCGG ATCTGCATCG CAGGATGCTG    2400

CTGGCTACCC TGTGGAACAC CTACATCTGT ATTAACGAAG    2440

CGCTTCTTCC GCTTCCTCGC TCACTGACTC GCTGCGCTCG    2480

GTCGTTCGGC TGCGGCGAGC GGTATCAGCT CACTCAAAGG    2520

CGGTAATACG GTTATCCACA GAATCAGGGG ATAACGCAGG    2560

AAAGAACATG TGAGCAAAAG GCCAGCAAAA GGCCAGGAAC    2600
```

FIG. 11E pToxo-P35S

|  10  |  20  |  30  |  40  | |
|---|---|---|---|---|
| 1234567890 | 1234567890 | 1234567890 | 1234567890 | |
| CGTAAAAAGG | CCGCGTTGCT | GGCGTTTTTC | CATAGGCTCC | 2640 |
| GCCCCCCTGA | CGAGCATCAC | AAAAATCGAC | GCTCAAGTCA | 2680 |
| GAGGTGGCGA | AACCCGACAG | GACTATAAAG | ATACCAGGCG | 2720 |
| TTTCCCCCTG | GAAGCTCCCT | CGTGCGCTCT | CCTGTTCCGA | 2760 |
| CCCTGCCGCT | TACCGGATAC | CTGTCCGCCT | TTCTCCCTTC | 2800 |
| GGGAAGCGTG | GCGCTTTCTC | AATGCTCACG | CTGTAGGTAT | 2840 |
| CTCAGTTCGG | TGTAGGTCGT | TCGCTCCAAG | CTGGGCTGTG | 2880 |
| TGCACGAACC | CCCCGTTCAG | CCCGACCGCT | GCGCCTTATC | 2920 |
| CGGTAACTAT | CGTCTTGAGT | CCAACCCGGT | AAGACACGAC | 2960 |
| TTATCGCCAC | TGGCAGCAGC | CACTGGTAAC | AGGATTAGCA | 3000 |
| GAGCGAGGTA | TGTAGGCGGT | GCTACAGAGT | TCTTGAAGTG | 3040 |
| GTGGCCTAAC | TACGGCTACA | CTAGAAGGAC | AGTATTTGGT | 3080 |
| ATCTGCGCTC | TGCTGAAGCC | AGTTACCTTC | GGAAAAAGAG | 3120 |

FIG. 11F pToxo-P35S

|     10     |     20     |     30     |     40     |      |
| ---------- | ---------- | ---------- | ---------- | ---- |
| 1234567890 | 1234567890 | 1234567890 | 1234567890 |      |
| TTGGTAGCTC | TTGATCCGGC | AAACAAACCA | CCGCTGGTAG | 3160 |
| CGGTGGTTTT | TTTGTTTGCA | AGCAGCAGAT | TACGCGCAGA | 3200 |
| AAAAAAGGAT | CTCAAGAAGA | TCCTTTGATC | TTTTCTACGG | 3240 |
| GGTCTGACGC | TCAGTGGAAC | GAAAACTCAC | GTTAAGGGAT | 3280 |
| TTTGGTCATG | AGATTATCAA | AAAGGATCTT | CACCTAGATC | 3320 |
| CTTTTAAATT | AAAAATGAAG | TTTTAAATCA | ATCTAAAGTA | 3360 |
| TATATGAGTA | AACTTGGTCT | GACAGTTACC | AATGCTTAAT | 3400 |
| CAGTGAGGCA | CCTATCTCAG | CGATCTGTCT | ATTTCGTTCA | 3440 |
| TCCATAGTTG | CCTGACTCCC | CGTCGTGTAG | ATAACTACGA | 3480 |
| TACGGGAGGG | CTTACCATCT | GGCCCCAGTG | CTGCAATGAT | 3520 |
| ACCGCGAGAC | CCACGCTCAC | CGGCTCCAGA | TTTATCAGCA | 3560 |
| ATAAACCAGC | CAGCCGGAAG | GGCCGAGCGC | AGAAGTGGTC | 3600 |
| CTGCAACTTT | ATCCGCCTCC | ATCCAGTCTA | TTAATTGTTG | 3640 |

FIG. 11G pToxo-P35S

| 10 | 20 | 30 | 40 | |
|---|---|---|---|---|
| 1234567890 | 1234567890 | 1234567890 | 1234567890 | |
| CCGGGAAGCT | AGAGTAAGTA | GTTCGCCAGT | TAATAGTTTG | 3680 |
| CGCAACGTTG | TTGCCATTGC | TACAGGCATC | GTGGTGTCAC | 3720 |
| GCTCGTCGTT | TGGTATGGCT | TCATTCAGCT | CCGGTTCCCA | 3760 |
| ACGATCAAGG | CGAGTTACAT | GATCCCCCAT | GTTGTGCAAA | 3800 |
| AAAGCGGTTA | GCTCCTTCGG | TCCTCCGATC | GTTGTCAGAA | 3840 |
| GTAAGTTGGC | CGCAGTGTTA | TCACTCATGG | TTATGGCAGC | 3880 |
| ACTGCATAAT | TCTCTTACTG | TCATGCCATC | CGTAAGATGC | 3920 |
| TTTTCTGTGA | CTGGTGAGTA | CTCAACCAAG | TCATTCTGAG | 3960 |
| AATAGTGTAT | GCGGCGACCG | AGTTGCTCTT | GCCCGGCGTC | 4000 |
| AACACGGGAT | AATACCGCGC | CACATAGCAG | AACTTTAAAA | 4040 |
| GTGCTCATCA | TTGGAAAACG | TTCTTCGGGG | CGAAAACTCT | 4080 |
| CAAGGATCTT | ACCGCTGTTG | AGATCCAGTT | CGATGTAACC | 4120 |
| CACTCGTGCA | CCCAACTGAT | CTTCAGCATC | TTTTACTTTC | 4160 |

FIG. 11H pToxo-P35S

|  10 | 20 | 30 | 40 | |
|---|---|---|---|---|
| 1234567890 | 1234567890 | 1234567890 | 1234567890 | |
| ACCAGCGTTT | CTGGGTGAGC | AAAAACAGGA | AGGCAAAATG | 4200 |
| CCGCAAAAAA | GGGAATAAGG | GCGACACGGA | AATGTTGAAT | 4240 |
| ACTCATACTC | TTCCTTTTTC | AATATTATTG | AAGCATTTAT | 4280 |
| CAGGGTTATT | GTCTCATGAG | CGGATACATA | TTTGAATGTA | 4320 |
| TTTAGAAAAA | TAAACAAATA | GGGGTTCCGC | GCACATTTCC | 4360 |
| CCGAAAAGTG | CCACCTGACG | TCTAAGAAAC | CATTATTATC | 4400 |
| ATGACATTAA | CCTATAAAAA | TAGGCGTATC | ACGAGGCCCT | 4440 |
| TTCGTCTTCA | A | | | 4451 |

FIG. 11I pToxo-P66g

|  | 10 | 20 | 30 | 40 |  |
|---|---|---|---|---|---|
|  | 1234567890 | 1234567890 | 1234567890 | 1234567890 |  |
|  | GAATTAATTC | CCATTAATGT | GAGTTAGCTC | ACTCATTAGG | 40 |
|  | CACCCCAGGC | TTTACACTTT | ATGTTCCGGC | TCGTATTTTG | 80 |
|  | TGTGGAATTG | TGAGCGGATA | ACAATTGGGC | ATCCAGTAAG | 120 |
|  | GAGGTTTAAA | TGAGTTTTGT | GGTCATTATT | CCCGCGCGCT | 160 |
|  |          M | etSerPheVa | lValIleIle | ProAlaArgT |  |
|  | ACGCGACGTC | GCGTCTGCCC | GGTAAACCAT | TGGTTGATAT | 200 |
|  | yrAlaThrSe | rArgLeuPro | GlyLysProL | euValAspIl |  |
|  | TAACGGCAAA | CCCATGATTG | TTCATGTTCT | TGAACGCGCG | 240 |
|  | eAsnGlyLys | ProMetIleV | alHisValLe | uGluArgAla |  |
|  | CGTGAATCAG | GTGCCGAGCG | CATCATCGTG | GCAACCGATC | 280 |
|  | ArgGluSerG | lyAlaGluAr | gIleIleVal | AlaThrAspH |  |
|  | ATGAGGATGT | TGCCCGCGCC | GTTGAAGCCG | CTGGCGGTGA | 320 |
|  | isGluAspVa | lAlaArgAla | ValGluAlaA | laGlyGlyGl |  |
|  | AGTATGTATG | ACGCGCGCCG | ATCATCAGTC | AGGAACAGAA | 360 |
|  | uValCysMet | ThrArgAlaA | spHisGlnSe | rGlyThrGlu |  |
|  | CGTCTGGCGG | AAGTTGTCGA | AAAATGCGCA | TTCAGCGACG | 400 |
|  | ArgLeuAlaG | luValValGl | uLysCysAla | PheSerAspA |  |
|  | ACACGGTGAT | CGTTAATGTG | CAGGGTGATG | AACCGATGAT | 440 |
|  | spThrValIl | eValAsnVal | GlnGlyAspG | luProMetIl |  |
|  | CCCTGCGACA | ATCATTCGTC | AGGTTGCTGA | TAACCTCGCT | 480 |
|  | eProAlaThr | IleIleArgG | lnValAlaAs | pAsnLeuAla |  |
|  | CAGCGTCAGG | TGGGTATGAC | GACTCTGGCG | GTGCCAATCC | 520 |
|  | GlnArgGlnV | alGlyMetTh | rThrLeuAla | ValProIleH |  |

FIG. 13A pToxo-P66g

```
          10          20          30          40
  1234567890  1234567890  1234567890  1234567890
  ACAATGCGGA  AGAAGCGTTT  AACCCGAATG  CGGTGAAAGT      560
  isAsnAlaGl  uGluAlaPhe  AsnProAsnA  laValLysVa

GGTTCTCGAC  GCTGAAGGGT  ATGCACTGTA  CTTCTCTCGC      600
  lValLeuAsp  AlaGluGlyT  yrAlaLeuTy  rPheSerArg

GCCACCATTC  CTTGGGATCG  TGATCGTTTT  GCAGAAGGCC      640
  AlaThrIleP  roTrpAspAr  gAspArgPhe  AlaGluGlyL

TTATGAGCCA  CAATGGAGTC  CCCGCTTATC  CATCGTATGC      680
  euMetSerHi  sAsnGlyVal  ProAlaTyrP  roSerTyrAl

ACAGGTATCG  CTCTCTTCCA  ACGGCGAGCC  ACGGCACAGG      720
  aGlnValSer  LeuSerSerA  snGlyGluPr  oArgHisArg

GGCATACGCG  GCAGCTTCCT  CATGTCCGTA  AAGCCACACG      760
  GlyIleArgG  lySerPheLe  uMetSerVal  LysProHisA

CAAACGCTGA  TGACTTCGCC  TCCGACGACA  ACTACGAACC      800
  laAsnAlaAs  pAspPheAla  SerAspAspA  snTyrGluPr

GCTGCCGAGT  TTCGTGGAAG  CTCCTGTCAG  AGGCCCGGAC      840
  oLeuProSer  PheValGluA  laProValAr  gGlyProAsp

CAAGTCCCTG  CCAGAGGAGA  AGCTGCTCTT  GTCACAGAGG      880
  GlnValProA  laArgGlyGl  uAlaAlaLeu  ValThrGluG

AGACTCCAGC  GCAACAGCCG  GCGGTGGCTC  TAGGCAGTGC      920
  luThrProAl  aGlnGlnPro  AlaValAlaL  euGlySerAl

AGAAGGGGAG  GGGACCTCCA  CTACTGAATC  CGCCTCCGAA      960
  aGluGlyGlu  GlyThrSerT  hrThrGluSe  rAlaSerGlu

AATTCTGAAG  ATGATGACAC  GTTTCACGAT  GCCCTCCAAG     1000
  AsnSerGluA  spAspAspTh  rPheHisAsp  AlaLeuGlnG

AGCTTCCAGA  GGATGGCCTC  GAAGTGCGCC  CACCAAATGC     1040
  luLeuProGl  uAspGlyLeu  GluValArgP  roProAsnAl
```

FIG. 13B pToxo-P66g

|  10        |  20        |  30        |  40        |      |
|------------|------------|------------|------------|------|
| 1234567890 | 1234567890 | 1234567890 | 1234567890 |      |
| ACAGGAGCTG | CCCCCACCAA | ATGTACAGGA | GCTGCCCCCA | 1080 |
| aGlnGluLeu | ProProProA | snValGlnGl | uLeuProPro |      |
| CCAAATGTAC | AGGAGCTGCC | CCCACCAACT | GAACAGGAGC | 1120 |
| ProAsnValG | lnGluLeuPr | oProProThr | GluGlnGluL |      |
| TGCCCCCACC | AACTGAACAG | GAGCTGCCCC | CACCAACTGA | 1160 |
| euProProPr | oThrGluGln | GluLeuProP | roProThrGl |      |
| ACAGGAGCTG | CCCCCACCAA | CTGAACAGGA | GCTACCCCCA | 1200 |
| uGlnGluLeu | ProProProT | hrGluGlnGl | uLeuProPro |      |
| TCAACTGAAC | AGGAGCTGCC | CCCACCAGTG | GGCGAAGGTC | 1240 |
| SerThrGluG | lnGluLeuPr | oProProVal | GlyGluGlyG |      |
| AACGTCTGCA | AGTCCCTGGG | GAACATGGGC | CACAGGGGCC | 1280 |
| lnArgLeuGl | nValProGly | GluHisGlyP | roGlnGlyPr |      |
| CCCATACGAT | GATCAGCAGC | TGCTTTTAGA | GCCTACGGAA | 1320 |
| oProTyrAsp | AspGlnGlnL | euLeuLeuGl | uProThrGlu |      |
| GAGCAACAGG | AGGGCCCTCA | GGAGCCGCTG | CCACCGCCGC | 1360 |
| GluGlnGlnG | luGlyProGl | nGluProLeu | ProProProP |      |
| CGCCCCCGAC | TCGGGGCGAA | CAACCCGAAG | GACAGCAGCC | 1400 |
| roProProTh | rArgGlyGlu | GlnProGluG | lyGlnGlnPr |      |
| GCAGGGACCA | GTTCGTCAAA | ATTTTTTTCG | TCGGGCGTTG | 1440 |
| oGlnGlyPro | ValArgGlnA | snPhePheAr | gArgAlaLeu |      |
| GGGGCCGCAA | GAAGCCGATT | CGGAGGTGCA | CGACGCCATG | 1480 |
| GlyAlaAlaA | rgSerArgPh | eGlyGlyAla | ArgArgHisV |      |
| TCAGTGGGGT | GTTCCGAAGA | GTCAGAGGTG | GTTTGAACCG | 1520 |
| alSerGlyVa | lPheArgArg | ValArgGlyG | lyLeuAsnAr |      |
| TATAGTAGGT | GGAGTGAGGA | GTGGTTTCAG | GCGTGCAAGA | 1560 |
| gIleValGly | GlyValArgS | erGlyPheAr | gArgAlaArg |      |

FIG. 13C pToxo-P66g

|  |  |  |  |  |
|---|---|---|---|---|
| 10 | 20 | 30 | 40 | |
| 1234567890 | 1234567890 | 1234567890 | 1234567890 | |
| GAAGGTGTCG | TTGGGGGAGT | CCGTCGTTTA | ACAAGTGGTG | 1600 |
| GluGlyValV | alGlyGlyVa | lArgArgLeu | ThrSerGlyA | |
| CCAGTCTGGG | TCTCCGTCGT | GTAGGAGAAG | GTTTACGTAG | 1640 |
| laSerLeuGl | yLeuArgArg | ValGlyGluG | lyLeuArgAr | |
| GAGTTTCTAT | CGTGTAAGAG | GAGCTGTCAG | TAGCGGTCGT | 1680 |
| gSerPheTyr | ArgValArgG | lyAlaValSe | rSerGlyArg | |
| AGGCGTGCAG | CAGATGGTGC | CAGCAATGTA | AGAGAAAGAT | 1720 |
| ArgArgAlaA | laAspGlyAl | aSerAsnVal | ArgGluArgP | |
| TCGTTGCCGC | AGGCGGGAGA | GTCAGAGACG | CTTTCGGCGC | 1760 |
| heValAlaAl | aGlyGlyArg | ValArgAspA | laPheGlyAl | |
| GGGATTGACG | CGCCTCCGCA | GGCGCGGCAG | AACTAATGGC | 1800 |
| aGlyLeuThr | ArgLeuArgA | rgArgGlyAr | gThrAsnGly | |
| GAGGAGGGCA | GGCCCCTACT | GGGCGAAGGA | AGAGAGCAGG | 1840 |
| GluGluGlyA | rgProLeuLe | uGlyGluGly | ArgGluGlnA | |
| ATGATGGATC | GCAAACGCGT | CTTGAAACCG | TTGGCGATAA | 1880 |
| spAspGlySe | rGlnThrArg | LeuGluThrV | alGlyAspAs | |
| CTTCCTGCGT | CATCTTGGTA | TTTATGGCTA | CCGTGCAGGC | 1920 |
| nPheLeuArg | HisLeuGlyI | leTyrGlyTy | rArgAlaGly | |
| TTTATCCGTC | GTTACGTCAA | CTGGCAGCCA | AGTCCGTTAG | 1960 |
| PheIleArgA | rgTyrValAs | nTrpGlnPro | SerProLeuG | |
| AACACATCGA | AATGTTAGAG | CAGCTTCGTG | TTCTGTGGTA | 2000 |
| luHisIleGl | uMetLeuGlu | GlnLeuArgV | alLeuTrpTy | |
| CGGCGAAAAA | ATCCATGTTG | CTGTTGCTCA | GGAAGTTCCT | 2040 |
| rGlyGluLys | IleHisValA | laValAlaGl | nGluValPro | |
| GGCACAGGTG | TGGATACCCC | TGAAGATCTC | GACCCGTCGA | 2080 |
| GlyThrGlyV | alAspThrPr | oGluAspLeu | AspProSerT | |

FIG. 13D pToxo-P66g

|  10  |  20  |  30  |  40  | |
|------|------|------|------|---|
| 1234567890 | 1234567890 | 1234567890 | 1234567890 | |
| CGAATTCGAG | CTCGGTACCC | GGGGATCCTC | TAGACTGCAG | 2120 |
| hrAsnSerSe | rSerValPro | GlyAspProL | euAspCysAr | |
| GCATGCTAAG | TAAGTAGATC | TTGAGCGCGT | TCGCGCTGAA | 2160 |
| gHisAlaLys | | | | |
| ATGCGCTAAT | TTCACTTCAC | GACACTTCAG | CCAATTTTGG | 2200 |
| GAGGAGTGTC | GTACCGTTAC | GATTTTCCTC | AATTTTTCTT | 2240 |
| TTCAACAATT | GATCTCATTC | AGGTGACATC | TTTTATATTG | 2280 |
| GCGCTCATTA | TGAAAGCAGT | AGCTTTTATG | AGGGTAATCT | 2320 |
| GAATGGAACA | GCTGCGTGCC | GAATTAAGCC | ATTTACTGGG | 2360 |
| CGAAAAACTC | AGTCGTATTG | AGTGCGTCAA | TGAAAAAGCG | 2400 |
| GATACGGCGT | TGTGGGCTTT | GTATGACAGC | CAGGGAAACC | 2440 |
| CAATGCCGTT | AATGGCAAGA | AGCTTAGCCC | GCCTAATGAG | 2480 |
| CGGGCTTTTT | TTTCGACGCG | AGGCTGGATG | GCCTTCCCCA | 2520 |
| TTATGATTCT | TCTCGCTTCC | GGCGGCATCG | GGATGCCCGC | 2560 |
| GTTGCAGGCC | ATGCTGTCCA | GGCAGGTAGA | TGACGACCAT | 2600 |

FIG. 13E pToxo-P66g

|  10        |  20        |  30        |  40        |      |
| ---------- | ---------- | ---------- | ---------- | ---- |
| 1234567890 | 1234567890 | 1234567890 | 1234567890 |      |
| CAGGGACAGC | TTCAAGGATC | GCTCGCGGCT | CTTACCAGCC | 2640 |
| TAACTTCGAT | CACTGGACCG | CTGATCGTCA | CGGCGATTTA | 2680 |
| TGCCGCCTCG | GCGAGCACAT | GGAACGGGTT | GGCATGGATT | 2720 |
| GTAGGCGCCG | CCCTATACCT | TGTCTGCCTC | CCCGCGTTGC | 2760 |
| GTCGCGGTGC | ATGGAGCCGG | GCCACCTCGA | CCTGAATGGA | 2800 |
| AGCCGGCGGC | ACCTCGCTAA | CGGATTCACC | ACTCCAAGAA | 2840 |
| TTGGAGCCAA | TCAATTCTTG | CGGAGAACTG | TGAATGCGCA | 2880 |
| AACCAACCCT | TGGCAGAACA | TATCCATCGC | GTCCGCCATC | 2920 |
| TCCAGCAGCC | GCACGCGGCG | CATCTCGGGC | AGCGTTGGGT | 2960 |
| CCTGGCCACG | GGTGCGCATG | ATCGTGCTCC | TGTCGTTGAG | 3000 |
| GACCCGGCTA | GGCTGGCGGG | GTTGCCTTAC | TGGTTAGCAG | 3040 |
| AATGAATCAC | CGATACGCGA | GCGAACGTGA | AGCGACTGCT | 3080 |
| GCTGCAAAAC | GTCTGCGACC | TGAGCAACAA | CATGAATGGT | 3120 |

FIG. 13F pToxo-P66g

|  10        |  20        |  30        |  40        |      |
|------------|------------|------------|------------|------|
| 1234567890 | 1234567890 | 1234567890 | 1234567890 |      |
| CTTCGGTTTC | CGTGTTTCGT | AAAGTCTGGA | AACGCGGAAG | 3160 |
| TCAGCGCCCT | GCACCATTAT | GTTCCGGATC | TGCATCGCAG | 3200 |
| GATGCTGCTG | GCTACCCTGT | GGAACACCTA | CATCTGTATT | 3240 |
| AACGAAGCGC | TTCTTCCGCT | TCCTCGCTCA | CTGACTCGCT | 3280 |
| GCGCTCGGTC | GTTCGGCTGC | GGCGAGCGGT | ATCAGCTCAC | 3320 |
| TCAAAGGCGG | TAATACGGTT | ATCCACAGAA | TCAGGGGATA | 3360 |
| ACGCAGGAAA | GAACATGTGA | GCAAAAGGCC | AGCAAAAGGC | 3400 |
| CAGGAACCGT | AAAAAGGCCG | CGTTGCTGGC | GTTTTTCCAT | 3440 |
| AGGCTCCGCC | CCCCTGACGA | GCATCACAAA | AATCGACGCT | 3480 |
| CAAGTCAGAG | GTGGCGAAAC | CCGACAGGAC | TATAAAGATA | 3520 |
| CCAGGCGTTT | CCCCCTGGAA | GCTCCCTCGT | GCGCTCTCCT | 3560 |
| GTTCCGACCC | TGCCGCTTAC | CGGATACCTG | TCCGCCTTTC | 3600 |
| TCCCTTCGGG | AAGCGTGGCG | CTTTCTCAAT | GCTCACGCTG | 3640 |

FIG. 13G pToxo-P66g

|  |  |  |  |  |
|---|---|---|---|---|
| TAGGTATCTC | AGTTCGGTGT | AGGTCGTTCG | CTCCAAGCTG | 3680 |
| GGCTGTGTGC | ACGAACCCCC | CGTTCAGCCC | GACCGCTGCG | 3720 |
| CCTTATCCGG | TAACTATCGT | CTTGAGTCCA | ACCCGGTAAG | 3760 |
| ACACGACTTA | TCGCCACTGG | CAGCAGCCAC | TGGTAACAGG | 3800 |
| ATTAGCAGAG | CGAGGTATGT | AGGCGGTGCT | ACAGAGTTCT | 3840 |
| TGAAGTGGTG | GCCTAACTAC | GGCTACACTA | GAAGGACAGT | 3880 |
| ATTTGGTATC | TGCGCTCTGC | TGAAGCCAGT | TACCTTCGGA | 3920 |
| AAAAGAGTTG | GTAGCTCTTG | ATCCGGCAAA | CAAACCACCG | 3960 |
| CTGGTAGCGG | TGGTTTTTTT | GTTTGCAAGC | AGCAGATTAC | 4000 |
| GCGCAGAAAA | AAAGGATCTC | AAGAAGATCC | TTTGATCTTT | 4040 |
| TCTACGGGGT | CTGACGCTCA | GTGGAACGAA | AACTCACGTT | 4080 |
| AAGGGATTTT | GGTCATGAGA | TTATCAAAAA | GGATCTTCAC | 4120 |
| CTAGATCCTT | TTAAATTAAA | AATGAAGTTT | TAAATCAATC | 4160 |

FIG.13H pToxo-P66g

|   10   |   20   |   30   |   40   |   |
| 1234567890 | 1234567890 | 1234567890 | 1234567890 | |
| TAAAGTATAT | ATCAGTAAAC | TTGGTCTGAC | AGTTACCAAT | 4200 |
| GCTTAATCAG | TGAGGCACCT | ATCTCAGCGA | TCTGTCTATT | 4240 |
| TCGTTCATCC | ATAGTTGCCT | GACTCCCCGT | CGTGTAGATA | 4280 |
| ACTACGATAC | GGGAGGGCTT | ACCATCTGGC | CCCAGTGCTG | 4320 |
| CAATGATACC | GCGAGACCCA | CGCTCACCGG | CTCCAGATTT | 4360 |
| ATCAGCAATA | AACCAGCCAG | CCGGAAGGGC | CGAGCGCAGA | 4400 |
| AGTGGTCCTG | CAACTTTATC | CGCCTCCATC | CAGTCTATTA | 4440 |
| ATTGTTGCCG | GGAAGCTAGA | GTAAGTAGTT | CGCCAGTTAA | 4480 |
| TAGTTTGCGC | AACGTTGTTG | CCATTGCTAC | AGGCATCGTG | 4520 |
| GTGTCACGCT | CGTCGTTTGG | TATGGCTTCA | TTCAGCTCCG | 4560 |
| GTTCCCAACG | ATCAAGGCGA | GTTACATGAT | CCCCCATGTT | 4600 |
| GTGCAAAAAA | GCGGTTAGCT | CCTTCGGTCC | TCCGATCGTT | 4640 |
| GTCAGAAGTA | AGTTGGCCGC | AGTGTTATCA | CTCATGGTTA | 4680 |

FIG.13I pToxo-P66g

| 10 | 20 | 30 | 40 | |
|---|---|---|---|---|
| 1234567890 | 1234567890 | 1234567890 | 1234567890 | |
| TGGCAGCACT | GCATAATTCT | CTTACTGTCA | TGCCATCCGT | 4720 |
| AAGATGCTTT | TCTGTGACTG | GTGAGTACTC | AACCAAGTCA | 4760 |
| TTCTGAGAAT | AGTGTATGCG | GCGACCGAGT | TGCTCTTGCC | 4800 |
| CGGCGTCAAC | ACGGGATAAT | ACCGCGCCAC | ATAGCAGAAC | 4840 |
| TTTAAAAGTG | CTCATCATTG | GAAAACGTTC | TTCGGGGCGA | 4880 |
| AAACTCTCAA | GGATCTTACC | GCTGTTGAGA | TCCAGTTCGA | 4920 |
| TGTAACCCAC | TCGTGCACCC | AACTGATCTT | CAGCATCTTT | 4960 |
| TACTTTCACC | AGCGTTTCTG | GGTGAGCAAA | AACAGGAAGG | 5000 |
| CAAAATGCCG | CAAAAAAGGG | AATAAGGGCG | ACACGGAAAT | 5040 |
| GTTGAATACT | CATACTCTTC | CTTTTTCAAT | ATTATTGAAG | 5080 |
| CATTTATCAG | GGTTATTGTC | TCATGAGCGG | ATACATATTT | 5120 |
| GAATGTATTT | AGAAAAATAA | ACAAATAGGG | GTTCCGCGCA | 5160 |
| CATTTCCCCG | AAAAGTGCCA | CCTGACGTCT | AAGAAACCAT | 5200 |

FIG.13J pToxo-P66g

|  | 10 | 20 | 30 | 40 | |
|---|---|---|---|---|---|
|  | 1234567890 | 1234567890 | 1234567890 | 1234567890 | |
|  | TATTATCATG | ACATTAACCT | ATAAAAATAG | GCGTATCACG | 5240 |
|  | AGGCCCTTTC | GTCTTCAA | | | 5258 |

FIG.13K

SEQUENCE LISTING

<160> NUMBER OF SEQ ID NOS: 55

<210> SEQ ID NO 1
<211> LENGTH: 43
<212> TYPE: DNA
<213> ORGANISM: Toxoplasma gondii

<400> SEQUENCE: 1
cgcagaattc gatgtccacc accgagacgc cagcgcccat tga         43

<210> SEQ ID NO 2
<211> LENGTH: 43
<212> TYPE: DNA
<213> ORGANISM: Toxoplasma gondii

<400> SEQUENCE: 2
cccgggatcc ttacacaaac gtgatcaaca aacctgcgag acc         43

<210> SEQ ID NO 3
<211> LENGTH: 36
<212> TYPE: DNA
<213> ORGANISM: Toxoplasma gondii

<400> SEQUENCE: 3

-continued

```
ggccgaattc gatggccgaa ggcggcgaca accagt                                    36
```

<210> SEQ ID NO 4
<211> LENGTH: 38
<212> TYPE: DNA
<213> ORGANISM: Toxoplasma gondii

<400> SEQUENCE: 4

```
gcccggatcc ttactctctc tctcctgtta ggaaccca                                  38
```

<210> SEQ ID NO 5
<211> LENGTH: 39
<212> TYPE: DNA
<213> ORGANISM: Toxoplasma gondii

<400> SEQUENCE: 5

```
ggcgaattcg atgcaagagg aaatcaaaga agggtgga                                  39
```

<210> SEQ ID NO 6
<211> LENGTH: 33
<212> TYPE: DNA
<213> ORGANISM: Toxoplasma gondii

<400> SEQUENCE: 6

```
cgcactctag atcacctcgg agtcgagccc aac                                       33
```

<210> SEQ ID NO 7
<211> LENGTH: 34
<212> TYPE: DNA
<213> ORGANISM: Toxoplasma gondii

<400> SEQUENCE: 7

```
ggcgaattcg atgagcggta aacctcttga tgag                                      34
```

<210> SEQ ID NO 8
<211> LENGTH: 32
<212> TYPE: DNA
<213> ORGANISM: Toxoplasma gondii

<400> SEQUENCE: 8

```
cgctaggatc cttactgcga aaagtctggg ac                                        32
```

<210> SEQ ID NO 9
<211> LENGTH: 37
<212> TYPE: DNA
<213> ORGANISM: Toxoplasma gondii

<400> SEQUENCE: 9

```
ggcgaattcg atgcttgttg ccaatcaagt tgtcacc                                   37
```

<210> SEQ ID NO 10
<211> LENGTH: 31
<212> TYPE: DNA
<213> ORGANISM: Toxoplasma gondii

<400> SEQUENCE: 10

```
cgctaggatc ctcacgcgac acaagctgcg a                                         31
```

<210> SEQ ID NO 11
<211> LENGTH: 35
<212> TYPE: DNA
<213> ORGANISM: Toxoplasma gondii

<400> SEQUENCE: 11

-continued

```
gacggcgaat tcgatgaacg gtcctttgag ttatc                                35

<210> SEQ ID NO 12
<211> LENGTH: 32
<212> TYPE: DNA
<213> ORGANISM: Toxoplasma gondii

<400> SEQUENCE: 12
cgctaggatc cttaattctg cgtcgttacg gt                                   32

<210> SEQ ID NO 13
<211> LENGTH: 35
<212> TYPE: DNA
<213> ORGANISM: Toxoplasma gondii

<400> SEQUENCE: 13
gacggcgaat tcgatgaacg gtcctttgag ttatc                                35

<210> SEQ ID NO 14
<211> LENGTH: 36
<212> TYPE: DNA
<213> ORGANISM: Toxoplasma gondii

<400> SEQUENCE: 14
cgctaggatc ctcaatggtg aactgccggt atctcc                               36

<210> SEQ ID NO 15
<211> LENGTH: 34
<212> TYPE: DNA
<213> ORGANISM: Toxoplasma gondii

<400> SEQUENCE: 15
ggcgaattcg atgggtgagt gcagctttgg ttct                                 34

<210> SEQ ID NO 16
<211> LENGTH: 34
<212> TYPE: DNA
<213> ORGANISM: Toxoplasma gondii

<400> SEQUENCE: 16
cgcactctag atcactcttt gcgcattctt tcca                                 34

<210> SEQ ID NO 17
<211> LENGTH: 40
<212> TYPE: DNA
<213> ORGANISM: Toxoplasma gondii

<400> SEQUENCE: 17
gcctgaattc gatgcacgta cagcaaggcg ctggcgttgt                           40

<210> SEQ ID NO 18
<211> LENGTH: 42
<212> TYPE: DNA
<213> ORGANISM: Toxoplasma gondii

<400> SEQUENCE: 18
cgctaggatc ctcagaagtc tccatggctt gcaatgggag ga                        42

<210> SEQ ID NO 19
<211> LENGTH: 40
<212> TYPE: DNA
<213> ORGANISM: Toxoplasma gondii
```

```
<400> SEQUENCE: 19
ggcgaattcg atgagccaca atggagtccc cgcttatcca                            40

<210> SEQ ID NO 20
<211> LENGTH: 40
<212> TYPE: DNA
<213> ORGANISM: Toxoplasma gondii

<400> SEQUENCE: 20
cgctaggatc cttattgcga tccatcatcc tgctctcttc                            40

<210> SEQ ID NO 21
<211> LENGTH: 38
<212> TYPE: DNA
<213> ORGANISM: Toxoplasma gondii

<400> SEQUENCE: 21
acccgaattc gatgacagca accgtaggat tgagccaa                              38

<210> SEQ ID NO 22
<211> LENGTH: 34
<212> TYPE: DNA
<213> ORGANISM: Toxoplasma gondii

<400> SEQUENCE: 22
cgctggatcc tcaagctgcc tgttccgcta agat                                  34

<210> SEQ ID NO 23
<211> LENGTH: 1268
<212> TYPE: DNA
<213> ORGANISM: Toxoplasma gondii

<400> SEQUENCE: 23
gaattcggca cgaggcgaac tgggcaaag ccgccgccac cagttcgcta ccgcggccac       60
cgcgtcagat gacgaactga tgagtcgaat ccgaaattct gacttttcg atggtcaagc      120 acccgttgac agtctcagac cgacgaacgc cggtgtcgac tcgaaaggga ccgacgatca     180
cctcaccacc agcatggata aggcatctgt agagagtcag cttccgagaa gagagccatt     240
ggagacggag ccagatgaac aagaagaagt tcatttcagg aagcgaggcg tccgttccga     300
cgctgaagtg actgacgaca acatctacga ggagcacact gatcgtaagg tggttccgag     360
gaagtcggag ggcaagcgaa gcttcaaaga cttgctgaag aagctcgcgc tgccggctgt     420
tggtatgggt gcatcgtatt tgccgctga tagacttgtg ccggaactaa cagaggagca     480
acagagaggc gacgaacccc taaccaccgg ccagaatgtg ggcactgtgt taggcttcgc     540
agcgcttgct gctgccgcag cgttccttgg catgggtctc acgaggacgt accgacattt     600
ttccccacgc aaaacagat cacggcagcc tgcactcgag caagaggtgc ctgaatcagg     660
cgaagatggg gaggatgccc gccagtagga tatgggggct aataaaagtg agtaggagct     720
cgaggacagt gtcccgaacg cgcctgagag gcagacagac acagaagagt gaagaaaaac     780
aacatggtat tacgtgcggt gagtgtttgc tgtcacgtgt tttttgcgcc acaaagacag     840
cttgtgttgt atgcatggga tcgacagttc atggacggcg ctacccagag aggcggcatt     900
tgcgtacacc gtgggtcgtc atgagtaccg ggacatcgtg ttcgtgttta tttgttcatg     960
tcgaagtgca ctaagacacg agacgaaagg gtggttccgc ccctggcagc atcacgtagt    1020
ggtttctttg tcgagaacag cggcagtccg aggccacttg agacaggatg tttgagtgta    1080
tacagacaac gtggtcacag catgaggcaa agctgtctaa gcagccattt gcgcgagcga    1140
```

```
agtcatccat gccgactgtg tgagcctctt tcgtcacttt gaatgagaca gaaactaaga    1200
ctcgcagcag gtctgaatat tgcgaataat ctacttttaa aaccaaaaaa aaaaaaaaaa    1260
aactcgag                                                             1268
```

<210> SEQ ID NO 24
<211> LENGTH: 228
<212> TYPE: PRT
<213> ORGANISM: Toxoplasma gondii

<400> SEQUENCE: 24

```
Asn Ser Ala Arg Gly Glu Leu Gly Gln Ser Arg Arg His Gln Phe Ala
 1               5                  10                  15

Thr Ala Ala Thr Ala Ser Asp Asp Glu Leu Met Ser Arg Ile Arg Asn
             20                  25                  30

Ser Asp Phe Phe Asp Gly Gln Ala Pro Val Asp Ser Leu Arg Pro Thr
         35                  40                  45

Asn Ala Gly Val Asp Ser Lys Gly Thr Asp Asp His Leu Thr Thr Ser
     50                  55                  60

Met Asp Lys Ala Ser Val Glu Ser Gln Leu Pro Arg Arg Glu Pro Leu
 65                  70                  75                  80

Glu Thr Glu Pro Asp Glu Gln Glu Glu Val His Phe Arg Lys Arg Gly
                 85                  90                  95

Val Arg Ser Asp Ala Glu Val Thr Asp Asp Asn Ile Tyr Glu Glu His
            100                 105                 110

Thr Asp Arg Lys Val Val Pro Arg Lys Ser Glu Gly Lys Arg Ser Phe
        115                 120                 125

Lys Asp Leu Leu Lys Lys Leu Ala Leu Pro Ala Val Gly Met Gly Ala
    130                 135                 140

Ser Tyr Phe Ala Ala Asp Arg Leu Val Pro Glu Leu Thr Glu Glu Gln
145                 150                 155                 160

Gln Arg Gly Asp Glu Pro Leu Thr Thr Gly Gln Asn Val Gly Thr Val
                165                 170                 175

Leu Gly Phe Ala Ala Leu Ala Ala Ala Ala Phe Leu Gly Met Gly
            180                 185                 190

Leu Thr Arg Thr Tyr Arg His Phe Ser Pro Arg Lys Asn Arg Ser Arg
        195                 200                 205

Gln Pro Ala Leu Glu Gln Glu Val Pro Glu Ser Gly Glu Asp Gly Glu
    210                 215                 220

Asp Ala Arg Gln
225
```

<210> SEQ ID NO 25
<211> LENGTH: 477
<212> TYPE: DNA
<213> ORGANISM: Toxoplasma gondii

<400> SEQUENCE: 25

```
agaccccgcc accgcccgtg acgaaccacg aaccgcggcg aacggcgagc tcaccgggtt     60
ttcagagacg cgcgagatcc ctgatttcgt ttaccattga cgcccgccgc cgtcgacgtc    120
tttggaacgt gtttcacgtt tgagttgcac tgttactttc ttcggattac attcttccac    180
taaaagctgg ttttgtccag tatccattcg tcgctaccgt tgcgcagtca cgttgaattt    240
tgcagcggca aaacatcttg tgtaaaattc gagttttgtt gatgattgaa gtaccctata    300
ttggggcttg ctaacgtttt gtattaaaag ggattactgc ggcgtctcat ttccaaaatg    360
```

-continued

```
gcccgacacg caatttttc cgcgctttgt gttttaggcc tggtggcggc ggctttgccc    420
cagttcgcta ccgcggccac cgcgtcagat gacgaactga tgagtcgaat ccgaaat      477
```

<210> SEQ ID NO 26
<211> LENGTH: 1648
<212> TYPE: DNA
<213> ORGANISM: Toxoplasma gondii

<400> SEQUENCE: 26

```
agaccccgcc accgcccgtg acgaaccacg aaccgcggcg aacggcgagc tcaccgggtt    60
ttcagagacg cgcgagatcc ctgatttcgt ttaccattga cgcccgccgc cgtcgacgtc   120
tttggaacgt gtttcacgtt tgagttgcac tgttactttc ttcggattac attcttccac   180
taaaagctgg ttttgtccag tatccattcg tcgctaccgt tgcgcagtca cgttgaattt   240
tgcagcggca aaacatcttg tgtaaaattc gagttttgtt gatgattgaa gtaccctata   300
ttggggcttg ctaacgtttt gtattaaaag ggattactgc ggcgtctcat ttccaaaatg   360
gcccgacacg caatttttc cgcgctttgt gttttaggcc tggtggcggc ggctttgccc   420
cagttcgcta ccgcggccac cgcgtcagat gacgaactga tgagtcgaat ccgaaattct   480 gacttttcg atggtcaagc acccgttgac agtctcagac cgacgaacgc cggtgtcgac   540
tcgaaaggga ccgacgatca cctcaccacc agcatggata aggcatctgt agagagtcag   600
cttccgagaa gagagccatt ggagacggag ccagatgaac aagaagaagt tcatttcagg   660
aagcgaggcg tccgttccga cgctgaagtg actgacgaca acatctacga ggagcacact   720
gatcgtaagg tggttccgag gaagtcggag ggcaagcgaa gcttcaaaga cttgctgaag   780
aagctcgcgc tgccggctgt tggtatgggt gcatcgtatt ttgccgctga tagacttgtg   840
ccggaactaa cagaggagca acagagaggc gacgaacccc taaccaccgg ccagaatgtg   900
ggcactgtgt taggcttcgc agcgcttgct gctgccgcag cgttccttgg catgggtctc   960
acgaggacgt accgacattt tcccccacgc aaaaacagat cacggcagcc tgcactcgag  1020
caagaggtgc ctgaatcagg cgaagatggg gaggatgccc gccagtagga tatggggct   1080 aataaaagtg agtaggagct cgaggacagt gtcccgaacg cgcctgagag cagacagac   1140 acagaagagt gaagaaaaac aacatggtat tacgtgcggt gagtgtttgc tgtcacgtgt  1200
tttttgcgcc acaaagacag cttgtgttgt atgcatggga tcgacagttc atggacggcg  1260
ctacccagag aggcggcatt tgcgtacacc gtgggtcgtc atgagtaccg ggacatcgtg  1320
ttcgtgttta tttgttcatg tcgaagtgca ctaagacacg agacgaaagg gtggttccgc  1380
ccctggcagc atcacgtagt ggtttctttg tcgaaacag cggcagtccg aggccacttg   1440
agacaggatg tttgagtgta tacagacaac gtggtcacag catgaggcaa agctgtctaa  1500
gcagccattt gcgcgagcga agtcatccat gccgactgtg tgagcctctt tcgtcacttt  1560
gaatgagaca gaaactaaga ctcgcagcag gtctgaatat tgcgaataat ctacttttaa  1620
aaccaaaaaa aaaaaaaaaa aactcgag                                      1648
```

<210> SEQ ID NO 27
<211> LENGTH: 236
<212> TYPE: PRT
<213> ORGANISM: Toxoplasma gondii

<400> SEQUENCE: 27

```
Met Ala Arg His Ala Ile Phe Ser Ala Leu Cys Val Leu Gly Leu Val
 1               5                  10                  15
```

```
Ala Ala Ala Leu Pro Gln Phe Ala Thr Ala Thr Ala Ser Asp Asp
            20                  25                  30

Glu Leu Met Ser Arg Ile Arg Asn Ser Asp Phe Phe Asp Gly Gln Ala
         35                  40                  45

Pro Val Asp Ser Leu Arg Pro Thr Asn Ala Gly Val Asp Ser Lys Gly
     50                  55                  60

Thr Asp Asp His Leu Thr Thr Ser Met Asp Lys Ala Ser Val Glu Ser
65                  70                  75                  80

Gln Leu Pro Arg Arg Glu Pro Leu Glu Thr Glu Pro Asp Glu Gln Glu
                 85                  90                  95

Glu Val His Phe Arg Lys Arg Gly Val Arg Ser Asp Ala Glu Val Thr
            100                 105                 110

Asp Asp Asn Ile Tyr Glu Glu His Thr Asp Arg Lys Val Val Pro Arg
            115                 120                 125

Lys Ser Glu Gly Lys Arg Ser Phe Lys Asp Leu Leu Lys Lys Leu Ala
        130                 135                 140

Leu Pro Ala Val Gly Met Gly Ala Ser Tyr Phe Ala Ala Asp Arg Leu
145                 150                 155                 160

Val Pro Glu Leu Thr Glu Glu Gln Gln Arg Gly Asp Glu Pro Leu Thr
                165                 170                 175

Thr Gly Gln Asn Val Gly Thr Val Leu Gly Phe Ala Ala Leu Ala Ala
            180                 185                 190

Ala Ala Ala Phe Leu Gly Met Gly Leu Thr Arg Thr Tyr Arg His Phe
        195                 200                 205

Ser Pro Arg Lys Asn Arg Ser Arg Gln Pro Ala Leu Glu Gln Glu Val
    210                 215                 220

Pro Glu Ser Gly Glu Asp Gly Glu Asp Ala Arg Gln
225                 230                 235

<210> SEQ ID NO 28
<211> LENGTH: 78
<212> TYPE: DNA
<213> ORGANISM: Toxoplasma gondii

<400> SEQUENCE: 28
agatctcgac ccgtcgacga attcgagctc ggtacccggg gatcctctag actgcaggca      60
tgctaagtaa gtagatct                                                   78

<210> SEQ ID NO 29
<211> LENGTH: 78
<212> TYPE: DNA
<213> ORGANISM: Toxoplasma gondii

<400> SEQUENCE: 29
agatctcgac ccatctacca attcgtcttc tgttccgggt gatccgctag actgccgtca      60
cgctaagtaa gtagatct                                                   78

<210> SEQ ID NO 30
<211> LENGTH: 88
<212> TYPE: DNA
<213> ORGANISM: Toxoplasma gondii

<400> SEQUENCE: 30
cctgaagatc tcgacccatc taccaattcg tcttctgttc cgggtgatcc gctagactgc      60
cgtcacgcta agtaagtaga tcttgact                                        88
```

<210> SEQ ID NO 31
<211> LENGTH: 88
<212> TYPE: DNA
<213> ORGANISM: Toxoplasma gondii

<400> SEQUENCE: 31
agtcaagatc tacttactta gcgtgacggc agtctagcgg atcacccgga acagaagacg    60
aattggtaga tgggtcgaga tcttcagg                                      88

<210> SEQ ID NO 32
<211> LENGTH: 40
<212> TYPE: DNA
<213> ORGANISM: Toxoplasma gondii

<400> SEQUENCE: 32
aggcctgaat tcgagctctg ggatccgtct gcagacgcgt                          40

<210> SEQ ID NO 33
<211> LENGTH: 32
<212> TYPE: DNA
<213> ORGANISM: Toxoplasma gondii

<400> SEQUENCE: 33
cctgaattcg agctctggga tccgtctgca ga                                  32

<210> SEQ ID NO 34
<211> LENGTH: 36
<212> TYPE: DNA
<213> ORGANISM: Toxoplasma gondii

<400> SEQUENCE: 34
cgcgtctgca gacggatccc agagctcgaa ttcagg                              36

<210> SEQ ID NO 35
<211> LENGTH: 107
<212> TYPE: DNA
<213> ORGANISM: Toxoplasma gondii

<400> SEQUENCE: 35
acatggatcc gctggcgggc atcctcccca tcttcactta gaattcgatg gcccgacacg    60 caatttttc cacttagaat tcgatggccc gacacgcaat tttttcc                  107

<210> SEQ ID NO 36
<211> LENGTH: 35
<212> TYPE: DNA
<213> ORGANISM: Toxoplasma gondii

<400> SEQUENCE: 36
acatggatcc gctggcgggc atcctcccca tcttc                               35

<210> SEQ ID NO 37
<211> LENGTH: 4775
<212> TYPE: DNA
<213> ORGANISM: Toxoplasma gondii

<400> SEQUENCE: 37
gaattaattc ccattaatgt gagttagctc actcattagg caccccaggc tttacacttt    60
atgttccggc tcgtattttg tgtggaattg tgagcggata acaattgggc atccagtaag   120
gaggtttaaa tgagttttgt ggtcattatt cccgcgcgct acgcgacgtc gcgtctgccc   180
ggtaaaccat tggttgatat taacggcaaa cccatgattg ttcatgttct tgaacgcgcg   240

```
cgtgaatcag gtgccgagcg catcatcgtg caaccgatc atgaggatgt tgcccgcgcc     300
gttgaagccg ctggcggtga agtatgtatg acgcgcgccg atcatcagtc aggaacagaa    360
cgtctggcgg aagttgtcga aaaatgcgca ttcagcgacg cacggtgat cgttaatgtg     420
cagggtgatg aaccgatgat ccctgcgaca atcattcgtc aggttgctga taacctcgct    480
cagcgtcagg tgggtatgac gactctggcg gtgccaatcc acaatgcgga agaagcgttt    540
aacccgaatg cggtgaaagt ggttctcgac gctgaagggt atgcactgta cttctctcgc    600
gccaccattc cttgggatcg tgatcgtttt gcagaaggc tgaattcgat ggcccgacac     660
gcaattttttt ccgcgctttg tgttttaggc ctggtggcgg cggctttgcc ccagttcgct   720
accgcggcca ccgcgtcaga tgacgaactg atgagtcgaa tccgaaattc tgacttttc    780
gatggtcaag cacccgttga cagtctcaga ccgacgaacg ccggtgtcga ctcgaaaggg   840
accgacgatc acctcaccac cagcatggat aaggcatctg tagagagtca gcttccgaga   900
agagagccat ggagacgga gccagatgaa caagaagaag ttcatttcag gaagcgaggc    960
gtccgttccg acgctgaagt gactgacgac aacatctacg aggagcacac tgatcgtaag  1020
gtggttccga ggaagtcgga gggcaagcga agcttcaaag acttgctgaa gaagctcgcg  1080
ctgccggctg ttggtatggg tgcatcgtat tttgccgctg atagacttgt gccggaacta  1140
acagaggagc aacagagagg cgacgaaccc ctaaccaccg gccagaatgt gggcactgtg  1200
ttaggcttcg cagcgcttgc tgctgccgca gcgttccttg gcatgggtct cacgaggacg  1260
taccgacatt tttcccccacg caaaaacaga tcacggcagc ctgcactcga gcaagaggtg  1320
cctgaatcag gcgaagatgg ggaggatgcc cgccagcgga tccgtctgca gacgcgtctt  1380
gaaaccgttg gcgataactt cctgcgtcat cttggtattt atggctaccg tgcaggcttt  1440
atccgtcgtt acgtcaactg gcagccaagt ccgttagaac acatcgaaat gttagagcag  1500
cttcgtgttc tgtggtacgg cgaaaaaatc catgttgctg ttgctcagga agttcctggc  1560
acaggtgtgg ataccctga agatctcgac ccatctacca attcgtcttc tgttccgggt  1620
gatccgctag actgccgtca cgctaagtaa gtagatcttg agcgcgttcg cgctgaaatg  1680
cgctaatttc acttcacgac acttcagcca atttttgggag gagtgtcgta ccgttacgat  1740
tttcctcaat ttttctttc aacaattgat ctcattcagg tgacatcttt tatattggcg   1800
ctcattatga aagcagtagc ttttatgagg gtaatctgaa tggaacagct gcgtgccgaa  1860
ttaagccatt tactgggcga aaaactcagt cgtattgagt gcgtcaatga aaagcggat  1920
acggcgttgt gggctttgta tgacagccag ggaaacccaa tgccgttaat ggcaagaagc  1980
ttagcccgcc taatgagcgg gctttttttt cgacgcgagg ctggatggcc ttccccatta  2040
tgattcttct cgcttccggc ggcatcggga tgcccgcgtt gcaggccatg ctgtccaggc  2100
aggtagatga cgaccatcag ggacagcttc aaggatcgct cgcggctctt accagcctaa  2160
cttcgatcac tggaccgctg atcgtcacgg cgatttatgc cgcctcggcg agcacatgga  2220
acgggttggc atggattgta ggcgccgccc tataccttgt ctgcctcccc gcgttgcgtc  2280
gcggtgcatg gagccgggcc acctcgacct gaatggaagc cggcggcacc tcgctaacgg  2340
attcaccact ccaagaattg gagccaatca attcttgcgg agaactgtga atgcgcaaac  2400
caacccttgg cagaacatat ccatcgcgtc cgccatctcc agcagccgca gcgggcgcat  2460
ctcgggcagc gttgggtcct ggccacgggt gcgcatgatc gtgctcctgt cgttgaggac  2520
ccggctaggc tggcggggtt gccttactgg ttagcagaat gaatcaccga tacgcgagcg  2580
```

-continued

```
aacgtgaagc gactgctgct gcaaaacgtc tgcgacctga gcaacaacat gaatggtctt    2640
cggtttccgt gtttcgtaaa gtctggaaac gcggaagtca gcgccctgca ccattatgtt    2700
ccggatctgc atcgcaggat gctgctggct accctgtgga acacctacat ctgtattaac    2760
gaagcgcttc ttccgcttcc tcgctcactg actcgctgcg ctcggtcgtt cggctgcggc    2820
gagcggtatc agctcactca aaggcggtaa tacggttatc cacagaatca ggggataacg    2880
caggaaagaa catgtgagca aaaggccagc aaaaggccag gaaccgtaaa aaggccgcgt    2940
tgctggcgtt tttccatagg ctccgccccc ctgacgagca tcacaaaaat cgacgctcaa    3000
gtcagaggtg gcgaaacccg acaggactat aaagatacca ggcgtttccc cctggaagct    3060
ccctcgtgcg ctctcctgtt ccgaccctgc cgcttaccgg atacctgtcc gcctttctcc    3120
cttcgggaag cgtggcgctt tctcaatgct cacgctgtag gtatctcagt tcggtgtagg    3180
tcgttcgctc caagctgggc tgtgtgcacg aaccccccgt tcagcccgac cgctgcgcct    3240
tatccggtaa ctatcgtctt gagtccaacc cggtaagaca cgacttatcg ccactggcag    3300
cagccactgg taacaggatt agcagagcga ggtatgtagg cggtgctaca gagttcttga    3360
agtggtggcc taactacggc tacactagaa ggacagtatt tggtatctgc gctctgctga    3420
agccagttac cttcggaaaa agagttggta gctcttgatc cggcaaacaa accaccgctg    3480
gtagcggtgg ttttttttgtt tgcaagcagc agattacgcg cagaaaaaaa ggatctcaag    3540
aagatccttt gatcttttct acggggtctg acgctcagtg gaacgaaaac tcacgttaag    3600
ggattttggt catgagatta tcaaaaagga tcttcaccta gatccttttta aattaaaaat    3660 gaagttttaa atcaatctaa agtatatatg agtaaacttg gtctgacagt taccaatgct    3720
taatcagtga ggcacctatc tcagcgatct gtctatttcg ttcatccata gttgcctgac    3780
tccccgtcgt gtagataact acgatacggg agggcttacc atctggcccc agtgctgcaa    3840
tgataccgcg agacccacgc tcaccggctc cagatttatc agcaataaac cagccagccg    3900
gaagggccga gcgcagaagt ggtcctgcaa ctttatccgc ctccatccag tctattaatt    3960
gttgccggga agctagagta agtagttcgc cagttaatag tttgcgcaac gttgttgcca    4020
ttgctacagg catcgtggtg tcacgctcgt cgtttggtat ggcttcattc agctccggtt    4080
cccaacgatc aaggcgagtt acatgatccc ccatgttgtg caaaaaagcg gttagctcct    4140
tcggtcctcc gatcgttgtc agaagtaagt tggccgcagt gttatcactc atggttatgg    4200
cagcactgca taattctctt actgtcatgc catccgtaag atgcttttct gtgactggtg    4260
agtactcaac caagtcattc tgagaatagt gtatgcggcg accgagttgc tcttgcccgg    4320
cgtcaacacg ggataatacc gcgccacata gcagaacttt aaaagtgctc atcattggaa    4380
aacgttcttc ggggcgaaaa ctctcaagga tcttaccgct gttgagatcc agttcgatgt    4440
aacccactcg tgcacccaac tgatcttcag catcttttac tttcaccagc gtttctgggt    4500
gagcaaaaac aggaaggcaa atgccgcaaa aaagggaat aagggcgaca cggaaatgtt    4560
gaatactcat actcttcctt tttcaatatt attgaagcat ttatcagggt tattgtctca    4620
tgagcggata catatttgaa tgtatttaga aaaataaaca aataggggtt ccgcgcacat    4680
ttccccgaaa agtgccacct gacgtctaag aaaccattat tatcatgaca ttaacctata    4740
aaaataggcg tatcacgagg ccctttcgtc ttcaa                               4775
```

<210> SEQ ID NO 38
<211> LENGTH: 36
<212> TYPE: DNA
<213> ORGANISM: Toxoplasma gondii

<400> SEQUENCE: 38
tcctaggcct taattcgatg cttgttgcca atcaag 36

<210> SEQ ID NO 39
<211> LENGTH: 32
<212> TYPE: DNA
<213> ORGANISM: Toxoplasma gondii

<400> SEQUENCE: 39
acatacgcgt cgcgacacaa gctgcgatag ag 32

<210> SEQ ID NO 40
<211> LENGTH: 4910
<212> TYPE: DNA
<213> ORGANISM: Toxoplasma gondii

<400> SEQUENCE: 40

```
gaattaattc ccattaatgt gagttagctc actcattagg cacccccaggc tttacacttt    60
atgttccggc tcgtatttg tgtggaattg tgagcggata acaattgggc atccagtaag    120
gaggtttaaa tgagttttgt ggtcattatt cccgcgcgct acgcgacgtc gcgtctgccc   180
ggtaaaccat tggttgatat taacggcaaa cccatgattg ttcatgttct tgaacgcgcg   240
cgtgaatcag gtgccgagcg catcatcgtg gcaaccgatc atgaggatgt tgcccgcgcc   300
gttgaagccg ctggcggtga agtatgtatg acgcgcgccg atcatcagtc aggaacagaa   360
cgtctggcgg aagttgtcga aaaatgcgca ttcagcgacg acacggtgat cgttaatgtg   420
cagggtgatg aaccgatgat ccctgcgaca atcattcgtc aggttgctga taacctcgct   480
cagcgtcagg tgggtatgac gactctggcg gtgccaatcc acaatgcgga agaagcgttt   540
aacccgaatg cggtgaaagt ggttctcgac gctgaagggt atgcactgta cttctctcgc   600
gccaccattc cttgggatcg tgatcgtttt gcagaaggcc ttaattcgat gcttgttgcc   660
aatcaagttg tcacctgccc agataaaaaa tcgacagccg cggtcattct cacaccgacg   720
gagaaccact tcactctcaa gtgccctaaa acagcgctca cagagcctcc cactcttgcg   780
tactcaccca acaggcaaat ctgcccagcg ggtactacaa gtagctgtac atcaaaggct   840
gtaacattga gctccttgat tcctgaagca gaagatagct ggtggacggg ggattctgct   900
agtctcgaca cggcaggcat caaactcaca gttccaatcg agaagttccc cgtgacaacg   960
cagacgtttg tggtcggttg catcaaggga gacgacgcac agagttgtat ggtcacggtg   1020
acagtacaag ccagagcctc atcggtcgtc aataatgtcg caaggtgctc ctacggtgca   1080
gacagcactc ttggtcctgt caagttgtct gcggaaggac ccactacaat gaccctcgtg   1140
tgcgggaaag atggagtcaa agttcctcaa gacaacaatc agtactgttc cgggacgacg   1200
ctgactggtt gcaacgagaa atcgttcaaa gatattttgc caaaattaac tgagaacccg   1260
tggcagggta acgcttcgag tgataagggt gccacgctaa cgatcaagaa ggaagcattt   1320
ccagccgagt caaaaagcgt cattattgga tgcagagggg gatcgcctga gaagcatcac   1380
tgtaccgtga aactggagtt tgccggggct gcagggtcag caaaatcggc tgcgggaaca   1440
gccagtcacg tttccatttt tgccatgggt atcggactta ttggctctat cgcagcttgt   1500
gtcgcgacgc gtcttgaaac cgttggcgat aacttcctgc gtcatcttgg tatttatggc   1560
taccgtgcag gctttatccg tcgttacgtc aactggcagc caagtccgtt agaacacatc   1620
gaaatgttag agcagcttcg tgttctgtgg tacggcgaaa aaatccatgt tgctgttgct   1680
```

```
caggaagttc ctggcacagg tgtggatacc cctgaagatc tcgacccgtc gacgaattcg    1740
agctcggtac ccgggatcc tctagactgc aggcatgcta agtaagtaga tcttgagcgc     1800
gttcgcgctg aaatgcgcta atttcacttc acgacacttc agccaatttt gggaggagtg    1860
tcgtaccgtt acgattttcc tcaattttc ttttcaacaa ttgatctcat tcaggtgaca     1920 tctttatat tggcgctcat tatgaaagca gtagcttta tgagggtaat ctgaatggaa      1980
cagctgcgtg ccgaattaag ccatttactg ggcgaaaaac tcagtcgtat tgagtgcgtc    2040
aatgaaaaag cggatacggc gttgtgggct ttgtatgaca gccagggaaa cccaatgccg    2100
ttaatggcaa gaagcttagc ccgcctaatg agcgggcttt tttttcgacg cgaggctgga    2160
tggccttccc cattatgatt cttctcgctt ccggcggcat cgggatgccc gcgttgcagg    2220
ccatgctgtc caggcaggta gatgacgacc atcagggaca gcttcaagga tcgctcgcgg    2280
ctcttaccag cctaacttcg atcactggac cgctgatcgt cacggcgatt tatgccgcct    2340
cggcgagcac atggaacggg ttggcatgga ttgtaggcgc cgccctatac cttgtctgcc    2400
tccccgcgtt gcgtcgcggt gcatggagcc gggccacctc gacctgaatg gaagccggcg    2460
gcacctcgct aacggattca ccactccaag aattggagcc aatcaattct gcggagaac     2520 tgtgaatgcg caaaccaacc cttggcagaa catatccatc gcgtccgcca tctccagcag    2580
ccgcacgcgg cgcatctcgg gcagcgttgg gtcctggcca cgggtgcgca tgatcgtgct    2640
cctgtcgttg aggacccggc taggctggcg gggttgcctt actggttagc agaatgaatc    2700
accgatacgc gagcgaacgt gaagcgactg ctgctgcaaa acgtctgcga cctgagcaac    2760
aacatgaatg gtcttcggtt ccgtgtttc gtaaagtctg gaaacgcgga agtcagcgcc     2820
ctgcaccatt atgttccgga tctgcatcgc aggatgctgc tggctaccct gtgaacacc     2880 tacatctgta ttaacgaagc gcttcttccg cttcctcgct cactgactcg ctgcgctcgg    2940
tcgttcggct gcggcgagcg gtatcagctc actcaaaggc ggtaatacgg ttatccacag    3000
aatcagggga taacgcagga agaacatgt gagcaaaagg ccagcaaaag gccaggaacc     3060
gtaaaaaggc cgcgttgctg gcgttttcc ataggctccg cccccctgac gagcatcaca    3120
aaaatcgacg ctcaagtcag aggtggcgaa acccgacagg actataaaga taccaggcgt    3180
ttccccctgg aagctccctc gtgcgctctc ctgttccgac cctgccgctt accggatacc    3240
tgtccgcctt tctcccttcg ggaagcgtgg cgctttctca atgctcacgc tgtaggtatc    3300
tcagttcggt gtaggtcgtt cgctccaagc tgggctgtgt gcacgaaccc cccgttcagc    3360
ccgaccgctg cgccttatcc ggtaactatc gtcttgagtc aacccggta agacacgact     3420 tatcgccact ggcagcagcc actggtaaca ggattagcag agcgaggtat gtaggcggtg    3480
ctacagagtt cttgaagtgg tggcctaact acggctacac tagaaggaca gtatttggta    3540
tctgcgctct gctgaagcca gttaccttcg aaaaagagt tggtagctct tgatccggca     3600
aacaaaccac cgctggtagc ggtggttttt ttgtttgcaa gcagcagatt acgcgcagaa    3660
aaaaaggatc tcaagaagat cctttgatct tttctacggg gtctgacgct cagtggaacg    3720
aaaactcacg ttaagggatt ttggtcatga gattatcaaa aaggatcttc acctagatcc    3780
ttttaaatta aaaatgaagt tttaaatcaa tctaaagtat atatgagtaa acttggtctg    3840
acagttacca atgcttaatc agtgaggcac ctatctcagc gatctgtcta tttcgttcat    3900
ccatagttgc ctgactcccc gtcgtgtaga taactacgat acgggagggc ttaccatctg    3960
gccccagtgc tgcaatgata ccgcgagacc cacgctcacc ggctccagat ttatcagcaa    4020
taaaccagcc agccggaagg gccgagcgca gaagtggtcc tgcaacttta tccgcctcca    4080
```

```
tccagtctat taattgttgc cgggaagcta gagtaagtag ttcgccagtt aatagtttgc    4140
gcaacgttgt tgccattgct acaggcatcg tggtgtcacg ctcgtcgttt ggtatggctt    4200
cattcagctc cggttcccaa cgatcaaggc gagttacatg atcccccatg ttgtgcaaaa    4260
aagcggttag ctccttcggt cctccgatcg ttgtcagaag taagttggcc gcagtgttat    4320
cactcatggt tatggcagca ctgcataatt ctcttactgt catgccatcc gtaagatgct    4380
tttctgtgac tggtgagtac tcaaccaagt cattctgaga atagtgtatg cggcgaccga    4440
gttgctcttg cccggcgtca acacgggata ataccgcgcc acatagcaga actttaaaag    4500
tgctcatcat tggaaaacgt tcttcggggc gaaaactctc aaggatctta ccgctgttga    4560
gatccagttc gatgtaaccc actcgtgcac ccaactgatc ttcagcatct tttactttca    4620
ccagcgtttc tgggtgagca aaaacaggaa ggcaaaatgc cgcaaaaaag gaataaggg    4680 cgacacggaa atgttgaata ctcatactct tcctttttca atattattga agcatttatc    4740
agggttattg tctcatgagc ggatacatat ttgaatgtat ttagaaaaat aaacaaatag    4800
gggttccgcg cacatttccc cgaaaagtgc cacctgacgt ctaagaaacc attattatca    4860
tgacattaac ctataaaaat aggcgtatca cgaggccctt tcgtcttcaa                4910
```

```
<210> SEQ ID NO 41
<211> LENGTH: 40
<212> TYPE: DNA
<213> ORGANISM: Toxoplasma gondii

<400> SEQUENCE: 41
gagcagaagg ccttatgaac ggtcctttga gttatcatcc                            40

<210> SEQ ID NO 42
<211> LENGTH: 33
<212> TYPE: DNA
<213> ORGANISM: Toxoplasma gondii

<400> SEQUENCE: 42
ttcgctcacg cgtatggtga actgccggta tct                                   33

<210> SEQ ID NO 43
<211> LENGTH: 34
<212> TYPE: DNA
<213> ORGANISM: Toxoplasma gondii

<400> SEQUENCE: 43
gacggagacg cgtcttgaac cgttggcgat aact                                  34

<210> SEQ ID NO 44
<211> LENGTH: 21
<212> TYPE: DNA
<213> ORGANISM: Toxoplasma gondii

<400> SEQUENCE: 44
gcatgcctgc agtctagagg a                                                21

<210> SEQ ID NO 45
<211> LENGTH: 4451
<212> TYPE: DNA
<213> ORGANISM: Toxoplasma gondii

<400> SEQUENCE: 45
gaattaattc ccattaatgt gagttagctc actcattagg cacccccaggc tttacacttt     60
```

-continued

| | |
|---|---|
| atgttccggc tcgtattttg tgtggaattg tgagcggata caattgggc atccagtaag | 120 |
| gaggtttaaa tgagttttgt ggtcattatt cccgcgcgct acgcgtcgac gcgtctgccc | 180 |
| ggtaaaccat tggttgatat aacggcaaa cccatgattg ttcatgttct tgaacgcgcg | 240 |
| cgtgaatcag gtgccgagcg catcatcgtg gcaaccgatc atgaggatgt tgcccgcgcc | 300 |
| gttgaagccg ctggcggtga agtatgtatg acgcgcgccg atcatcagtc aggaacagaa | 360 |
| cgtctggcgg aagttgtcga aaatgcgca ttcagcgacg acacggtgat cgttaatgtg | 420 |
| cagggtgatg aaccgatgat ccctgcgaca atcattcgtc aggttgctga taacctcgct | 480 |
| cagcgtcagg tgggtatgac gactctggcg gtgccaatcc acaatgcgga agaagcgttt | 540 |
| aacccgaatg cggtgaaagt ggttctcgac gctgaagggt atgcactgta cttctctcgc | 600 |
| gccaccattc cttgggatcg tgatcgtttt gcagaaggcc ttatgaacgg tcctttgagt | 660 |
| tatcatccaa gcagttacgg agcgtcgtat ccgaatccga gtaatcctct gcatggaatg | 720 |
| cccaagccag agaacccggt gagaccgcct cctcccggtt tccatccaag cgttattccc | 780 |
| aatcccccgt acccgctggg cactccagcg agcatgccac agccagaggt tccgccactt | 840 |
| cagcatcccc cgccaacggg ttcccctccc gcggccgctc cccagcctcc atatccagtg | 900 |
| ggtactccag taatgccaca gccagagata ccgcctgttc atcggccgcc gcctccgggt | 960 |
| ttccgtcccg aagtggctcc cgtgccccg tatccagtgg gcactccaac gggcatgccc | 1020 |
| cagccggaga taccggcagt tcaccatacg cgtcttgaaa ccgttggcga taacttcctg | 1080 |
| cgtcatcttg gtatttatgg ctaccgtgca ggctttatcc gtcgttacgt caactggcag | 1140 |
| ccaagtccgt tagaacacat cgaaatgtta gagcagcttc gtgttctgtg gtacggcgaa | 1200 |
| aaaatccatg ttgctgttgc tcaggaagtt cctggcacag gtgtggatac ccctgaagat | 1260 |
| ctcgacccgt cgacgaattc gagctcggta cccggggatc tctagactg caggcatgct | 1320 |
| aagtaagtag atcttgagcg cgttcgcgct gaaatgcgct aatttcactt cacgacactt | 1380 |
| cagccaattt tgggaggagt gtcgtaccgt tacgattttc ctcaatttt cttttcaaca | 1440 |
| attgatctca ttcaggtgac atcttttata ttggcgctca ttatgaaagc agtagctttt | 1500 |
| atgagggtaa tctgaatgga acagctgcgt gccgaattaa gccatttact gggcgaaaaa | 1560 |
| ctcagtcgta ttgagtgcgt caatgaaaaa gcggatacgg cgttgtgggc tttgtatgac | 1620 |
| agccagggaa acccaatgcc gttaatggca agaagcttag cccgcctaat gagcgggctt | 1680 |
| ttttttcgac gcgaggctgg atggccttcc ccattatgat tcttctcgct tccggcggca | 1740 |
| tcgggatgcc cgcgttgcag gccatgctgt ccaggcaggt agatgacgac catcagggac | 1800 |
| agcttcaagg atcgctcgcg gctcttacca gcctaacttc gatcactgga ccgctgatcg | 1860 |
| tcacggcgat ttatgccgcc tcggcgagca catggaacgg gttggcatgg attgtaggcg | 1920 |
| ccgccctata ccttgtctgc ctccccgcgt tgcgtcgcgg tgcatggagc cgggccacct | 1980 |
| cgacctgaat ggaagccggc ggcacctcgc taacggattc accactccaa gaattggagc | 2040 |
| caatcaattc ttgcggagaa ctgtgaatgc gcaaaccaac ccttggcaga acatatccat | 2100 |
| cgcgtccgcc atctccagca gccgcacgcg gcgcatctcg ggcagcgttg gtcctggcc | 2160 |
| acgggtgcgc atgatcgtgc tcctgtcgtt gaggacccgg ctaggctggc ggggttgcct | 2220 |
| tactggttag cagaatgaat caccgatacg cgagcgaacg tgaagcgact gctgctgcaa | 2280 |
| aacgtctgcg acctgagcaa caacatgaat ggtcttcggt ttccgtgttt cgtaaagtct | 2340 |
| ggaaacgcgg aagtcagcgc cctgcaccat tatgttccgg atctgcatcg caggatgctg | 2400 |
| ctggctaccc tgtggaacac ctacatctgt attaacgaag cgcttcttcc gcttcctcgc | 2460 |

```
tcactgactc gctgcgctcg gtcgttcggc tgcggcgagc ggtatcagct cactcaaagg    2520
cggtaatacg gttatccaca gaatcagggg ataacgcagg aaagaacatg tgagcaaaag    2580
gccagcaaaa ggccaggaac cgtaaaaagg ccgcgttgct ggcgtttttc cataggctcc    2640
gcccccctga cgagcatcac aaaaatcgac gctcaagtca gaggtggcga acccgacag     2700 gactataaag ataccaggcg tttccccctg gaagctccct cgtgcgctct cctgttccga    2760
ccctgccgct taccggatac ctgtccgcct ttctcccttc gggaagcgtg gcgctttctc    2820
aatgctcacg ctgtaggtat ctcagttcgg tgtaggtcgt tcgctccaag ctgggctgtg    2880
tgcacgaacc ccccgttcag cccgaccgct gcgccttatc cggtaactat cgtcttgagt    2940
ccaacccggt aagacacgac ttatcgccac tggcagcagc cactggtaac aggattagca    3000
gagcgaggta tgtaggcggt gctacagagt tcttgaagtg gtggcctaac tacggctaca    3060
ctagaaggac agtatttggt atctgcgctc tgctgaagcc agttaccttc ggaaaaagag    3120
ttggtagctc ttgatccggc aaacaaacca ccgctggtag cggtggtttt tttgtttgca    3180
agcagcagat tacgcgcaga aaaaaggat ctcaagaaga cctttgatc ttttctacgg      3240 ggtctgacgc tcagtggaac gaaaactcac gttaagggat tttggtcatg agattatcaa    3300
aaaggatctt cacctagatc cttttaaatt aaaaatgaag ttttaaatca atctaaagta    3360
tatatgagta aacttggtct gacagttacc aatgcttaat cagtgaggca cctatctcag    3420
cgatctgtct atttcgttca tccatagttg cctgactccc cgtcgtgtag ataactacga    3480
tacgggaggg cttaccatct ggccccagtg ctgcaatgat accgcgagac ccacgctcac    3540
cggctccaga tttatcagca ataaaccagc cagccggaag ggccgagcgc agaagtggtc    3600
ctgcaacttt atccgcctcc atccagtcta ttaattgttg ccgggaagct agagtaagta    3660
gttcgccagt taatagtttg cgcaacgttg ttgccattgc tacaggcatc gtggtgtcac    3720
gctcgtcgtt tggtatggct tcattcagct ccggttccca acgatcaagg cgagttacat    3780
gatcccccat gttgtgcaaa aaagcggtta gctccttcgg tcctccgatc gttgtcagaa    3840
gtaagttggc cgcagtgtta tcactcatgg ttatggcagc actgcataat tctcttactg    3900
tcatgccatc cgtaagatgc ttttctgtga ctggtgagta ctcaaccaag tcattctgag    3960
aatagtgtat gcggcgaccg agttgctctt gcccggcgtc aacacgggat aataccgcgc    4020
cacatagcag aactttaaaa gtgctcatca ttggaaaacg ttcttcgggg cgaaaactct    4080
caaggatctt accgctgttg agatccagtt cgatgtaacc cactcgtgca cccaactgat    4140
cttcagcatc ttttactttc accagcgttt ctgggtgagc aaaaacagga aggcaaaatg    4200
ccgcaaaaaa gggaataagg gcgacacgga aatgttgaat actcatactc ttccttttc    4260 aatattattg aagcatttat cagggttatt gtctcatgag cggatacata tttgaatgta    4320
tttagaaaaa taaacaaata ggggttccgc gcacatttcc ccgaaaagtg ccacctgacg    4380
tctaagaaac cattattatc atgacattaa cctataaaaa taggcgtatc acgaggccct    4440
ttcgtcttca a                                                         4451

<210> SEQ ID NO 46
<211> LENGTH: 41
<212> TYPE: DNA
<213> ORGANISM: Toxoplasma gondii

<400> SEQUENCE: 46
atattaggcc ttatgagcca caatggagtc cccgcttatc c                         41
```

<210> SEQ ID NO 47
<211> LENGTH: 38
<212> TYPE: DNA
<213> ORGANISM: Toxoplasma gondii

<400> SEQUENCE: 47
cagtgtacgc gtttgcgatc catcatcctg ctctcttc                            38

<210> SEQ ID NO 48
<211> LENGTH: 5258
<212> TYPE: DNA
<213> ORGANISM: Toxoplasma gondii

<400> SEQUENCE: 48
gaattaattc ccattaatgt gagttagctc actcattagg caccccaggc tttacacttt     60
atgttccggc tcgtattttg tgtggaattg tgagcggata acaattgggc atccagtaag    120
gaggtttaaa tgagttttgt ggtcattatt cccgcgcgct acgcgacgtc gcgtctgccc    180
ggtaaaccat tggttgatat taacggcaaa cccatgattg ttcatgttct gaacgcgcg    240 cgtgaatcag gtgccgagcg catcatcgtg gcaaccgatc atgaggatgt tgcccgcgcc    300
gttgaagccg ctggcggtga agtatgtatg acgcgcgccg atcatcagtc aggaacagaa    360
cgtctggcgg aagttgtcga aaaatgcgca ttcagcgacg acacggtgat cgttaatgtg    420
cagggtgatg aaccgatgat ccctgcgaca atcattcgtc aggttgctga taacctcgct    480
cagcgtcagg tgggtatgac gactctggcg gtgccaatcc acaatgcgga agaagcgttt    540
aacccgaatg cggtgaaagt ggttctcgac gctgaagggt atgcactgta cttctctcgc    600
gccaccattc cttgggatcg tgatcgtttt gcagaaggcc ttatgagcca caatggagtc    660
cccgcttatc catcgtatgc acaggtatcg ctctcttcca acggcgagcc acggcacagg    720
ggcatacgcg gcagcttcct catgtccgta aagccacacg caaacgctga tgacttcgcc    780
tccgacgaca actacgaacc gctgccgagt ttcgtggaag ctcctgtcag aggcccggac    840
caagtccctg ccagaggaga agctgctctt gtcacagagg agactccagc gcaacagccg    900
gcggtggctc taggcagtgc agaaggggag gggacctcca ctactgaatc cgcctccgaa    960
aattctgaag atgatgacac gtttcacgat gccctccaag agcttccaga ggatggcctc   1020
gaagtgcgcc caccaaatgc acaggagctg cccccaccaa atgtacagga gctgccccca   1080
ccaaatgtac aggagctgcc cccaccaact gaacaggagc tgcccccacc aactgaacag   1140
gagctgcccc caccaactga acaggagctg cccccaccaa ctgaacagga gctaccccca   1200
tcaactgaac aggagctgcc cccaccagtg gcgaaggtc aacgtctgca agtccctggg   1260
gaacatgggc cacaggggcc cccatacgat gatcagcagc tgcttttaga gcctacggaa   1320
gagcaacagg agggccctca ggagccgctg ccaccgccgc cgcccccgac tcggggcgaa   1380
caacccgaag gacagcagcc gcagggacca gttcgtcaaa atttttttcg tcgggcgttg   1440
ggggccgcaa gaagccgatt cggaggtgca cgacgccatg tcagtggggt gttccgaaga   1500
gtcagaggtg gttttgaaccg tatagtaggt ggagtgagga gtggtttcag gcgtgcaaga   1560
gaaggtgtcg ttgggggagt ccgtcgttta caagtggtg ccagtctggg tctccgtcgt   1620
gtaggagaag gtttacgtag gagtttctat cgtgtaagag gagctgtcag tagcggtcgt   1680
aggcgtgcag cagatggtgc cagcaatgta agagaaagat tcgttgccgc aggcgggaga   1740
gtcagagacg cttttcggcgc gggattgacg cgcctccgca ggcgcggcag aactaatggc   1800
gaggagggca ggcccctact gggcgaagga agagagcagg atgatggatc gcaaacgcgt   1860

-continued

```
cttgaaaccg ttggcgataa cttcctgcgt catcttggta tttatggcta ccgtgcaggc    1920
tttatccgtc gttacgtcaa ctggcagcca agtccgttag aacacatcga aatgttagag    1980
cagcttcgtg ttctgtggta cggcgaaaaa atccatgttg ctgttgctca ggaagttcct    2040
ggcacaggtg tggataccCC tgaagatctc gacccgtcga cgaattcgag ctcggtaccc    2100
ggggatcctc tagactgcag gcatgctaag taagtagatc ttgagcgcgt tcgcgctgaa    2160
atgcgctaat ttcacttcac gacacttcag ccaattttgg gaggagtgtc gtaccgttac    2220
gattttcctc aattttctt ttcaacaatt gatctcattc aggtgacatc ttttatattg    2280
gcgctcatta tgaaagcagt agcttttatg agggtaatct gaatggaaca gctgcgtgcc    2340
gaattaagcc atttactggg cgaaaaactc agtcgtattg agtgcgtcaa tgaaaaagcg    2400
gatacggcgt tgtgggcttt gtatgacagc cagggaaacc caatgccgtt aatggcaaga    2460
agcttagccc gcctaatgag cgggcttttt tttcgacgcg aggctggatg gccttcccca    2520
ttatgattct tctcgcttcc ggcggcatcg ggatgcccgc gttgcaggcc atgctgtcca    2580
ggcaggtaga tgacgaccat cagggacagc ttcaaggatc gctcgcggct cttaccagcc    2640
taacttcgat cactggaccg ctgatcgtca cggcgattta tgccgcctcg gcgagcacat    2700
ggaacggggtt ggcatggatt gtaggcgccg ccctatacct tgtctgcctc cccgcgttgc    2760
gtcgcggtgc atggagccgg gccacctcga cctgaatgga agccggcggc acctcgctaa    2820
cggattcacc actccaagaa ttggagccaa tcaattcttg cggagaactg tgaatgcgca    2880
aaccaaccct tggcagaaca tatccatcgc gtccgccatc tccagcagcc gcacgcggcg    2940
catctcgggc agcgttgggt cctggccacg ggtgcgcatg atcgtgctcc tgtcgttgag    3000
gacccggcta ggctggcggg gttgccttac tggttagcag aatgaatcac cgatacgcga    3060
gcgaacgtga agcgactgct gctgcaaaac gtctgcgacc tgagcaacaa catgaatggt    3120
cttcggtttc cgtgtttcgt aaagtctgga aacgcggaag tcagcgccct gcaccattat    3180
gttccggatc tgcatcgcag gatgctgctg gctaccctgt ggaacaccta catctgtatt    3240
aacgaagcgc ttcttccgct tcctcgctca ctgactcgct gcgctcggtc gttcggctgc    3300
ggcgagcggt atcagctcac tcaaaggcgg taatacggtt atccacagaa tcaggggata    3360
acgcaggaaa gaacatgtga gcaaaaggcc agcaaaaggc caggaaccgt aaaaaggccg    3420
cgttgctggc gtttttccat aggctccgcc cccctgacga gcatcacaaa aatcgacgct    3480
caagtcagag gtggcgaaac ccgacaggac tataaagata ccaggcgttt ccccctggaa    3540
gctccctcgt gcgctctcct gttccgaccc tgccgcttac cggatacctg tccgcctttc    3600
tcccttcggg aagcgtggcg ctttctcaat gctcacgctg taggtatctc agttcggtgt    3660
aggtcgttcg ctccaagctg ggctgtgtgc acgaaccccc cgttcagccc gaccgctgcg    3720
ccttatccgg taactatcgt cttgagtcca acccggtaag acacgactta tcgccactgg    3780
cagcagccac tggtaacagg attagcagag cgaggtatgt aggcggtgct acagagttct    3840
tgaagtggtg gcctaactac ggctacacta gaaggacagt atttggtatc tgcgctctgc    3900
tgaagccagt taccttcgga aaaagagttg gtagctcttg atccggcaaa caaaccaccg    3960
ctggtagcgg tggtttttttt gtttgcaagc agcagattac gcgcagaaaa aaggatctc    4020
aagaagatcc tttgatcttt tctacggggt ctgacgctca gtggaacgaa aactcacgtt    4080
aagggatttt ggtcatgaga ttatcaaaaa ggatcttcac ctagatcctt ttaaattaaa    4140
aatgaagttt taaatcaatc taaagtatat atgagtaaac ttggtctgac agttaccaat    4200
```

-continued

```
gcttaatcag tgaggcacct atctcagcga tctgtctatt tcgttcatcc atagttgcct    4260
gactccccgt cgtgtagata actacgatac gggagggctt accatctggc cccagtgctg    4320
caatgatacc gcgagaccca cgctcaccgg ctccagattt atcagcaata aaccagccag    4380
ccggaagggc cgagcgcaga agtggtcctg caactttatc cgcctccatc cagtctatta    4440
attgttgccg ggaagctaga gtaagtagtt cgccagttaa tagtttgcgc aacgttgttg    4500
ccattgctac aggcatcgtg gtgtcacgct cgtcgtttgg tatggcttca ttcagctccg    4560
gttcccaacg atcaaggcga gttacatgat cccccatgtt gtgcaaaaaa gcggttagct    4620
ccttcggtcc tccgatcgtt gtcagaagta agttggccgc agtgttatca ctcatggtta    4680
tggcagcact gcataattct cttactgtca tgccatccgt aagatgcttt tctgtgactg    4740
gtgagtactc aaccaagtca ttctgagaat agtgtatgcg gcgaccgagt tgctcttgcc    4800
cggcgtcaac acgggataat accgcgccac atagcagaac tttaaaagtg ctcatcattg    4860
gaaaacgttc ttcggggcga aaactctcaa ggatcttacc gctgttgaga tccagttcga    4920
tgtaacccac tcgtgcaccc aactgatctt cagcatcttt tactttcacc agcgtttctg    4980
ggtgagcaaa aacaggaagg caaaatgccg caaaaaaggg aataagggcg acacggaaat    5040
gttgaatact catactcttc cttttttcaat attattgaag catttatcag ggttattgtc    5100
tcatgagcgg atacatattt gaatgtattt agaaaaataa acaaataggg gttccgcgca    5160
catttccccg aaaagtgcca cctgacgtct aagaaaccat tattatcatg acattaacct    5220
ataaaaatag gcgtatcacg aggccctttc gtcttcaa                            5258
```

<210> SEQ ID NO 49
<211> LENGTH: 22
<212> TYPE: PRT
<213> ORGANISM: Toxoplasma gondii

<400> SEQUENCE: 49

```
Asp Leu Asp Pro Ser Thr Asn Ser Ser Val Pro Gly Asp Pro Leu
 1               5                  10                  15

Asp Cys Arg His Ala Lys
            20
```

<210> SEQ ID NO 50
<211> LENGTH: 22
<212> TYPE: PRT
<213> ORGANISM: Toxoplasma gondii

<400> SEQUENCE: 50

```
Asp Leu Asp Pro Ser Thr Asn Ser Ser Val Pro Gly Asp Pro Leu
 1               5                  10                  15

Asp Cys Arg His Ala Lys
            20
```

<210> SEQ ID NO 51
<211> LENGTH: 13
<212> TYPE: PRT
<213> ORGANISM: Toxoplasma gondii

<400> SEQUENCE: 51

```
Gly Leu Asn Ser Ser Ser Gly Ile Arg Leu Gln Thr Arg
 1               5                  10
```

<210> SEQ ID NO 52
<211> LENGTH: 506
<212> TYPE: PRT

<213> ORGANISM: Toxoplasma gondii

<400> SEQUENCE: 52

```
Met Ser Phe Val Val Ile Ile Pro Ala Arg Tyr Ala Thr Ser Arg Leu
 1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Asn Ser Met Ala Arg
                165                 170                 175

His Ala Ile Phe Ser Ala Leu Cys Val Leu Gly Leu Val Ala Ala Ala
            180                 185                 190

Leu Pro Gln Phe Ala Thr Ala Ala Thr Ala Ser Asp Asp Glu Leu Met
        195                 200                 205

Ser Arg Ile Arg Asn Ser Asp Phe Phe Asp Gly Gln Ala Pro Val Asp
    210                 215                 220

Ser Leu Arg Pro Thr Asn Ala Gly Val Asp Ser Lys Gly Thr Asp Asp
225                 230                 235                 240

His Leu Thr Thr Ser Met Asp Lys Ala Ser Val Glu Ser Gln Leu Pro
                245                 250                 255

Arg Arg Glu Pro Leu Glu Thr Glu Pro Asp Glu Gln Glu Glu Val His
            260                 265                 270

Phe Arg Lys Arg Gly Val Arg Ser Asp Ala Glu Val Thr Asp Asp Asn
        275                 280                 285

Ile Tyr Glu Glu His Thr Asp Arg Lys Val Val Pro Arg Lys Ser Glu
    290                 295                 300

Gly Lys Arg Ser Phe Lys Asp Leu Leu Lys Lys Leu Ala Leu Pro Ala
305                 310                 315                 320

Val Gly Met Gly Ala Ser Tyr Phe Ala Ala Asp Arg Leu Val Pro Glu
                325                 330                 335

Leu Thr Glu Glu Gln Gln Arg Gly Asp Glu Pro Leu Thr Thr Gly Gln
            340                 345                 350

Asn Val Gly Thr Val Leu Gly Phe Ala Ala Leu Ala Ala Ala Ala Ala
        355                 360                 365

Phe Leu Gly Met Gly Leu Thr Arg Thr Tyr Arg His Phe Ser Pro Arg
    370                 375                 380

Lys Asn Arg Ser Arg Gln Pro Ala Leu Glu Gln Glu Val Pro Glu Ser
385                 390                 395                 400
```

-continued

```
Gly Glu Asp Gly Glu Asp Ala Arg Gln Arg Ile Arg Leu Gln Thr Arg
                405                 410                 415

Leu Glu Thr Val Gly Asp Asn Phe Leu Arg His Leu Gly Ile Tyr Gly
                420                 425                 430

Tyr Arg Ala Gly Phe Ile Arg Arg Tyr Val Asn Trp Gln Pro Ser Pro
                435                 440                 445

Leu Glu His Ile Glu Met Leu Glu Gln Leu Arg Val Leu Trp Tyr Gly
                450                 455                 460

Glu Lys Ile His Val Ala Val Ala Gln Glu Val Pro Gly Thr Gly Val
465                 470                 475                 480

Asp Thr Pro Glu Asp Leu Asp Pro Ser Thr Asn Ser Ser Ser Val Pro
                485                 490                 495

Gly Asp Pro Leu Asp Cys Arg His Ala Lys
                500                 505

<210> SEQ ID NO 53
<211> LENGTH: 551
<212> TYPE: PRT
<213> ORGANISM: Toxoplasma gondii

<400> SEQUENCE: 53

Met Ser Phe Val Val Ile Ile Pro Ala Arg Tyr Ala Thr Ser Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
                35                  40                  45

Thr Asp His Glu Asp Val Ala Arg Ala Val Glu Ala Ala Gly Gly Glu
            50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Asn Ser Met Leu Val
                165                 170                 175

Ala Asn Gln Val Val Thr Cys Pro Asp Lys Lys Ser Thr Ala Ala Val
            180                 185                 190

Ile Leu Thr Pro Thr Glu Asn His Phe Thr Leu Lys Cys Pro Lys Thr
            195                 200                 205

Ala Leu Thr Glu Pro Pro Thr Leu Ala Tyr Ser Pro Asn Arg Gln Ile
            210                 215                 220

Cys Pro Ala Gly Thr Thr Ser Ser Cys Thr Ser Lys Ala Val Thr Leu
225                 230                 235                 240

Ser Ser Leu Ile Pro Glu Ala Glu Asp Ser Trp Trp Thr Gly Asp Ser
                245                 250                 255

Ala Ser Leu Asp Thr Ala Gly Ile Lys Leu Thr Val Pro Ile Glu Lys
            260                 265                 270
```

```
Phe Pro Val Thr Thr Gln Thr Phe Val Val Gly Cys Ile Lys Gly Asp
            275                 280                 285
Asp Ala Gln Ser Cys Met Val Thr Val Thr Val Gln Ala Arg Ala Ser
        290                 295                 300
Ser Val Val Asn Asn Val Ala Arg Cys Ser Tyr Gly Ala Asp Ser Thr
305                 310                 315                 320
Leu Gly Pro Val Lys Leu Ser Ala Glu Gly Pro Thr Thr Met Thr Leu
                325                 330                 335
Val Cys Gly Lys Asp Gly Val Lys Val Pro Gln Asp Asn Asn Gln Tyr
            340                 345                 350
Cys Ser Gly Thr Thr Leu Thr Gly Cys Asn Glu Lys Ser Phe Lys Asp
        355                 360                 365
Ile Leu Pro Lys Leu Thr Glu Asn Pro Trp Gln Gly Asn Ala Ser Ser
370                 375                 380
Asp Lys Gly Ala Thr Leu Thr Ile Lys Lys Glu Ala Phe Pro Ala Glu
385                 390                 395                 400
Ser Lys Ser Val Ile Ile Gly Cys Thr Gly Gly Ser Pro Glu Lys His
                405                 410                 415
His Cys Thr Val Lys Leu Glu Phe Ala Gly Ala Gly Ser Ala Lys
            420                 425                 430
Ser Ala Ala Gly Thr Ala Ser His Val Ser Ile Phe Ala Met Val Ile
        435                 440                 445
Gly Leu Ile Gly Ser Ile Ala Ala Cys Val Ala Thr Arg Leu Glu Thr
            450                 455                 460
Val Gly Asp Asn Phe Leu Arg His Leu Gly Ile Tyr Gly Tyr Arg Ala
465                 470                 475                 480
Gly Phe Ile Arg Arg Tyr Val Asn Trp Gln Pro Ser Pro Leu Glu His
                485                 490                 495
Ile Glu Met Leu Glu Gln Leu Arg Val Leu Trp Tyr Gly Glu Lys Ile
                500                 505                 510
His Val Ala Val Ala Gln Glu Val Pro Gly Thr Gly Val Asp Thr Pro
            515                 520                 525
Glu Asp Leu Asp Pro Ser Thr Asn Ser Ser Ser Val Pro Gly Asp Pro
        530                 535                 540
Leu Asp Cys Arg His Ala Lys
545                 550

<210> SEQ ID NO 54
<211> LENGTH: 398
<212> TYPE: PRT
<213> ORGANISM: Toxoplasma gondii

<400> SEQUENCE: 54

Met Ser Phe Val Val Ile Ile Pro Ala Arg Tyr Ala Ser Thr Arg Leu
 1               5                  10                  15
Pro Gly Lys Pro Leu Val Asp Ile Asn Gly Lys Pro Met Ile Val His
                20                  25                  30
Val Leu Glu Arg Ala Arg Glu Ser Gly Ala Glu Arg Ile Ile Val Ala
            35                  40                  45
Thr Asp His Glu Asp Val Ala Arg Ala Val Glu Ala Ala Gly Gly Glu
        50                  55                  60
Val Cys Met Thr Arg Ala Asp His Gln Ser Gly Thr Glu Arg Leu Ala
65                  70                  75                  80
Glu Val Val Glu Lys Cys Ala Phe Ser Asp Asp Thr Val Ile Val Asn
```

-continued

```
                    85                  90                  95
Val Gln Gly Asp Glu Pro Met Ile Pro Ala Thr Ile Ile Arg Gln Val
                100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Met Asn Gly Pro Leu
                165                 170                 175

Ser Tyr His Pro Ser Ser Tyr Gly Ala Ser Tyr Pro Asn Pro Ser Asn
            180                 185                 190

Pro Leu His Gly Met Pro Lys Pro Glu Asn Pro Val Arg Pro Pro Pro
        195                 200                 205

Pro Gly Phe His Pro Ser Val Ile Pro Asn Pro Pro Tyr Pro Leu Gly
    210                 215                 220

Thr Pro Ala Ser Met Pro Gln Pro Glu Val Pro Pro Leu Gln His Pro
225                 230                 235                 240

Pro Pro Thr Gly Ser Pro Pro Ala Ala Ala Pro Gln Pro Pro Tyr Pro
                245                 250                 255

Val Gly Thr Pro Val Met Pro Gln Pro Glu Ile Pro Pro Val His Arg
            260                 265                 270

Pro Pro Pro Pro Gly Phe Arg Pro Glu Val Ala Pro Val Pro Pro Tyr
        275                 280                 285

Pro Val Gly Thr Pro Thr Gly Met Pro Gln Pro Glu Ile Pro Ala Val
    290                 295                 300

His His Thr Arg Leu Glu Thr Val Gly Asp Asn Phe Leu Arg His Leu
305                 310                 315                 320

Gly Ile Tyr Gly Tyr Arg Ala Gly Phe Ile Arg Arg Tyr Val Asn Trp
                325                 330                 335

Gln Pro Ser Pro Leu Glu His Ile Glu Met Leu Glu Gln Leu Arg Val
            340                 345                 350

Leu Trp Tyr Gly Glu Lys Ile His Val Ala Val Ala Gln Glu Val Pro
        355                 360                 365

Gly Thr Gly Val Asp Thr Pro Glu Asp Leu Asp Pro Ser Thr Asn Ser
    370                 375                 380

Ser Ser Val Pro Gly Asp Pro Leu Asp Cys Arg His Ala Lys
385                 390                 395
```

<210> SEQ ID NO 55
<211> LENGTH: 667
<212> TYPE: PRT
<213> ORGANISM: Toxoplasma gondii

<400> SEQUENCE: 55

```
Met Ser Phe Val Val Ile Ile Pro Ala Arg Tyr Ala Thr Ser Arg Leu
  1               5                  10                  15

Pro Gly Lys Pro Leu Val Asp Ile Asn Gly Lys Pro Met Ile Val His
                 20                  25                  30

Val Leu Glu Arg Ala Arg Glu Ser Gly Ala Glu Arg Ile Ile Val Ala
             35                  40                  45

Thr Asp His Glu Asp Val Ala Arg Ala Val Glu Ala Ala Gly Gly Glu
         50                  55                  60
```

-continued

```
Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Met Ser His Asn Gly
                165                 170                 175

Val Pro Ala Tyr Pro Ser Tyr Ala Gln Val Ser Leu Ser Ser Asn Gly
            180                 185                 190

Glu Pro Arg His Arg Gly Ile Arg Gly Ser Phe Leu Met Ser Val Lys
            195                 200                 205

Pro His Ala Asn Ala Asp Asp Phe Ala Ser Asp Asp Asn Tyr Glu Pro
            210                 215                 220

Leu Pro Ser Phe Val Glu Ala Pro Val Arg Gly Pro Asp Gln Val Pro
225                 230                 235                 240

Ala Arg Gly Glu Ala Ala Leu Val Thr Glu Glu Thr Pro Ala Gln Gln
                245                 250                 255

Pro Ala Val Ala Leu Gly Ser Ala Glu Gly Glu Gly Thr Ser Thr Thr
            260                 265                 270

Glu Ser Ala Ser Glu Asn Ser Glu Asp Asp Thr Phe His Asp Ala
            275                 280                 285

Leu Gln Glu Leu Pro Glu Asp Gly Leu Glu Val Arg Pro Pro Asn Ala
            290                 295                 300

Gln Glu Leu Pro Pro Asn Val Gln Glu Leu Pro Pro Asn Val
305                 310                 315                 320

Gln Glu Leu Pro Pro Thr Glu Gln Glu Leu Pro Pro Thr Glu
                325                 330                 335

Gln Glu Leu Pro Pro Thr Glu Gln Glu Leu Pro Pro Thr Glu
            340                 345                 350

Gln Glu Leu Pro Pro Ser Thr Glu Gln Glu Leu Pro Pro Val Gly
            355                 360                 365

Glu Gly Gln Arg Leu Gln Val Pro Gly Glu His Gly Pro Gln Gly Pro
            370                 375                 380

Pro Tyr Asp Asp Gln Gln Leu Leu Leu Glu Pro Thr Glu Glu Gln Gln
385                 390                 395                 400

Glu Gly Pro Gln Glu Pro Leu Pro Pro Pro Pro Thr Arg Gly
                405                 410                 415

Glu Gln Pro Glu Gly Gln Gln Pro Gln Gly Pro Val Arg Gln Asn Phe
            420                 425                 430

Phe Arg Arg Ala Leu Gly Ala Ala Arg Ser Arg Phe Gly Gly Ala Arg
            435                 440                 445

Arg His Val Ser Gly Val Phe Arg Val Arg Gly Gly Leu Asn Arg
            450                 455                 460

Ile Val Gly Gly Val Arg Ser Gly Phe Arg Arg Ala Arg Glu Gly Val
465                 470                 475                 480

Val Gly Gly Val Arg Arg Leu Thr Ser Gly Ala Ser Leu Gly Leu Arg
```

-continued

```
                485                 490                 495
Arg Val Gly Glu Gly Leu Arg Arg Ser Phe Tyr Arg Val Arg Gly Ala
            500                 505             510

Val Ser Ser Gly Arg Arg Arg Ala Ala Asp Gly Ala Ser Asn Val Arg
        515                 520             525

Glu Arg Phe Val Ala Ala Gly Gly Arg Val Arg Asp Ala Phe Gly Ala
    530                 535             540

Gly Leu Thr Arg Leu Arg Arg Gly Arg Thr Asn Gly Glu Glu Gly
545                 550             555                 560

Arg Pro Leu Leu Gly Glu Gly Arg Glu Gln Asp Asp Gly Ser Gln Thr
            565                 570             575

Arg Leu Glu Thr Val Gly Asp Asn Phe Leu Arg His Leu Gly Ile Tyr
            580                 585             590

Gly Tyr Arg Ala Gly Phe Ile Arg Arg Tyr Val Asn Trp Gln Pro Ser
        595                 600             605

Pro Leu Glu His Ile Glu Met Leu Glu Gln Leu Arg Val Leu Trp Tyr
        610                 615             620

Gly Glu Lys Ile His Val Ala Val Ala Gln Glu Val Pro Gly Thr Gly
625                 630             635                 640

Val Asp Thr Pro Glu Asp Leu Asp Pro Ser Thr Asn Ser Ser Ser Val
            645                 650             655

Pro Gly Asp Pro Leu Asp Cys Arg His Ala Lys
            660                 665
```

METHOD OF USING P35 ANTIGEN OF *TOXOPLASMA GONDII* IN DISTINGUISHING ACUTE FROM CHRONIC TOXOPLASMOSIS

The present application is a Continuation-In-Part of U.S. patent application Ser. No. 09/086,503, filed on May 28, 1998, now co-pending, hereby incorporated in its entirety by reference.

BACKGROUND OF THE INVENTION

1. Technical Field

The present invention relates to combinations or mixtures of antigens which may be used in the detection of IgM or IgG antibodies to *Toxoplasma gondii*, as well as one antigen, in particular, which may be used to distinguish between acute and chronic infection. Furthermore, the present invention also relates to methods of using these combinations of antigens, antibodies raised against these combinations of antigens or against the novel P29 antigen thereof, as well as kits and vaccines containing the antigens present in the combinations.

2. Background Information

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140–267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites which can infect the individual resulting in an acute infection. Oocysts represent a stage of sexual reproduction which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudesence of a previous *T. gondii* infection or an acute infection in an immunosuppressed individual can be pathogenic. Toxoplasmic encephalitis is a major cause of morbidity and mortality in AIDS patients. Toxoplasma infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660–663), the indirect hemagglutination (IHA) test (Jacobs, L. and Lunde, M. (1957) J. Parasitol. 43, 308–314), the IFA test (Walton, B. C. et al. (1966) Am. J. Trop. Med. Hyg. 15, 149–152), the agglutination test (Fondation Mérieux, Sérologie de I'Infection Toxoplasmique en Particulier à Son Début: Méthodes et Interprétation des Résultants, Lyon, 182 pp. (1975)) and the ELISA (Naot, Y. and Remington, J. S. (1980) J. Infect. Dis. 142, 757–766). The ELISA test is one the easiest tests to perform, and many automated serologic tests for the detection of Toxoplasma specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, as described above, as well as the persistent problems regarding determination of onset of infection, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P30 (SAG1), P35 (mentioned above), P41 (GRA4), P54 (ROP2), P66 (ROP1), and the Toxo P68 antigens have been described (Prince et al. (1990) Mol. Biochem. Parasitol 43, 97–106; Cesbron-Delauw et al. (1989) Proc. Nat. Acad. Sci. 86, 7537–7541; Johnson et al. (1991) Gene 99, 127–132; Prince et al. (1989) Mol. Biochem. Parasitol. 34, 3–13; Burg et al. (1988) J. Immunol. 141, 3584–3591; Knapp et al. (1989) EPA 431541A2; Mevelec et al. (1992) Mol. Biochem. Parasitol. 56, 227–238; Saavedra et al. (1991) J. Immunol. 147, 1975–1982; EPA 751 147).

It is plausible that no single Toxo antigen can replace the tachyozoite in an initial screening immunoassay for the detection of Toxo-specific immunoglobulins. This may be due to several reasons. First, the antibodies produced during infection vary with the stage of infection, i.e., the antibodies produced by an infected individual vary over time reacting with different epitopes. Secondly, the epitopes present in a recombinant antigen may be different or less reactive than native antigen prepared from the tachyzoite depending on the host used for expression and the purification scheme employed. Thirdly, different recombinant antigens may be needed to detect the different classes of immunoglobulins produced in response to an infection, e.g., IgM, IgG, IgA and IgE.

In order to overcome the limitations of the tachyzoite antigen in terms of assay specificity and sensitivity, a search was begun for novel Toxo antigens which could be used in combination with known existing antigens in order to configure new assays for the detection of Toxo-specific immunoglobulins.

Additionally, it should be noted that the presence of IgG antibodies in a single sample of serum is sufficient to establish that the patient has been infected but does not give an indication as to when the infection occurred. In the United States, there is no systematic serological screening program in pregnant women, whereas in countries such as France and Austria, sera are obtained at regular intervals throughout gestation in women who are seronegative when first tested. In the United States, a decision regarding whether the woman was recently infected, thereby placing her fetus at risk, is often made from results in a single sample of serum. However, it is critical in pregnant women to determine as accurately as possible if they acquired their infection just prior to or during gestation. For this reason, the presence of IgG antibodies in a pregnant woman often leads to additional serological testing to attempt to determine if the infection was acquired during pregnancy or in the distant past (Remington et al., 1995, Toxoplasmosis, $4^{th}$ ed., Coord. Ed., Remington, J. S., W. B. Saunders, Philadelphia, Pa.). of the recommended additional serological tests, those that demonstrate the presence of IgM antibodies are most frequently used. However, since IgM antibodies may remain detectable for more than one year after initial infection, demonstration of these antibodies cannot be used to prove recently acquired infection (Liesebfeld et al., *Journal of Clinical Microbiology* 35:174–78 (1997); Wilson et al., *Journal of Clinical Microbiology* 35:3112–15 (1997); Wong et al., *Clinical Infectious Diseases* 18:853–62 (1994)). Because accurate diagnosis of the recently acquired infection in pregnant women is important for clinical management of both the mother and her fetus, a search has continued for better diagnostic methods (Remington et al., 1995, Toxoplasmosis, $4^{th}$ ed., Coord. Ed., J. S. Remington, W. B. Saunders, Philadelphia, Pa.; Wong et al., supra).

In previous studies, it was observed that a 35 kDa antigen was detected in immunoblots of tachyzoite extracts probed with serum from individuals early after they became infected with *T. gondii* and postulated that this antigen might prove useful for detection of the acute stage of the infection (Potasman et al., Journal of Infectious Diseases 154:650–57 (1986); Potasman et al., Journal of Clinical Microbiology 25:1926–31 (1987)). Thus, a gene in the GenBank sequence database for *T. gondii* putatively identified as "P35" was selected for cloning, expression, and evaluation of a corresponding recombinant protein for its capacity to detect serum antibodies during the early phase of the infection. This antigen will be described in further detail below.

Additionally, it was determined that a portion of one of these antigens (i.e., P35) could be utilized to distinguish between acute and chronic infection.

SUMMARY OF THE INVENTION

The present invention includes a composition comprising *Toxoplasma gondii* antigens P29, P30 and P35 as well as a composition comprising *Toxoplasma gondii* antigens P29, P35 and 66. These compositions may be used as diagnostic reagents, and the antigens within these compositions may be produced either recombinantly or synthetically.

Additionally, the present invention includes an isolated nucleic acid sequence represented by SEQ ID NO: 26 and a purified polypeptide having the amino acid sequence represented by SEQ ID NO: 27. The present invention also includes a polyclonal or monoclonal antibody directed against the purified polypeptide.

The present invention also encompasses a method for detecting the presence of IgM antibodies to *Toxoplasma gondii* in a test sample. This method comprises the steps of: a) contacting the test sample suspected of containing the IgM antibodies with a composition comprising P29, P35 and P66; and b) detecting the presence of the IgM antibodies.

Furthermore, the present invention includes an additional method for detecting the presence of IgM antibodies to *Toxoplasma gondii* in a test sample. This method comprises the steps of: a) contacting the test sample suspected of containing the IgM antibodies with a composition comprising antigen P29, P35 and P66 for a time and under conditions sufficient for the formation of IgM antibody/antigen complexes; b) adding a conjugate to the resulting IgM antibody/antigen complexes for a time and under conditions sufficient to allow the conjugate to bind to the bound antibody, wherein the conjugate comprises an antibody attached to a signal generating compound capable of generating a detectable signal; and c) detecting the presence of IgM antibodies which may be present in the test sample by detecting a signal generated by the signal generating compound.

Moreover, the present invention also includes a method for detecting the presence of IgG antibodies to *Toxoplasma gondii* in a test sample. This method comprises the steps of: a) contacting the test sample suspected of containing the IgG antibodies with a composition comprising P29, P30 and P35; and b) detecting the presence of the IgG antibodies.

Additionally, the present invention encompasses another method for detecting the presence of IgG antibodies to *Toxoplasma gondii* in a test sample. This method comprising the steps of: a) contacting said test sample suspected of containing the IgG antibodies with a composition comprising antigen P29, P30 and P35 for a time and under conditions sufficient for formation of IgG antibody/antigen complexes; b) adding a conjugate to resulting IgG antibody/antigen complexes for a time and under conditions sufficient to allow the conjugate to bind to bound antibody, wherein the conjugate comprises an antibody attached to a signal generating compound capable of generating a detectable signal; and c) detecting IgG antibodies which may be present in said test sample by detecting a signal generated by said signal generating compound.

Additionally, the present invention includes another method for detecting the presence of IgM antibodies to *Toxoplasma gondii* in a test sample. This method comprises the steps of: a) contacting the test sample suspected of containing the IgM antibodies with anti-antibody specific for the IgM antibodies for a time and under conditions sufficient to allow for formation of anti-antibody/IgM antibody complexes; b) adding a conjugate to resulting anti-antibody/IgM antibody complexes for a time and under conditions sufficient to allow the conjugate to bind to bound antibody, wherein the conjugate comprises P29, P35 and P66, each attached to a signal generating compound capable of generating a detectable signal; and c) detecting IgM antibodies which may be present in the test sample by detecting a signal generated by the signal generating compound.

Another method for detecting the presence of IgG antibodies to *Toxoplasma gondii* in a test sample, encompassed by the present invention, comprises the steps of: a) contacting the test sample suspected of containing the IgG antibodies with anti-antibody specific for the IgG antibodies for a time and under conditions sufficient to allow for formation of anti-antibody/IgG antibody complexes; b) adding a conjugate to resulting anti-antibody/IgG antibody complexes for a time and under conditions sufficient to allow the conjugate to bind to bound antibody, wherein the conjugate comprises P29, P30 and P35, each attached to a signal generating compound capable of generating a detectable signal; and c) detecting IgG antibodies which may be present in the test sample by detecting a signal generated by the signal generating compound.

Also, the present invention includes a vaccine comprising: 1) *Toxoplasma gondii* antigens P29, P30 and P35 and 2) a pharmaceutically acceptable adjuvant as well as a vaccine comprising: 1) *Toxoplasma gondii* antigens P29, P35 and P66 and 2) a pharmaceutically acceptable adjuvant.

Additionally, the present invention includes a kit for determining the presence of IgM antibodies to *Toxoplasma gondii* in a test sample comprising: a) a composition comprising *Toxoplasma gondii* antigens P29, P35 and P66 and b) a conjugate comprising an antibody attached to a signal generating compound capable of generating a detectable signal.

The present invention also includes a kit for determining the presence of IgG antibodies to *Toxoplasma gondii* in a test sample comprising: a) a composition comprising *Toxoplasma gondii* antigens P29, P30 and P35 and b) a conjugate comprising an antibody attached to a signal generating compound capable of generating a detectable signal.

An additional kit for determining the presence of IgM antibodies to *Toxoplasma gondii* in a test sample, encompassed by the present invention, comprises: a) an anti-antibody specific for IgM antibody and b) a composition comprising *Toxoplasma gondii* antigens P29, P35 and P66.

The present invention also includes a kit for determining the presence of IgM antibodies to *Toxoplasma gondii* in a test sample comprising: a) an anti-antibody specific for IgM antibody and b) a conjugate comprising: 1) *Toxoplasma gondii* antigens P29, P35 and P66, each attached to 2) a signal generating compound capable of generating a detectable signal.

Additionally, the present invention includes a kit for determining the presence of IgG antibodies to *Toxoplasma gondii* in a test sample comprising: a) an anti-antibody specific for IgG antibody and b) a composition comprising *Toxoplasma gondii* antigens P29, P30 and P35.

The present invention also includes an additional kit for determining the presence of antibodies to *Toxoplasma gondii* in a test sample comprising: a) an anti-antibody specific for IgG antibody and b) a conjugate comprising: 1) *Toxoplasma gondii* antigens P29, P30 and P35, each attached to 2) a signal generating compound capable of generating a detectable signal.

Additionally, the present invention includes a method for detecting the presence of IgM antibodies to *Toxoplasma gondii* in a test sample comprising the steps of: (a) contacting the test sample suspected of containing IgM antibodies with anti-antibody specific for the IgM antibodies for a time and under conditions sufficient to allow for formation of anti-antibody IgM complexes; (b) adding antigen to resulting anti-antibody/IgM complexes for a time and under conditions sufficient to allow the antigen to bind to bound IgM antibody, the antigen comprising a mixture of P29, P35 and P66; and (c) adding a conjugate to resulting anti-antibody/IgM/antigen complexes, the conjugate comprising a composition comprising monoclonal or polyclonal antibody attached to a signal generating compound capable of generating a detectable signal; and (d) detecting IgM antibodies which may be present in the test sample by detecting a signal generated by the signal generating compound.

The present invention also includes a method for detecting the presence of IgG antibodies to Toxoplasma gondii in a test sample comprising the steps of: (a) contacting the test sample suspected of containing IgG antibodies with anti-antibody specific for said IgG antibodies for a time and under conditions sufficient to allow for formation of anti-antibody IgG complexes; (b) adding antigen to resulting anti-antibody/IgG complexes for a time and under conditions sufficient to allow said antigen to bind to bound IgG antibody, the antigen comprising a mixture of P29, P30 and P35; and (c) adding a conjugate to resulting anti-antibody/IgG/antigen complexes, the conjugate comprising a composition comprising monoclonal or polyclonal antibody attached to a signal generating compound capable of generating a detectable signal; and (d) detecting IgG antibodies which may be present in the test sample by detecting a signal generated by the signal generating compound.

A further method for detecting the presence of IgM and IgG antibodies to *Toxoplasma gondii* in a test sample, included within the present invention, comprises the steps of: a) contacting the test sample suspected of containing the IgM and IgG antibodies with a composition comprising antigen P29, P30, P35 and P66 for a time and under conditions sufficient for the formation of IgM antibody/antigen complexes and IgG antibody/antigen complexes; b) adding a conjugate to the resulting IgM antibody/antigen complexes and IgG antibody/antigen complexes for a time and under conditions sufficient to allow the conjugate to bind to the bound IgM and IgG antibody, wherein said conjugate comprises an antibody attached to a signal generating compound capable of generating a detectable signal; and c) detecting the presence of IgM and IgG antibodies which may be present in the test sample by detecting a signal generated by the signal generating compound.

The present invention also includes a method for detecting the presence of IgM and IgG antibodies to *Toxoplasma gondii* in a test sample comprising the steps of: a) contacting the test sample suspected of containing the IgM and IgG antibodies with anti-antibody specific for said IgM antibodies and the IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow the conjugate to bind to bound antibody, wherein the conjugate comprises P29, P30, P35 and P66, each attached to a signal generating compound capable of generating a detectable signal; and c) detecting IgM and IgG antibodies which may be present in the test sample by detecting a signal generated by the signal generating compound.

The present invention also includes a method for detecting the presence of IgM and IgG antibodies to *Toxoplasma gondii* in a test sample comprising the steps of: (a) contacting the test sample suspected of containing IgM and IgG antibodies with anti-antibody specific for the IgM antibodies and with anti-antibody specific for the IgG antibodies for a time and under conditions sufficient to allow for formation of anti-antibody/IgM complexes and anti-antibody/IgG complexes; (b) adding antigen to resulting anti-antibody/IgM complexes and resulting anti-antibody/IgG complexes for a time and under conditions sufficient to allow the antigen to bind to bound IgM antibody and bound IgG antibody, the antigen comprising a mixture of P29, P30, P35 and P66; and (c) adding a conjugate to resulting anti-antibody/IgM/antigen complexes and anti-antibody/IgG/antigen complexes, the conjugate comprising a composition comprising monoclonal or polyclonal antibody attached to a signal generating compound capable of generating a detectable signal; and (d) detecting IgM and IgG antibodies which may be present in the test sample by detecting a signal generated by the signal generating compound.

Additionally, the p resent invention encompasses a method of producing monoclonal antibodies comprising the steps of:

a) injecting a non-human mammal with an antigen;

b) administering a composition comprising antibiotics to the non-human mammal;

c) fusing spleen cells of the non-human mammal with myeloma cells in order to generate hybridomas; and d) culturing the hybridomas under sufficient time and conditions such that the hybridomas produce monoclonal antibodies.

The antigen utilized may be derived from, for example, *T. gondii*.

The present invention also encompasses a composition comprising the isolated nucleic acid sequence illustrated in FIG. 11 or a fragment thereof.

Additionally, the present invention includes a composition comprising amino acids 1–135 of P35. Either of the two compositions may be a diagnostic reagent. The present invention also includes portions or fragments of P35 which have the same antigenic properties as the region of P35 which consists of amino acids 1–135.

The present invention also includes a method for distinguishing between acute and chronic toxoplasmosis in a patient suspected of having either acute or chronic toxoplasmosis. This method comprises the steps of: a) contacting a test sample, from the patient, with a composition comprising amino acids 1–135 of P35; and b) detecting the presence of IgG antibodies, presence of the IgG antibodies indicating acute toxoplasmosis in the patient and lack of the IgG antibodies indicating chronic toxoplasmosis in the patient.

Further, the present invention includes a kit for distinguishing between acute and chronic toxoplasmosis in a patient suspected of having either acute toxoplasmosis or chronic Toxoplasmosis comprising: a) a composition comprising amino acids 1–135 of *Toxoplasma gondii* antigen P35; and b) a conjugate comprising an antibody attached to a signal generating compound capable of generating a detectable signal.

Additionally, the present invention encompasses a kit for distinguishing between acute and chronic toxoplasmosis in a patient suspected of having either acute toxoplasmosis or chronic toxoplasmosis comprising: a) an anti-antibody specific for IgG antibody; and b) a conjugate comprising amino acids 1–135 of *Toxoplasma gondii* antigen P35 attached to a signal generating compound capable of generating a detectable signal.

All U.S. patents and publications referred to herein are hereby incorporated in their entirety by reference.

BRIEF DESCRIPTION OF THE DRAWINGS

FIGS. 1A, 1B and 1C represent the DNA sequence [SEQ ID NO: 23] of nucleotides 1–1268 and the corresponding amino acid sequence [SEQ ID NO: 24] of plasmid pGM613.

FIG. 2 represents the DNA sequence [SEQ ID NO: 25] of nucleotides 1–477 of plasmid pTXG1-2.

FIGS. 3A, 3B, 3C and 3D represent the composite DNA sequence [SEQ ID NO: 26] of nucleotides 1–1648 and the corresponding amino acid sequence [SEQ ID NO: 27] for the P29 gene.

FIG. 4 is a schematic representation of (A) the construction of plasmid pEE2; (B) the nucleotide sequence [SEQ ID NO: 28] and the corresponding amino acid sequence [SEQ ID NO: 49] of the polylinker to be removed from pEE1 by digestion with BglII; and (C) the nucleotide sequence [SEQ ID NO: 29] and the corresponding amino acid sequence [SEQ ID NO: 50] of the synthetic DNA to be introduced into the BglII site of pEE1 to generate plasmid pEE2.

FIGS. 7A through 7J illustrate the DNA sequence [SEQ ID NO: 37] of nucleotides 1–4775 and the corresponding amino acid sequence [SEQ ID NO: 52] of the CKS-P29-CKS fusion protein of plasmid pToxo-P29.

FIGS. 9A through 9I represent the DNA sequence [SEQ ID NO: 40] of nucleotides 1–4910 and the corresponding amino acid sequence [SEQ ID NO: 53] of the CKS-P30-CKS fusion protein of plasmid pToxo-P30.

FIGS. 11A through 11I illustrate the DNA sequence [SEQ ID NO: 45] of nucleotides 1–4451 and the corresponding amino acid sequence [SEQ ID NO: 54] of the CKS-P35-CKS fusion protein of plasmid pToxo-P35S. The first 171 amino acids represent a portion of CKS, the next 135 amino acids represent amino acids 1–135 of P35, and the remaining amino acids represent the remainder of CKS.

FIGS. 13A through 13K represent the DNA sequence [SEQ ID NO: 48] of nucleotides 1–5258 and the corresponding amino acid sequence [SEQ ID NO: 55] of the CKS-P66-CKS fusion protein of plasmid pToxo-P66g.

DETAILED DESCRIPTION OF THE INVENTION

Figure 5A:
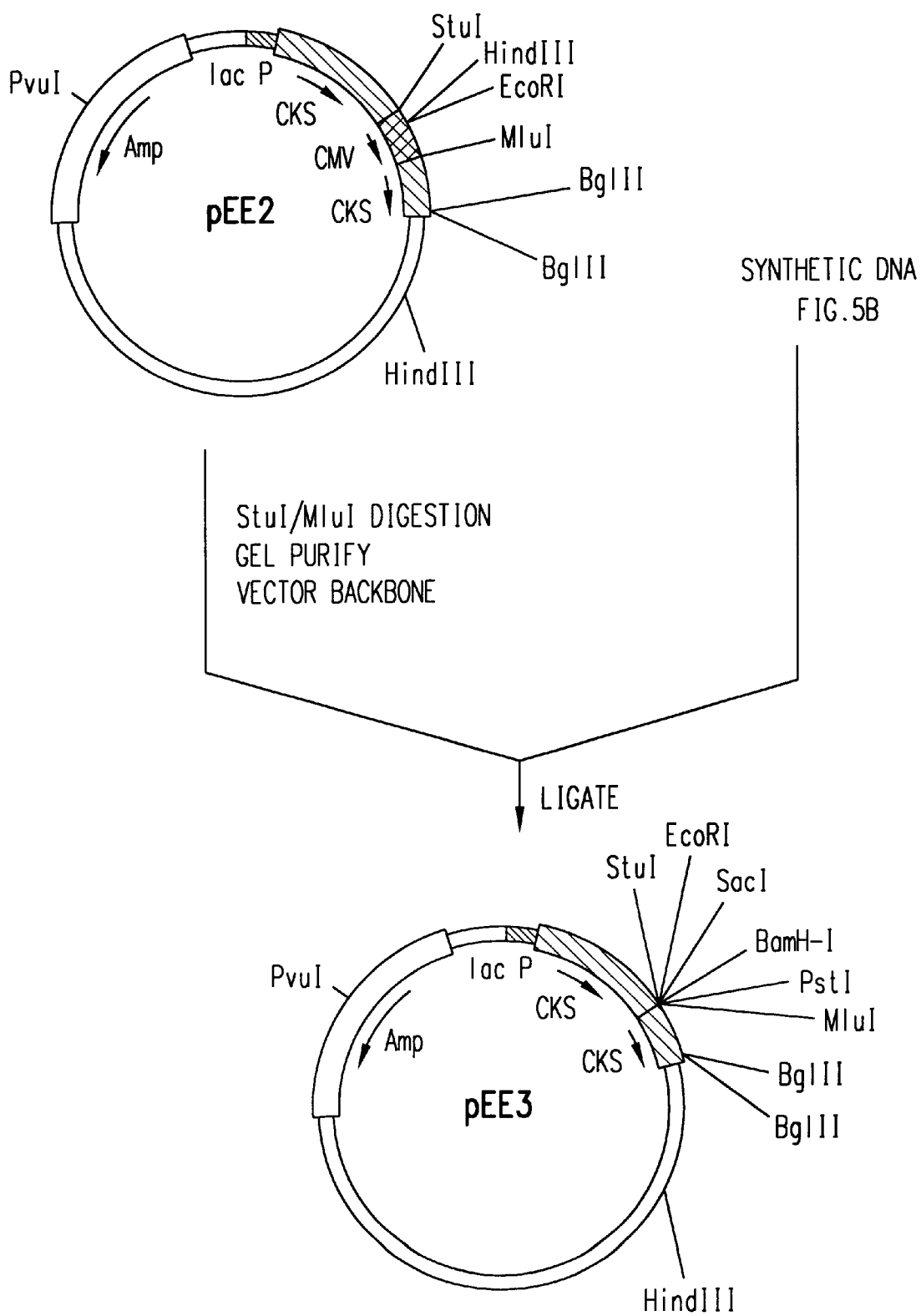
FIG. 5 is a schematic representation of (A) the construction of plasmid pEE3; and (B) the nucleotide sequence [SEQ ID NO: 32] and the corresponding amino acid sequence [SEQ ID NO: 51] of the synthetic DNA polylinker to be introduced into the StuI/MluI sites of pEE2 to generate plasmid pEE3.

The difficulties of known assays for the detection of IgG and IgM antibodies to *T. gondii* have been described, in detail, above. Thus, there was a need to discover immunoassays which could accurately detect the presence of such antibodies in positive serum, thereby eliminating the problem of false negative or false positive tests. The present invention provides such needed immunoassays and, in particular, combinations of antigens which accurately detect the presence of IgG or IgM antibodies in human sera.

In particular, the present invention includes a novel antigen which, for purposes of the present invention, is referred to as P29. The nucleotide sequence of the gene encoding this antigen is shown in FIGS. 3A, 3B, 3C and 3D and is represented by SEQ ID NO. 26. The amino acid sequence of this antigen is shown in FIGS. 3A, 3B, 3C and 3D and is represented by SEQ ID NO. 27.

P29, a dense granule protein, when used in combination with other known antigens, may accurately detect the presence of IgG or IgM in human sera. In particular, P29, when used in combination with other known antigens, may replace the tachyzoite previously used in assays for *T. gondii* antibodies.

Furthermore, the present invention also includes a polyclonal or monoclonal antibody raised against P29. Such an antibody may be used, for example, in an immunoassay, a vaccine, a kit, or for research purposes.

The present invention also encompasses a composition or mixture comprising the following three antigens: P29, P30 and P35. This combination or mixture of antigens may be utilized for the detection of IgG in IgG-positive sera (i.e., as a diagnostic reagent). Furthermore, the antigens may be produced either recombinantly or synthetically. Additionally, the present invention also includes a composition comprising antibodies raised against these antigens.

The present invention also includes a composition or mixture comprising the following three antigens: P29, P35 and P66. This combination or mixture of antigens may be used for the detection of IgM in IgM-positive sera (i.e., as a diagnostic reagent), and the antigens may be produced either recombinantly or synthetically. Furthermore, the present invention also includes a composition comprising antibodies raised against these antigens.

If, in fact, one wishes to measure both the titer of IgM and IgG in an individual, then a composition or mixture of antigens P29, P30, P35 and P66 may be utilized in an immunoassay. Such a combination of antigens is also included within the scope of the present invention.

The present invention also includes methods of detecting IgM and/or IgG using the combinations of antigens described above. More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product. Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

In particular, two illustrative examples of an immunometric antibody-capture based immunoassay are the Imx Toxo IgM and Toxo IgG antibody assays manufactured by Abbott Laboratories (Abbott Park, Ill.). Both assays are automated Microparticle Enzyme Immunoasssays (MEIA) which measure antibodies to *Toxoplasma gondii* (*T. gondii*) in human serum or plasma (Safford et al., *J. Clin. Pathol.* 44:238–242 (1991)). One assay quantitatively measures IgM antibodies, indicative of recent exposure or acute infection, and the other assay quantitatively measures IgG, indicative of chronic or past infection. These assays use microparticles coated with *T. gondii* antigens as the solid phase. In particular, specimen is added to the coated microparticles to allow antibodies specific for *T. gondii* to bind. Subsequently, an alkaline phosphatase conjugated anti-human IgM (or anti-human IgG) is added that specifically binds to IgM (or IgG) class antibodies complexed to the *T. gondii* antigens. Following addition of a suitable substrate (e.g., 4-methyumbelliferyl phosphate), the rate of enzyme-catalyzed turnover is monitored based upon fluorescence.

The mixture of P29, P30 and P35 may be used in the IgG Abbott immunoassay, and the mixture of P29, P35 and P66 may be utilized in the IgM Abbott immunoassay. Additionally, A mixture of P29, P30, P35, and P66 may be utilized in either assay, if desired. Furthermore, it must be noted that other non-Abbott assays or platforms may also be utilized, with each of the combinations of antigens (i.e., 3 or 4 antigens), for purposes of the present invention.

Thus, the present invention includes a method of detecting IgM antibodies in a test sample comprising the steps of: (a) contacting the test sample suspected of containing the IgM antibodies with P29, P35 and P66; (b) detecting the presence of IgM antibodies present in the test sample. More specifically, the present invention includes a method of detecting IgM antibodies in a test sample comprising the steps of: (a) contacting the test sample suspected of containing the IgM antibodies with P29, P35 and P66 for a time and under conditions sufficient to allow the formation of IgM antibody/antigen complexes; (b) adding a conjugate to the resulting IgM antibody/antigen complexes for a time and under conditions sufficient to allow the conjugate to bind to the bound antibody, the conjugate comprising an antibody (directed against the IgM) attached to a signal generating compound capable of generating a detectable signal; (c) detecting the presence of the IgM antibody which may be present in the test sample by detecting the signal generated by the signal generating compound. A control or calibrator may also be used which binds to the antigens. Furthermore, the method may also comprise the use of P30 in addition P29, P35 and P66.

In each of the above assays, IgG may be detected by substituting the P29, P35 and P66 mixture with a P29, P30 and P35 mixture. Additionally, the antibody in the conjugate will be directed against IgG rather than IgM. Additionally, if one wishes to detect both IgM and IgG antibodies, P29, P30, P35 and P66 may be utilized in the immunoassay. Furthermore, if desired, one may also add P66 to the assay, even if detection of antibodies to only IgG is required.

Additionally, the present invention also includes a method for detecting the presence of IgM which may be present in a test sample. This method comprises the steps of: (a) contacting the test sample suspected of containing IgM antibodies with anti-antibody specific for the IgM, for a time and under conditions sufficient to allow for formation of anti-antibody/IgM complexes and (b) detecting the presence of IgM which may be present in the test sample. (Such anti-antibodies are commercially available and may be created, for example, by immunizing a mammal with purified mu-chain of the antibody.)

More specifically, this method may comprise the steps of: (a) contacting the test sample suspected of containing the IgM antibodies with anti-antibody specific for the IgM, under time and conditions sufficient to allow the formation of anti-antibody/IgM complexes; (b) adding a conjugate to the resulting anti-antibody/IgM complexes for a time and under conditions sufficient to allow the conjugate to bind to the bound antibody, the conjugate comprising P29, P35 and P66, each being attached to a signal generating compound capable of generating a detectable signal; and (c) detecting the presence of the IgM antibodies which may be present in the test sample by detecting the signal generated by the signal generating compound. A control or calibrator may be used which comprises antibody to the anti-antibody. Furthermore, the conjugate may also comprise P30, if desired.

In each of the above assays, IgG may be detected by substituting the P29, P35 and P66 mixture with a P29, P30 and P35 mixture . Also, anti-antibody specific for IgG will be used. Additionally, if one wishes to detect both IgM and IgG antibodies, P29, P30, P35 and P66 may be utilized in the immunoassay. Moreover, even if one wishes to detect IgG only, P66 may also be added to the assay, if desired.

The present invention also encompasses a third method for detecting the presence of IgM in a test sample. This method comprises the steps of: (a) contacting the test sample suspected of containing IgM antibodies with anti-antibody specific for the IgM, under time and conditions sufficient to allow the formation of anti-antibody IgM compelxes; (b) adding antigen to the resulting anti-antibody/IgM complexes for a time and under conditions sufficient to allow the antigen to bind to the bound IgM antibody, the antigen comprising a mixture of P29, P35 and P66; and (c) adding a conjugate to the resulting anti-antibody/IgM/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the IgM antibodies which may be present in the test sample by detecting the signal generated by the signal generating compound. Again, a control or calibrator may be used which comprises antibody to the anti-antibody. The antigen mixture may further comprise P30, if desired.

In this method, IgG may be detected by substituting the P29, P35 and P66 mixture with a P29, P30 and P35 mixture and utilizing anti-antibody specific for IgG. However, if one wishes to detect both IgM and IgG antibodies, P29, P30, P35 and P66 may be utilized in the immunoassay. Even if one wishes to detect IgG alone, the assay may further comprise the use of P66.

It should also be noted that all of the above methods may be used to detect IgA antibodies (with an alpha-specific conjugate) and/or IgE antibodies (with an epsilon-specific conjugate) should such detection be desired.

Additionally, the present invention also includes a vaccine comprising a mixture of P29, P30 and P35 antigens and a pharmaceutically acceptable adjuvant. Such a vaccine may be administered if one desires to raise IgG antibodies in a mammal. The present invention also includes a vaccine comprising a mixture of P29, P35 and P66 antigens and a pharmaceutically acceptable adjuvant (e.g., Freund's adjuvant or Phosphate Buffered Saline). Such a vaccine may be administered if one desires to raise IgM antibodies in a mammal. Additionally, the present invention also includes a vaccine comprising a mixture of P29, P30, P35 and P66 antigens as well as a pharmaceutically acceptable adjuvant. This vaccine should be administered if one desires to raise both IgM and IgG antibodies in a mammal.

Kits are also included within the scope of the present invention. More specifically, the present invention includes kits for determining the presence of IgG and/or IgM. In particular, a kit for determining the presence of IgM in a test sample comprises a) a mixture of P29, P35 and P66; and b) a conjugate comprising an antibody (directed against IgM) attached to a signal generating compound capable of generating a detectable signal. The kit may also contain a control or calibrator which comprises a reagent which binds to P29, P35 and P66.

Again, if one desires to detect IgG, rather than IgM, the kit will comprise a mixture of P29, P30 and P35, rather than P29, P35 and P66, as well as an antibody directed against IgG. If one wishes to detect both IgM and IgG, the kit will comprise P29, P30, P35 and P66.

The present invention also includes another type of kit for detecting IgM and/or IgG in a test sample. If utilized for detecting the presence of IgM, the kit may comprise a) an anti-antibody specific for IgM, and b) a mixture of antigens P29, P35 and P66. A control or calibrator comprising a reagent which binds to P29, P35 and P66 may also be included. More specifically, the kit may comprise a) an anti-antibody specific for IgM, and b) a conjugate comprising P29, P35 and P66, the conjugate being attached to a signal generating compound capable of generating a detectable signal. Again, the kit may also comprise a control of calibrator comprising a reagent which binds to P29, P35 and P66.

Additionally, if one desires to detect IgG, rather than IgM, the kit will comprise a mixture of P29, P30 and P35, rather than P29, P35 and P66, as well as anti-antibody specific for IgG. If one wishes to detect both IgM and IgG, the kit may comprise P29, P30, P35 and P66.

Furthermore, the present invention also encompasses a method of distinguishing between acute and chronic infection by use of a portion of the P35 antigen. An individual may be said to have "an acute infection" if the individual has seroconverted to Toxo IgG recently, perhaps within approximately the last 9 months. An acute infection is characterized by at least one of the following: high IgG titer in the Sabin Feldman Dye Test, positive IgM in a double-sandwich IgM ELISA, positive IgA in a double-sandwich IgM ELISA and acute patterns in a Differential Agglutination Test (HS/AC). In contrast, an individual may be said to have "a chronic infection" if the individual has not seroconverted to Toxo IgG recently. A chronic infection is characterized by at least one of the following: low IgG titer in the Sabin Feldman Dye Test, presence or absence of Toxo IgM antibodies (depending upon the commercial test utilized) and chronic patterns in a Differential Agglutination Test (HS/AC).

The difficulties and limitations of conventional serological assays, which detect IgM or IgG antibodies to *T. gondii* using the tachyzoite antigen, in distinguishing an acute toxoplasmosis from a chronic toxoplasmosis, have been described, in detail, above. As was noted, several tests are often employed (e.g., Sabin Feldman Dye test, IgM and IgA ELISAs, and the HS/AC differential agglutination test) to distinguish between an acute and chronic infection. Thus, there has been a need to develop an immunoassay which can accurately distinguish between an acute and chronic toxoplasmosis following an initial positive result for *T. gondii* antibodies. The present invention provides such an immunoassay. In particular, the present invention encompasses a recombinant Toxo P35 IgG immunoassay comprising a portion of the ToxoP35 protein (expressed, for example, in a prokaryotic cell such as *E. coli*), namely rPToxo-P35S (see FIGS. 11A through 11I), corresponding to amino acids 1–135 of P35 (see FIGS. 11A through 11I) (pJ0200-P35S), which detects Toxo IgG antibodies present in an acute infection and does not usually detect Toxo IgG antibodies present in a chronic infection. Thus, it is possible, using the Toxo P35 IgG immunoassay, to determine whether or not an acute toxoplasmosis has occurred during pregnancy. Results of such an immunoassay thereby facilitate an accurate diagnosis of the stage of infection which is important for the clinical management of both the mother and her fetus.

The present invention may be illustrated by the use of the following non-limiting examples:

EXAMPLE 1

General Methodology

Materials and Sources

Restriction enzymes, T4 DNA ligase, calf intestinal alkaline phosphatase (CIAP), polynucleotide kinase, and the Klenow fragment of DNA Polymerase I were purchased from New England Biolabs, Inc. (Beverly, Mass.) or from Boehringer Mannheim Corp. (Indianapolis, Ind.). DnaseI and aprotinin were purchased from Boehringer Mannheim Corp.

DNA and protein molecular weight standards, Daiichi pre-cast gradient polyacrylamide gels were obtained from Integrated Separation Systems, Inc. (Natick, Mass.).

Isopropyl-β-D-thiogalactoside (IPTG), Triton X-100, 4-chloro-1-naphthol, and sodium dodecyl sulfate (SDS) were purchased from BioRad Laboratories (Richmond, Calif.).

Plasma from patients with an acute Toxoplasma infection was obtained from Antibody Systems, Inc., Bedford, Tex.

Horseradish peroxidase (HRPO)-labelled antibodies were purchased from Kirkegaard & Perry Laboratories, Inc. (Gaithersburg, Md.).

EPICURIAN Coli™ XL-1 BLUE (recA1 endA1 gyrA96 thi-1 hsdR17 supE44 relA1 lac [F' proAB lacI$^q$ ZDM15 Tn10 (Tet$^r$)]) supercompetent *E. coli* cells, a DNA isolation kit, a RNA isolation kit, a ZAP™-Cdna GIGAPACK II Gold Cloning kit, a picoBLUE Immunoscreening kit, and Duralose-UV™ membranes, and a ZAP™-Cdna Synthesis kit were obtained from Stratagene Cloning Systems, Inc. (La Jolla, Calif.).

A GENEAMP™ reagent kit and AmpliTaq™ DNA Polymerase were purchased from Perkin-Elmer Cetus (Norwalk, Conn.). Deoxynucleotide triphosphates used in general procedures were from the GeneAmp™ reagent kit.

Supported nitrocellulose membrane was purchased from Schleicher & Schuell (Keene, N.H.).

A nucleotide kit for DNA sequencing with SEQUENASE™ and 7-deaza-Dgtp and SEQUENASE™ version 2.0 DNA Polymerase were obtained from U.S. Biochemical Corp. (Cleveland, Ohio).

A Multiprime DNA labelling kit, alpha-$^{32}$P-Dctp, and a-$^{32}$P-Datp were purchased from Amersham Corp. (Arlington Heights, Ill.).

A PolyA$^+$ Mrna purification kit was purchased from Pharmacia LKB Biotechnology, Inc. (Piscataway, N.J.).

Polygard Cartridge filters, pore size 10 u, were purchased from Millipore Corp., Bedford, Mass.

Luria Broth plates with ampicillin (Lbamp plates) were purchased from Micro Diagnostics, Inc. (Lombard, Ill.).

OPTI-MEM™ Medium, Iscove's Modified Dulbecco's Media, Hank's Balanced Salt Solution, fetal calf serum, phosphate-buffered saline, competent *E. coli* DH5-alpha (F$^-$ ø80dlacZDM15 D(lacZYA-arqF)U169 deoR recA1 endA1 phoA hsdR17($r_K^-$, $m_K^+$) supE44 l$^-$ thi-1 gyrA96 relA1), and ultraPURE agarose were purchased from GIBCO BRL, Inc. (Grand Island, N.Y.).

Bacto-Tryptone, Bacto-Yeast Extract, and Bacto-Agar were obtained from Difco Laboratories (Detroit, Mich.).

NZY Broth was purchased from Becton Dickinson Microbiology Systems (Cockeysville, Md.).

Salmon sperm DNA, lysozyme, ampicillin, N-lauroyl sarcosine, thimerosal, buffers, casein acid hydrolysate, TWEEN 20™ (polyoxyethylenesorbitan monolaurate), diethylpyrocarbonate (DEPC), phenylmethylsulfonylfluoride (PMSF), bovine serum albumin (BSA), urea, glycerol, EDTA, sodium deoxycholate, pyrimethamine, sulfamethoxazole, mouse monoclonal antibody isotyping kits, and inorganic salts were purchased from Sigma Chemical Co. (Saint Louis, Mo.).

OPD (O-phenylenediamine dihydrochloride) and PBS (phosphate buffered saline) was purchased from Abbott Laboratories (Abbott Park, Ill.).

Hydrogen Peroxide ($H_2O_2$) was purchased from Mallinkrodt (Paris, Ky.).

Methanol was purchased from EM Science (Gibbstown, N.J.).

Microtiter Maxisorp plates were purchased from NUNC, Inc. (Naperville, Ill.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 Ml/L glycerol, adjusted Ph to 7.2 with sodium hydroxide.

"Tris-buffered saline" or "TBS" consisted of 20 Mm Tris, 500 Mm NaCl at Ph 7.5.

"Tris-buffered saline TWEEN 20™" or "TBST" consisted of TBS plus 0.05% TWEEN 20.

"Rubazyme specimen dilution buffer" or "Rubazyme SDB" consisted of 100 Mm Tris at Ph 7.5 with 135 Mm NaCl, 10 Mm EDTA, 0.2% TWEEN 20™, 0.01% thimerosal and 4% bovine calf serum.

"Rubazyme conjugate diluent dilution buffer" consisted of 100 Mm Trisat Ph 7.5 with 135 Mm NaCl, 0.01% thimerosal and 10% bovine calf serum.

"Membrane blocking solution" consisted of 1% BSA, 1% casein acid hydrolysate, 0.05% Tween 20 in TBS.

"TE buffer" consisted of 10 Mm Tris and 1 Mm EDTA at Ph 8.0.

"TEM lysis buffer" consisted of 50 Mm Tris, 10 Mm EDTA and 20 Mm magnesium chloride at Ph 8.5.

"PTE buffer" consisted of 50 Mm Tris and 10 Mm EDTA at Ph 8.5.

Parasite, Cell, and Mouse Lines

The RH strain of *T. gondii* (ATCC 50174) and the HeLa S3 cell line (ATCC CCL 2.2) were obtained from the American Type Culture Collection, 10801 University Boulevard, Manassas, Va. 20110-2209. The TS4 strain of *T. gondii* was also available from the American Type Culture Collection and from other sources. The Swiss mouse strain CD1 was obtained from Charles River Laboratories, Wilmington, Mass. Parasites were maintained by serial passage in the peritoneal cavity of Swiss mice. Tachyzoites were collected from the peritoneal cavity and used to inoculate a primary suspension culture of HeLa S3 cells. This infected suspension culture was grown for 2–4 days at 37° C. in Iscove's Modified Dulbecco's Media and then used to inoculate a secondary suspension culture of uninfected HeLa S3 cells. This secondary infected suspension culture was grown for 2–4 days at 37° C. in OPTI-MEM Reduced Serum Medium and used as a source of tachyzoites for screening monoclonal antibodies and for the preparation of DNA, RNA, and total tachyzoite protein.

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in manipulation of DNA and RNA, for polymerase chain reaction (PCR) DNA synthesis and for DNA sequencing. Standard procedures were used for Western and Southern Blots, partial restriction enzyme digestion of Toxoplasma genomic DNA with Sau 3AI, construction of a Toxoplasma genomic library, miniprep and large scale preparation of plasmid DNA from *E. coli*, preparation of phage lysate DNA from *E. coli* cells infected with phage lambda, preparation of *E. coli* lysates for the absorption of anti-*E. coli* antibodies, phenol-chloroform extraction and ethanol precipitation of DNA, restriction analysis of DNA on agarose gels, purification of DNA fragments from agarose gels, filling the recessed 3' termini created by digestion with restriction enzymes using the Klenow fragment of DNA Polymerase I, and ligation of DNA fragments with T4 DNA ligase. (Maniatis et al., *Molecular Cloning: A Laboratory Manual*, $2^{nd}$ ed. (Cold Spring Harbor Laboratory Press, New York, 1989)).

DNA fragments for cloning into plasmids that were generated by PCR amplification, were extracted with phenol-chloroform and precipitated with ethanol prior to restriction enzyme digestion of the PCR reaction mixture. Oligonucleotides for PCR and DNA sequencing were synthesized on an Applied Biosystems Oligonucleotide Synthesizer, model 380B or 394, per the manufacturer's protocol.

Mouse monoclonal antibody directed against the CKS protein was obtained by immunization of mice with purified rpHCV-23 (CKS-BCD), described in International Application No. WO93/04088 by Dailey et al. The proteins used for immunization were approximately 90% pure as determined by SDS-PAGE. The procedure for the immunization of mice, cell fusion, screening and cloning of monoclonal antibodies, and characterization of monoclonal antibodies were as described in Published International Application No. WO92/08738 by Mehta et al.

EXAMPLE 2

Isolation of Toxoplasma DNA, RNA, Protein and Synthesis of Cdna

A 10 L secondary suspension culture of HeLa cells infected with the RH strain of *T. gondii* was grown to a tachyzoite density of approximately $1 \times 10^7$ per ml and filtered through a 10 m Millipore Polygard cartridge filter to remove HeLa cells from the tachyzoites. The tachyzoite filtrate obtained contained less than 1% HeLa cells. The tachyzoites were then concentrated by centrifugation, washed and resuspended in 1× Hank's Buffer. The tachyzoite concentrate was then pipetted dropwise into liquid nitrogen, and the frozen tachyzoite pellets were recovered and stored at −80° C. until further use. The tachyzoite pellets were converted to tachyzoite powder by grinding the pellets to a fine powder using a mortar and pestle chilled with dry ice and liquid nitrogen. The tachyzoite powder was subsequently used for the isolation of tachyzoite nucleic acid and protein as described below.

Step A: Isolation of Toxoplasma DNA

Total Toxoplasma DNA was isolated from the tachyzoite powder using the Stratagene DNA extraction kit. The tachyzoite powder was dissolved in Solution 2, and total DNA was isolated following the kit's protocol. After ethanol precipitation and resuspension of the DNA in TE buffer, undissolved DNA and contaminating polysaccharides were removed by centrifugation at 200,000×g for 1 hr.

Step B: Isolation of Toxoplasma RNA

Total Toxoplasma RNA was isolated from the tachyzoite powder using the Stratagene RNA isolation kit. The tachyzoite powder was dissolved in Solution D, and total RNA was isolated following the kit's protocol. After ethanol precipitation and resuspension of the RNA in DEPC-treated water, polyA$^+$ RNA was selected with an oligo-Dt column using a Pharmacia Mrna isolation kit. The purified Mrna was concentrated by ethanol precipitation and stored in DEPC-treated water at −80° C. until further use.

Step C: Isolation of Total Toxoplasma Protein

Total Toxoplasma protein was isolated from the tachyzoite powder by dissolving the powder in SDS-PAGE loading buffer and boiling the sample for 5 min. The protein preparation was stored at −20° C. until further use.

Step D: Synthesis of Toxoplasma Cdna

Purified Toxoplasma Mrna was used as a template for the synthesis of Cdna using the Stratagene ZAP-Cdna Synthesis kit. The first strand was synthesized using Moloney-Murine Leukemia Virus Reverse Transcriptase and a 50 mer primer which included an Xho I restriction enzyme site and an poly-Dt tract. The reaction mix included the analog 5-methyl Dctp to protect the Cdna from restriction enzymes used in subsequent cloning steps. The second strand was synthesized using Rnase H and DNA polymerase I. The Cdna was then ethanol precipitated and resuspended in water and stored at −20° C. until further use as a template for PCR amplification and for construction of a Toxoplasma Cdna library.

EXAMPLE 3

Cloning Strategy for Genes Encoding Toxoplasma Antigens

The immune response that is generated by human patients with Toxoplasmosis is targeted against several *T. gondii* proteins and varies by individual and by the disease stage. Hence, a Toxoplasma immunoassay which is composed entirely of purified protein antigens will require more than one protein serological target to accurately detect serum antibody to *T. gondii* in a population of Toxoplasma infected individuals. In order to identify additional Toxoplasma antigens which are relevant for human diagnostic testing, a two-tiered cloning strategy for genes encoding Toxoplasma antigens was undertaken. The first-tier consisted of cloning known genes encoding Toxoplasma antigens, by using the published DNA sequences for these genes. The second-tier consisted of cloning novel, previously undescribed genes encoding Toxoplasma antigens, by using pooled human plasma from patients with toxoplasmosis to screen a Toxoplasma Cdna library. The genes cloned in the first tier were then used as DNA probes to screen the genes cloned in the second tier for uniqueness.
Step A: Cloning of Toxoplasma Genes Encoding Known Toxoplasma Antigens The CKS expression vector Pjo200 described in U.S. patent application Ser. No. 08/742,619 of Maine and Chovan allows the fusion of recombinant proteins to the CMP-KDO synthetase (CKS) protein. The DNA gene sequence which encodes for the structural protein CKS (also known as the kdsB gene) is published in Goldman et al., J. Biol. Chem. 261:15831 (1986). The amino acid sequence of CKS includes 248 amino acid (aa) residues and is described in Goldman et al., supra. The Pjo200 vector contained DNA encoding the sequence of the first 240 amino acids from the original kdsB gene followed by an additional 20 amino acids encoded for by the polylinker DNA sequence, for a total of 260 amino acids.

Oligonucleotide primers for use in the PCR amplification of known genes encoding Toxoplasma antigens were designed based on published DNA sequences. Each pair of PCR primers were "tailed" with additional DNA sequences to include restriction enzyme sites for subsequent cloning into the Pjo200 CKS expression vector. PCR amplification of each Toxoplasma gene with the appropriate primers was carried out using the GeneAmp reagent kit and AmpliTaq DNA Polymerase purchased from Perkin-Elmer Cetus, Norwalk, Conn., following the kit's protocol. Approximately 20 ng of Toxoplasma Cdna prepared in Example 2D or 20 ng of Toxoplasma genomic DNA prepared in Example 2A (for P66 genomic clone only) was used in each reaction. The amplification cycles were 1 cycle of 95° C. for 120 sec., followed by 35 cycles of 95° C. for 60 sec., 55° C. for 60 sec., 72° C. for 120 sec., followed by 1 cycle at 72° C. for 300 sec., followed by a soak cycle at 4° C. The PCR products obtained from the amplification reaction were then digested with the appropriate restriction enzymes, purified on agarose gels, ligated into the Pjo200 vector cut with the appropriate restriction enzymes and transformed into the Epicurean Coli XL-1 Blue Supercompetent *E. coli* cells following the kit protocol. Correct clones were confirmed by DNA sequence analysis of the cloned Toxoplasma DNA. The DNA sequences of the oligonucleotide primers used for the PCR amplification of the following Toxoplasma genes are shown below and how they were cloned into the Pjo200 CKS vector:

Toxo P22 (SAG2) Gene (Prince et al. (1990) Mol. Biochem. Parasitol 43, 97–106)
Sense Primer [SEQ ID NO:1]:

5'-CGCA
<u>GAATTC</u>GATGTCCACCACCGAGACGCCAGCGCCCA-
TTGA-3'

(EcoRI site is underlined)
Antisense Primer [SEQ ID NO:2]:

5'-CCCG
<u>GGATCC</u>TTACACAAACGTGATCAACAAACCTGCGA-
GACC-3'

(BamH-I site is underlined)
Region Cloned: Nucleotides 260–739 of the Toxo P22 gene cloned into the EcoRI/BamH-I sites of Pjo200 to yield plasmid Pjo200-P22.

Toxo P24 (GRA1) Gene (Cesbron-Delauw et al. (1989) Proc. Nat. Acad. Sci. 86, 7537–7541)
Sense Primer [SEQ ID NO:3]:

5'-GGCC<u>GAATTC</u>GATGGCCGAAGGCGGCGACAACCAGT-3'

(EcoRI site is underlined)
Antisense Primer [SEQ ID NO:4]:

5'-GCCC<u>GGATCC</u>TTACTCTCTCTCTCCTGTTAGGAACCCA-3'

(BamH-I site is underlined)
Region Cloned: Nucleotides 685–1183 of the Toxo P24 gene cloned into the EcoRI/BamH-I sites of Pjo200 to yield plasmid Pjo200-P24.

Toxo P25 Gene (Johnson et al. (1991) Gene 99, 127–132)
Sense Primer [SEQ ID NO:5]:

5'-GGC
<u>GAATTC</u>GATGCAAGAGGAAATCAAAGAAGGGGTGGA-3'

(EcoRI site is underlined)
Antisense Primer [SEQ ID NO:6]:

5'-CGCAC<u>TCTAGA</u>TCACCTCGGAGTCGAGCCCAAC-3'

(XbaI site is underlined)
Region Cloned: Nucleotides 7–288 of the Toxo P25 gene cloned into the EcoRI/XbaI sites of Pjo200 to yield plasmid Pjo200-P25.

Toxo P28 (GRA2) Gene (Prince et al. (1989) Mol. Biochem. Parasitol. 34, 3–13)
Sense Primer [SEQ ID NO:7]:

5'-GGCGAATTCGATGAGCGGTAAACCTCTTGATGAG-3'

(EcoRI site is underlined)
Antisense Primer [SEQ ID NO:8]:

5'-CGCTAGGATCCTTACTGCGAAAAGTCTGGGAC-3'

(BamH-I site is underlined)
Region Cloned: Nucleotides 489–924 of the Toxo P28 gene cloned into the EcoRI/BamH-I sites of Pjo200 to yield plasmid Pjo200-P28.

Toxo P30 (SAG1) Gene (Burg et al. (1988) J. Immunol. 141, 3584–3591)
Sense Primer [SEQ ID NO:9]:

5'-GGCGAATTCGATGCTTGTTGCCAATCAAGTTGTCACC-3'

(EcoRI site is underlined)
Antisense Primer [SEQ ID N:10]:

5'-CGCTAGGATCCTCACGCGACACAAGCTGCGA-3'

(BamH-I site is underlined)
Region Cloned: Nucleotides 464–1318 of the Toxo P30 gene cloned into the EcoRI/BamH-I sites of Pjo200 to yield plasmid Pjo200-P30.

Toxo P35 Gene (Knapp et al. (1989) EPA 431541A2)
Sense Primer [SEQ ID NO:11]:

5'-GACGGCGAATTCGATGAACGGTCCTTTGAGTTATC-3'

(EcoRI site is underlined)
Antisense Primer [SEQ ID NO:12]:

5'-CGCTAGGATCCTTAATTCTGCGTCGTTACGGT-3'

(BamH-I site is underlined)
Region Cloned: Nucleotides 91–822 of the Toxo P35 gene cloned into the EcoRI/BamH-I sites of Pjo200 to yield plasmid Pjo200-P35.

Toxo P35 Gene Subclone #1 (1-135aa)

(Knapp et al. (1989) EPO 431541A2)
Sense Primer [SEQ ID NO:13]:

5'-GACGGCGAATTCGATGAACGGTCCTTTGAGTTATC-3'

(EcoRI site is underlined)
Antisense Primer [SEQ ID NO:14]:

5'-CGCTAGGATCCTCAATGGTGAACTGCCGGTATCTCC-3'

(BamH-I site is underlined)
Region Cloned: Nucleotides 91–495 of the Toxo P35 gene cloned into the EcoRI/BamH-I sites of Pjo200 to yield plasmid Pjo200-P35S.

Toxo P41 (GRA4) Gene (Mevelec et al. (1992) Mol. Biochem. Parasitol. 56, 227–238)
Sense Primer [SEQ ID NO:15]:

5'-GGCGAATTCGATGGGTGAGTGCAGCTTTGGTTCT-3'

(EcoRI site is underlined)
Antisense Primer [SEQ ID NO:16]:

5'-CGCACTCTAGATCACTCTTTGCGCATTCTTTCCA-3'

(XbaI site is underlined)
Region Cloned: Nucleotides 133–1107 of the Toxo P41 gene cloned into EcoRI/XbaI sites of Pjo200 to yield plasmid Pjo200-P41.

Toxo P54 (ROP2) Gene (Saavedra et al. (1991) J. Immunol. 147, 1975–1982)
Sense Primer [SEQ ID NO:17]:

5'-GCCTGAATTCGATGCACGTACAGCAAGGCGCTGGCGTTGT-3'

(EcoRI site is underlined)
Antisense Primer [SEQ ID NO:18]:

5'-CGCTAGGATCCTCAGAAGTCTCCATG-GCTTGCAATGGGAGGA-3'

(Cloned as a blunt end)
Region Cloned: Nucleotides 85–1620 of the Toxo P54 gene cloned into the EcoRI/SmaI sites of Pjo200 to yield plasmid Pjo200-P54.

Toxo P66 (ROP1) Gene (Knapp et al. (1989) EPA 431541A2)
(Ossorio et al. (1992) Mol. Biochem. Parasitol. 50, 1–15.
Sense Primer [SEQ ID NO:19]:

5'-GGCGAATTCGATGAGCCACAATGGAGTCCCCGCTTATCCA-3'

(EcoRI site is underlined)
Antisense Primer [SEQ ID NO:20]:

5'-CGCTAGGATCCTTATTGCGATCCATCATCCTGCTCTCTTC-3'

(BamH-I site is underlined)
Region Cloned: Nucleotides 122–1330 of the Toxo P66 gene cloned into the EcoRI/BamH-I sites of Pjo200 to yield plasmid Pjo200-P66 using Toxoplasma Cdna as template. Nucleotides 122–1330 of the Toxo P66 gene cloned into the EcoRI/BamH-I sites of Pjo200 to yield plasmid Pjo200-P66g using Toxoplasma genomic DNA as template.

Toxo P68 Gene (Knapp et al. (1989) EPA 431541A2)
Sense Primer [SEQ ID NO:21]:

5'-ACCCGAATTCGATGACAGCAACCGTAGGATTGAGCCAA-3'

(EcoRI site is underlined)
Antisense Primer [SEQ ID NO:22]:

5'-CGCTGGATCCTCAAGCTGCCTGTTCCGCTAAGAT-3'

(BamH-I site is underlined)

Region Cloned: Nucleotides 294–1580 of the Toxo P68 gene cloned into the EcoRI/BamH-I sites of Pjo200 to yield plasmid Pjo200-P68.

Step B: Construction and Immunoscreening of a Toxoplasma Cdna Library

A Toxoplasma Cdna library was constructed in the UNI-ZAP XR vector using the Stratagene ZAP-Cdna Synthesis kit and ZAP-Cdna Gigapack II Gold Cloning kit. The Cdna produced in Example 2D was further processed using the kit protocols as briefly outlined below. The Cdna ends were blunted with T4 DNA polymerase, and EcoRI restriction site adapters were ligated to the blunt-ended Cdna. The RI adaptors ligated to the Cdna were then kinased with T4 Polynucleotide Kinase. The Cdna was digested with the restriction enzymes EcoRI and XhoI and then ligated to the phage lambda UNIZAP XR vector arms. The Cdna is cloned unidirectionally into this vector, resulting in the 5' end of the Cdna located downstream of the lacZ gene. If the coding sequence of the Cdna is in frame with the lacZ gene, a lacZ-Toxo fusion protein will be expressed. The UNIZAP XR-Toxo Cdna ligation mixture was packaged into phage in vitro, and a primary Toxoplasma Cdna phage library was obtained with 660,000 members. This library was amplified and checked for the size and frequency of the cloned Cdna inserts by converting a dozen random phage clones to E. coli phagemid (plasmid) clones using the Stratagene in vivo subcloning protocol from the ZAP-Cdna Synthesis kit. This procedure excises the cloned Cdna insert and the Pbluescript plasmid from the phage resulting in a Pbluescript plasmid clone containing the cloned Cdna. Miniprep DNA was made from the phagemid clones and analyzed with restriction enzymes on DNA agarose gels. Greater than 90% of the phagemid clones contained insert DNA with an average size of 0.8 Kb. This library was used for immunological screening with pooled plasma obtained from patients with Toxoplasmosis as described below.

Plasmas obtained from individuals in the acute phase of Toxoplasmosis infection were pooled. Samples used for this pool were tested by the Abbott Imx Toxo IgM and Toxo IgG immunoassays (Abbott Laboratories, Abbott Park, Ill.), and only samples that contained IgM antibodies and no detectable levels of IgG antibody were pooled. Prior to immunoscreening, the pooled plasma was treated to remove E. coli cross-reactive antibodies. The procedure followed was a modification of the protocol described in the Stratagene picoBLUE immunoscreening kit. Pooled plasma was initially diluted 1:5 in Rubazyme specimen dilution buffer and E. coli cross-reactive antibodies were removed by incubating the diluted pool plasma with several nitrocellulose filters coated with E. coli lysate as described in the kit protocol. After absorption of E. coli antibodies, the plasma pool was stored at 4° C. until further use.

The Toxoplasma Cdna library was immunologically screened following a modification of the Stratagene picoBLUE Immunoscreening kit protocol. Briefly, recombinant phage absorbed to the XL-1 Blue strain of E. coli were plated onto pre-warmed 150 mm NZY plates at a density of 20,000 phage per plate and incubated for 3.5 hrs. at 42° C. Duralose UV membranes pretreated with 10 Mm IPTG and dried were then overlayed on each plate and incubated for an additional 4 hrs. at 37° C. The filters were oriented by piercing them with an 18 gauge needle, removed from the plate and washed 3× with TBST buffer at room temperature, 10 min. per wash. The filters were then washed once for 10 min. with TBS buffer at room temperature and blocked overnight at 4° C. in membrane blocking solution. The next day the filters were incubated for 2 hrs. at room temperature with the acute phase plasma pool (at 1:40 dilution in Rubazyme SDB). The filters were then washed 2× with TBST for 10 min. per wash and once with TBS for 10 min. and then incubated for 1 hr. at room temperature with goat anti-Human IgM (H+L) horseradish peroxidase-labelled antibody. The filters were washed again as before and developed for 10 min. in HRP color development solution. The filters were then extensively washed with tap water to stop the color development reaction, and plaques which gave a strong blue color were subsequently plaque purified twice and retested for immunoreactivity against the appropriate pool of plasma. Approximately 130,000 plaques were screened with the pooled acute phase plasma with the isolation of 4 positive clones. These phage clones were converted to plasmid clones using the Stratagene in vivo subcloning protocol from the ZAP-Cdna Synthesis Kit and further characterized as described below.

Step C: Characterization of the Immunopositive Clones Isolated With the Acute Phase Plasma Pool The 4 immunopositive clones isolated with the acute phase plasma pool were designated Pgm610, Pgm611, Pgm612, and Pgm613 and were analyzed with restriction enzymes on DNA agarose gels. Clones Pgm610 and Pgm612 contained a 1.1 Kb insert of DNA, clone Pgm611 contained a 0.7 Kb insert of DNA, and clone Pgm613 contained a 1.3 Kb insert of DNA. The Cdna inserts contained in these clones were removed from the Pbluescript vector by restriction enzyme digestion and purified on DNA agarose gels. These 4 purified Cdna inserts were individually labelled with alpha-$^{32}$P-Dctp using the Multiprime DNA labelling kit and protocol from Amersham for hybridization to colony filters and genomic Toxoplasma DNA. Filters for colony hybridization were prepared by gridding E. coli clones containing the cloned Toxoplasma genes described in Examples 3A and 3B onto Duralose UV membranes overlaid on Lbamp plates. These plates were grown overnite at 37° C., and the next day the E. coli colonies were lysed with alkali and prepared for DNA colony hybridization as described in GENERAL METHODS. After hybridization and washing, the hybridization signal was visualized by autoradiography with the result that all 4 immunopositive clones were homologous to one another and are non-homologous to the other 10 genes tested (see Example 3A). In order to determine the homology between the immunopositive clones and between Toxoplasma genomic DNA, the following Southern blot experiment was performed as described in GENERAL METHODS. Toxoplasma genomic DNA and two of the immunopositive clones were digested with restriction enzymes, run on DNA agarose gels, transferred to nitrocellulose and probed with purified radioactively-labelled Cdna inserts from clones Pgm611 and Pgm613. After hybridization and washing, the hybridization signal was visualized by autoradiography with the result that both clones were homologous to one another and all hybridized to the genomic blot of Toxoplasma DNA. Therefore, these 4 immunopositive clones contained the same Toxoplasma gene encoding a novel antigen which was designated $P_{novel2}$.

EXAMPLE 4

Construction of CKS-$P_{novel2}$ Expression Vector Based on Pjo200

The gene encoding the $P_{novel2}$ antigen was subcloned into the Pjo200 vector in order to produce adequate levels of fusion protein for further analysis. Since the reading frame of the lacZ gene in the Pbluescript vector and the reading frame of the CKS gene in the Pjo200 vector are the same, presence of the EcoRI site at the juncture of the CKS and Toxoplasma genes ensured that the Toxoplasma gene was fused translationally in frame with the CKS gene. In order to remove the Cdna insert from the Pbluescript vector and subclone it into the Pjo200 vector, the following digests were performed:

The CKS expression vector Pjo200 described in Example 3A was digested with EcoRI and SmaI and the vector backbone was purified on an agarose gel in preparation for subcloning. Plasmid DNA from the largest $P_{novel2}$ clone Pgm613 was digested with Asp718 and then treated with the Klenow fragment of DNA Polymerase I to render the ends blunt-ended. Subsequently, the DNA was extracted and then digested with EcoRI, and the 1.3 Kb EcoRI/Asp718 (Klenow) DNA fragment from Pgm613 was purified on an agarose gel and ligated to Pjo200/EcoRI/SmaI overnight at 16° C.

The next day, the ligation mixture was transformed into competent XL-1 Blue cells. Miniprep DNA was prepared from the transformants and screened for the presence of the 1.3 Kb DNA fragment inserted at the EcoRI/SmaI sites of Pjo200. The correct CKS-$P_{novel2}$ clone identified by restriction analysis was designated Pjo200-$P_{novel2}$.

EXAMPLE 5

Expression of Recombinant Toxo Antigens and CKS in E. coli

Step A: Expression of cloned genes in E. coli

Bacterial clones Pjo200-P22, Pjo200-P24, Pjo200-P25, Pjo200-P28, Pjo200-P30, Pjo200-P35S, Pjo200-P41, Pjo200-66g, Pj0200-68 and Pjo200-$P_{novel2}$ expressing the CKS fusion proteins rpJO200-P22, rpJO200-P24, rpJO200-P25, rpJO200-P28, rpJO200-P30, rpJO200-P35S, rpJO200-P41, rpJO200-66g, Rpj0200-68 and rpJO200-$P_{novel2}$ of Examples 3 and 4 and the control bacterial strain expressing unfused CKS were grown in "SUPERBROTH II" media containing 100 ug/ml ampicillin to log phase, and the synthesis of the CKS-Toxo fusion protein and unfused CKS was induced by the addition of IPTG as previously described (Robinson et al. (1993) J. Clin. Micro. 31, 629–635). After 4 hours post-induction, the cells were harvested, and the cell pellets were stored at −80° C. until protein purification occurred.

Step B: Purification of Recombinant Toxo Antigens and CKS Protein

Insoluble recombinant antigens rpJO200-P22, rpJO200-P25, rpJO200-P30, rpJO200-P35S, rpJO200-P41, rpJO200-66g, and rpJO200-$P_{novel2}$ were purified after lysis from cell paste by a combination of detergent washes followed by solubilization in 8M urea (Robinson et al. (1993) J. Clin. Micro. 31, 629–635). After solubilization was complete, these proteins were filtered through a 0.2 u filter and further purified by chromatography on Sephacryl S-300 columns. The appropriate column fractions were pooled for each protein and stored at 2–8° C. for evaluation by microtiter ELISA. Soluble rpJO200-P24, rpJO200-P28, rpJO200-P68, and unfused CKS proteins were purified after cell lysis by ammonium sulfate precipitation followed by ion-exchange chromatography. The appropriate column fractions were pooled for each protein, dialyzed against the appropriate buffer, and stored at 2–8° C. for evaluation by microtiter ELISA.

EXAMPLE 6

Evaluation of Human Sera with the Recombinant Toxo Antigens in Microtiter ELISA

Step A: Human Sera for Testing

The tests used for determining the presence of IgG and IgM antibody in sera were the Abbott Toxo-G and Toxo-M MEIA assays, respectively. Twenty-four Toxo IgG positive sera, eighteen Toxo IgM positive sera, and nineteen sera negative for Toxo IgG and IgM antibody were evaluated using the recombinant Toxo antigens in Microtiter ELISA.

Step B: Evaluation of Human Sera in the Recombinant Toxo Antigen Microtiter ELISA Purified recombinant Toxo antigens (Example 5B) were individually diluted to 5.0 ug per ml in PBS, and 0.1 ml of each antigen was added to separate wells of microtiter Maxisorp plates. Control wells for each sera were coated with E. coli lysate at 5.0 ug per ml. Plates were incubated at 37° C. for 1 hr and stored overnight at 4° C. The next day, the plates were washed three times with distilled water and blocked for 2 hrs at 37° C. with 0.2 ml of blocking solution (3% fish gelatin, 10% fetal calf serum in PBS, 0.22 u). The plates were then washed three times with distilled water and ready for incubation with serum. Each serum specimen was tested in duplicate with each antigen at a 1:200 dilution into Rubazyme SDB containing 2% E. coli lysate. After adding 0.1 ml of diluted specimen to each well, the plates were incubated for 1 hr. at 37° C. The plates were then washed three times with PBS-Tween and three times with distilled water. Bound human IgG and IgM were detected by using goat anti-human IgG-HRPO and IgM-HRPO conjugates, respectively, diluted 1:1,000 in Rubazyme conjugate diluent buffer and filtered. After addition of 0.1 ml of the appropriate diluted conjugate, the plates were incubated for 1 hr. at 37° C. and washed three times with PBS-Tween and three times with distilled water. The OPD color development reagent was prepared per manufacturer's directions and 0.1 ml was added to each well. After 2 minutes, the color development reaction was stopped by adding 0.1 ml of 1N sulfuric acid, and the plate was read in a microtiter plate reader. The net OD was obtained by subtracting the OD for the E. coli lysate control from that of the test with each recombinant antigen. The cut-off for these assays was between 2 to 3 standard deviations from the mean of the negative population for each antigen.

The results of the evaluation of human sera in the recombinant microtiter ELISA are shown in Table 1 for detection of Toxoplasma-specific IgG antibody and in Table 2 for detection of Toxoplasma-specific IgM antibody. The performance of each antigen was ranked in decreasing order of the antigen with the largest number of positive specimen results per total number of positive (IgM or IgG) specimens tested.

TABLE 1

Relative rank of Antigen Performance in Microtiter IgG ELISA

| | Immunoreactivity | |
|---|---|---|
| | IgG− | IgG+ |
| | # Pos Results/Total # IgG− | # Pos Results/Total # IgG+ |
| Antigen | Specimens Tested | Specimens Tested |
| P68 | 1/19 | 16/24 |
| P35S | 1/19 | 14/24 |
| P24 | 0/19 | 14/24 |
| P30 | 2/18 | 13/24 |
| Pnovel2 (P29) | 1/19 | 13/24 |
| P22 | 0/19 | 13/24 |
| P30 | 2/18 | 13/24 |
| P41 | 0/19 | 10/24 |
| P25 | 1/19 | 10/24 |
| P28 | 1/19 | 10/24 |
| P66 | 2/19 | 9/24 |

TABLE 2

Relative rank of Antigen Performance in Microtiter IgM ELISA

| | Immunoreactivity | |
|---|---|---|
| | IgM⁻ | IgM⁺ |
| Antigen | # Pos Results/Total # IgM− Specimens | # Pos Results/Total # IgM+ Specimens |
| P66 | 1/18 | 17/18 |
| P35 (1–135) | 0/18 | 15/18 |
| Pnovel2 (P29) | 0/19 | 10/18 |
| P68 | 0/19 | 5/18 |
| P22 | 0/19 | 5/18 |
| P28 | 1/18 | 4/18 |
| P41 | 0/18 | 3/18 |
| P25 | 0/19 | 3/18 |
| P30 | 1/18 | 2/18 |
| P24 | 1/19 | 0/18 |

As can be seen from Table 1, there was no single recombinant Toxo antigen capable of detecting as positive all 24 IgG positive specimens. Hence, an immunoassay employing some combination of the antigens listed in Table 1 is required to detect all the IgG positive specimens.

As can be seen from Table 2, there was no single recombinant Toxo antigen capable of detecting as positive all 18 IgM positive specimens. Hence, an immunoassay employing some combination of the antigens listed in Table 2 is required to detect all the IgM positive specimens.

EXAMPLE 7

Generation of a Monoclonal Antibody Reactive With CKS-P$_{novel2}$ Antigen

Step A: Immune Response Study in Mice and Generation of Hybridomas

Animals, including mice, rats, hamsters, rabbits, goats and sheep may be infected with a lethal dose of tachyzoites, rescued from death with drug therapy and later used for hybridoma development. There are two hydbridoma development advantages for using this process that otherwise would not be possible. The first advantage is that time is allowed for a diverse repertoire of antibodies to be generated against native $T.$ gondii (or Borrelia burgdorferi, Schistosoma sp., for example, Schistosoma treponema, or sporozoans other than $T.$ gondii, for example, members of the genus Plasmodium (e.g., $P.$ vivax and $P.$ falciparum) and other possible members of the genus Toxoplasma)), and the second advantage is that the rescue allows time for affinity maturation of the immune response.

In the present experiment, Swiss mice were infected intraperitonally with $2.5 \times 10^7$ tachyozoites of $T.$ gondii strain TS4. Five days later mice were treated orally with 10 mg pyrimethamine and 200 mg sulfamethoxazole per kg daily for 10 days. (This technique can be repeated every 6–8 weeks if desired.) After 12 additional weeks, these mice were injected intravenously with $1.2 \times 10^7$ sonicated tachyzoites 3 days prior to fusion to minimize the biohazardous status. One hundred percent of the mice survived (providing evidence of a humane method). Resulting hybrids from the PEG mediated fusion of splenocytes and the SP2/0 myeloma were screened on the sonicated tachyzoites and CKS-P$_{novel2}$ antigen (Kohler, G. and Milstein, C. (1975) Nature 256, 495–497; Kohler, G. and Milstein, C. (1976) Eur. J. Immunol. 6, 511–519; Goding, J. (1986) Monoclonal Antibodies: Principles and Practice. 2$^{nd}$ Ed. Academic Press London).

It should also be noted that monoclonal antibodies may be produced by immunizing mice by intraperitoneal infection with $T.$ gondii (Mineo et al. (1993) J. Immunol. 150, 3951–3964; Handman et al. (1980) J. Immunol. 124, 2578–2583; Grimwood and Smith (1992) Exp. Parasitol. 74, 106–111) or with fractions of $T.$ gondii (Prince et al. (1990) Mol. Biochem. Parasitol. 43, 97–106). Fusion of spleen cells and myeloma cells may then be carried out directly, subsequent to immunization, without a drug therapy step (see, e.g., Kohler and Milstein, supra (1975)).

Step B: Screening and Isolation of a Monoclonal Antibody to rpCKS-P$_{novel2}$

Bacterial clone Pjo$^{200}$-P$_{novel2}$ expressing the CKS-P$_{novel2}$ fusion protein of Example 4 (rpJO200-P$_{novel2}$) and the control bacterial strain expressing unfused CKS were grown in Superbroth II media containing 100 ug/ml ampicillin to log phase, and the synthesis of the CKS-Toxo fusion protein and unfused CKS was induced by the addition of IPTG as previously described in Example 5A. In preparation for screening hybridoma fluids obtained in Example 7A, cell pellets were thawed, resuspended in 10 ml of PBS and sonicated for 0.5 min in an icewater bath. The antigen preparation was diluted 1:40 in 0.05 M sodium carbonate-bicarbonate, Ph 9.6, containing 15 Mm sodium azide after which 0.1 ml of this suspension was placed in wells of NUNC Maxisorb microtiter plates. When tachyzoites were tested, $3 \times 10^6$ sonicated tachyzoites were added to wells. Plates were incubated at 37° C. for 1 hr, stored 1 to 3 days at 4° C., and washed three times with distilled water. Hybridoma fluids obtained in Example 7A were diluted 1:10 in Rubazyme SDB. The remainder of the ELISA was performed as described above in Example 6B except bound antibody was detected by mixture of horseradish peroxidase-conjugated goat anti-mouse IgG and IgM, each diluted to 1.0 ug per ml in Rubazyme conjugate diluent buffer.

Positive hybridoma clones were cloned by limiting dilution, and hybridoma fluid was retested by microtiter ELISA containing rpJO200-P$_{novel2}$, unfused CKS, and sonicated tachyzoites. One highly reactive monoclonal antibody clone was isolated which was designated Toxo Mab 5-241-178, which reacted very strongly with sonicated tachyzoites and rpJO200-P$_{novel2}$ but showed no reactivity to unfused CKS. This hybridoma clone was found to produce IgG type antibodies as determined using a mouse monoclonal antibody isotyping kit from Sigma.

Step C: Identification of the P$_{novel2}$ Gene Encoding the Toxoplasma P29 Antigen Using Toxo Mab 5-241-178

Total Toxoplasma protein prepared as described in Example 2C was loaded onto an 4–20% gradient Daiichi SDS-PAGE gel along with protein standard molecular weight markers, and transferred to nitrocellulose as described in General Methods. The Western blot was probed with the Toxo Mab 5-241-178 antibody, and the blot was visualized with a goat anti-mouse IgG-HRPO conjugate followed by BioRad Color Development Reagent (4-chloro-1-naphthol and hydrogen peroxide) per manufacturer's directions. A single protein band of 29,000 molecular weight from the Toxoplasma protein prepared from tachyzoites was immunoreactive with the Toxo Mab 5-241-178 indicating that the P$_{novel2}$ gene cloned in plasmid Pgm613 (Example 3C) and Pjo200-P$_{novel2}$ (Example 4) encodes the P29 antigen of Toxoplasma.

EXAMPLE 8

DNA Sequence of Clone Pgm613 and Deduced Amino Acid Sequence

The 1.3 Kb EcoRI/XhoI insert of Toxoplasma Cdna contained in Pgm613 was sequenced as described in General Methods. The DNA sequence (1268 bp) [SEQ ID NO:23] and the deduced amino acid sequence (228 aa) [SEQ ID NO:24] in-frame with the lacZ gene are shown in FIGS. 1A, 1B and 1C. The open reading frame (nucleotide position 2 to 685) present in this sequence can code for a protein of approximately 25,000 molecular weight. The first ATG present in the DNA sequence is located at nucleotide position 80 and is not surrounded by sequences fulfilling the criteria for initiation of translation (Kozak, M. (1986) Cell 44, 283–292) and is probably not the initiator methionine residue. Hence, it is likely that the insert of Toxoplasma Cdna present in clone Pgm613 is not full-length.

Genebank's non-redundant protein, DNA, and dbEST/dbSTS sequences (tags) database and the Derwent DNA and protein patent databases were searched for homology to the DNA sequence and the deduced amino acid sequence of clone Pgm613. Homology of DNA sequence and the deduced amino acid sequence was found between a portion of the Pgm613 clone (nucleotide positions 461–684, amino acid residues 153–228) and the F29 clone of Knapp et al. contained in European Patent Application 0431541A2. In addition, homology between the DNA sequence of Pgm613 and several *T. gondii* expressed sequence tags of unknown function isolated by Wan, K.-L. et al. (1996) Molec. And Biochem. Parasitol. 75, 179–186 was also found.

EXAMPLE 9

Isolation and Characterization of a Genomic Clone Containing the P29 Gene and Generation of a Composite DNA Sequence Since the Cdna insert of Pgm613 encoding the P29 antigen of Toxoplasma appeared to be less than full-length, a portion of the Pgm613 Cdna sequence was used as a probe to isolate a genomic clone of the P29 antigen with the goal of cloning the remaining 5' end of the gene.

Step A: Construction of a Toxoplasma Genomic DNA Library in Pjo200

A Toxoplasma genomic DNA library was constructed in the Pjo200 vector as follows. Toxoplasma genomic DNA prepared in Example 2A was treated by a partial digestion with the restriction enzyme Sau 3AI as described in General Methods. The partially digested genomic DNA was subsequently electrophoresed on a 0.7% agarose gel with molecular weight standards and the 6–15 Kb molecular weight range of the DNA was isolated, purified, and extracted as described in General Methods. In preparation for ligation with the genomic DNA, plasmid Pjo200 was digested with BamH-I followed by dephosphorylation with the CIAP enzyme. The resulting vector backbone was extracted and then ligated overnight at 16° C. with the Sau 3AI digested DNA. The ligation mixture was transformed the next day into competent XL-1 Blue cells, and the resulting transformants were pooled resulting in a primary Toxoplasma genomic library containing 80,000 members.

Step B: Screening Toxoplasma Genomic Library With P29 5' Gene Probe

In order to isolate the 5' end of the P29 gene from the genomic library, a portion of the 5' end of the Cdna clone present in Pgm613 was selected as a probe. This portion of the Cdna was then used to probe the Toxoplasma genomic library prepared in Example 9A for genomic clones homologous to the 5' end of the Cdna.

Plasmid Pgm613 was digested with SacII and HindIII, and the 326 bp SacII/HindIII fragment containing the 5' end of the Cdna insert in Pgm613 (nucleotide positions 55–380, see FIG. 1) was gel purified. This gene fragment was radioactively labelled and used to probe the Toxoplasma genomic library by colony hybridization as described in General Methods. Positive clones obtained by hybridization were colony purified and retested. One positive clone designated Ptxg1-2 containing a 6.5 Kb insert of DNA was further characterized as described below.

Step C: DNA Sequence of Genomic Clone Ptxg1-2 and Composite DNA Sequence for the P29 Gene and the Deduced Amino Acid Sequence The 5' end of the P29 gene contained in clone Ptxg1-2 was sequenced as described in General Methods using DNA primers complementary to the 5' end of the Cdna contained in clone Pgm613. The DNA sequence obtained for clone Ptxg1-2 [SEQ ID NO:25] is shown in FIG. 2. An alignment of the DNA sequences for genomic clone Ptxg-1 and the Cdna clone Pgm613 was then performed resulting in the composite DNA sequence [SEQ ID NO:26] and deduced amino acid sequence [SEQ ID NO:27] for the P29 gene as shown in FIGS. 3A, 3B, 3C and 3D. The composite DNA sequence is derived from the genomic sequence of clone Ptxg-1 (FIG. 2, [SEQ ID NO:25]) and the Cdna sequence of Pgm613 (FIGS. 1A, 1B and 1C, [SEQ ID NO:23]) as shown below in Table 3.

TABLE 3

| Source of Sequence for the Composite DNA Sequence for the P29 Gene | | |
|---|---|---|
| Nucleotide Position Composite Sequence | Nucleotide Position Genomic Sequence | Nucleotide Position Cdna Sequence |
| 1–419 | 1–419 | None |
| 420–477 | 420–477 | 40–97 |
| 478–1648 | None | 98–1268 |

The only good candidate for the initiator methionine residue for the start of translation of the P29 gene is the first methionine shown in FIG. 3 starting at nucleotide position 358. This is the only methionine in-frame with the reading frame present in the Cdna clone Pgm613. If the same reading frame is examined further upstream of the methionine at position 358, no further methionine residues are found before an in-frame UAA stop codon present at position 325. The methionine at nucleotide position 358 is surrounded by sequences fulfilling the criteria for initiation of translation (Kozak, M. (1986) Cell 44, 283–292) and is followed by amino acid residues that constitute a signal peptide (von Heijne, G. (1986) Nucleic Acids Res. 14, 4683–4690).

EXAMPLE 10

Construction of an Improved CKS Epitope-Embedding Vector Pee3

The CKS epitope-embedding expression vector Pee1 described in U.S. patent application Ser. No. 08/742,619 of Maine and Chovan allows for the embedded fusion of recombinant proteins to the CMP-KDO synthetase (CKS) protein. In order to facilitate the cloning of the P29 gene into the CKS epitope-embedding vector, the Pee1 vector was modified in two steps. First, an obsolete polylinker near the 3' end of the CKS gene in the Pee1 vector was removed generating an intermediate vector Pee2. Secondly, a new polylinker was introduced into the coding region of CKS, thus permitting the embedding of genes using a variety of restriction sites (StuI, EcoRI, SacI, BamH-I, PstI, MluI) into the CKS gene.

Step A: Construction of Pee2

The plasmid Pee2, a derivative of the CKS expression vector Pee1 (FIG. 4A), was constructed by digesting Pee1 with the Bgl II restriction enzyme and removing a polylinker located at the 3' end of the CKS gene which had the sequence (5'–3') [SEQ ID NO:28] (FIG. 4B) and the deduced amino acid sequence [SEQ ID NO:49]

AGATCTCGACCCGTCGACGAATTC-
GAGCTCGGTACCCCGGGATCCTCTAGAC

AspLeuAspProSerThrAsnSerSerSerValProGlyAspProLeuAsp

TGCAGGCATGCTAAGTAAGTAGATCT

CysArgHisAlaLys and replacing it with the following sequence (5'–3') [SEQ ID NO:29] (see FIG. 4C) and the deduced amino acid sequence [SEQ ID NO:50]

AGATCTCGACCCATCTACCAATTCGTCT-
TCTGTTCCGGGTGATCCGCTAGAC

AspLeuAspProSerThrAsnSerSerSerValProGlyAspProLeuAsp

TGCCGTCACGCTAAGTAAGTAGATCT

CysArgHisAlaLys

As shown in FIGS. 4B and 4C, this sequence replacement removes the restriction sites SalI, EcoRI, SacI, KpnI, SmaI, BamH-I, XbaI, PstI, and SphI, thus enabling the use of these sites in a new polylinker to be embedded later within the CKS gene further upstream (Example 10B).

Plasmid Pee1 was digested with Bgl II and then treated with the CIAP enzyme to remove the five prime phosphate groups to prevent self-ligation. The Pee1/Bgl II dephosphorylated vector backbone was then purified on an agarose gel. Two oligonucleotides shown below (5'–3') were synthesized for ligation into the Pee1/Bgl II backbone.

SEQ ID NO:30

CCTGAAGATCTCGACCCATCTACCAAT-
TCGTCTTCTGTTCCGGGTGATCC GCTAGACTGCCGT-
CACGCTAAGTAAGTAGATCTTGACT

SEQ ID NO:31

AGTCAAGATCTACTTACTTAGCGTGACG-
GCAGTCTAGCGGATCACCCGGA ACAGAAGACGAATTG-
GTAGATGGGTCGAGATCTTCAGG

These oligonucleotides were mixed together, heated to 85° C. and then allowed to cool gradually overnight to 4° C. to permit annealing of the oligonucleotides. The annealed oligonucleotides were then digested with the Bgl II enzyme, extracted, and then ligated to the Pee1/Bgl II backbone overnight at 16° C. The ligation mixture was transformed the next day into competent XL-1 Blue cells. Miniprep DNA was prepared from the transformants and screened for the presence of the new sequence by restriction enzyme analysis. Putative correct clones were then sequenced to verify the correct sequence in the proper orientation. Plasmid Pee2 was isolated which contains the new sequence [SEQ ID NO:29] at the Bgl II site.

Step B: Construction of Pee3

The plasmid Pee3, a derivative of the CKS expression vector Pee2 (FIG. 5A), was constructed by digesting Pee2 with StuI and MluI and cloning in a new polylinker with the following sequence (5'–3') [SEQ ID NO:32] (see FIG. 5B) and deduced amino acid sequence SEQ ID NO:51.

AGGCCTGAATTCGAGCTCTGGGATCCGTCTGCAGACGCGT

GlyLeuAsnSerSerSerGlyIleArgLeuGlnThrArg which contains the restriction sites StuI, EcoRI, SacI, BamH-I, PstI, and MluI.

Plasmid Pee2 was digested with StuI and MluI, and the vector backbone was purified on an agarose gel. Two oligonucleotides shown below (5'–3') were synthesized for ligation into the Pee2/StuI/MluI backbone.

SEQ ID NO:33

CCTGAATTCGAGCTCTGGGATCCGTCTGCAGA

SEQ ID NO:34

CGCGTCTGCAGACGGATCCCAGAGCTCGAATTCAGG

These oligonucleotides were mixed together, heated to 80° C. for 10 minutes and then allowed to cool gradually overnight to 4° C. to permit annealing of the oligonucleotides. The annealed oligonucleotides were then ligated to the Pee2/StuI/MluI backbone overnight at 16° C. The ligation mixture was transformed the next day into competent XL-1 Blue cells. Miniprep DNA was prepared from the transformants and screened for the presence of the new sequence by restriction enzyme analysis. Putative correct clones were then sequenced to verify the correct sequence. Plasmid Pee3 was isolated which contains the new sequence [SEQ ID NO:32] at the StuI/MluI sites.

EXAMPLE 11

Construction of CKS-Toxo Ag-CKS Epitope-Embedding Expression Vectors

The CKS expression vectors Pjo200, Pee1, and Pee3 were utilized for the construction of four CKS-Toxo Ag-CKS gene fusion constructs using the Toxo P29, P30, P35, and P66 genes.

Step A: Construction of pToxo-P29: CKS-P29(1-236aa)-CKS

Figure 6:
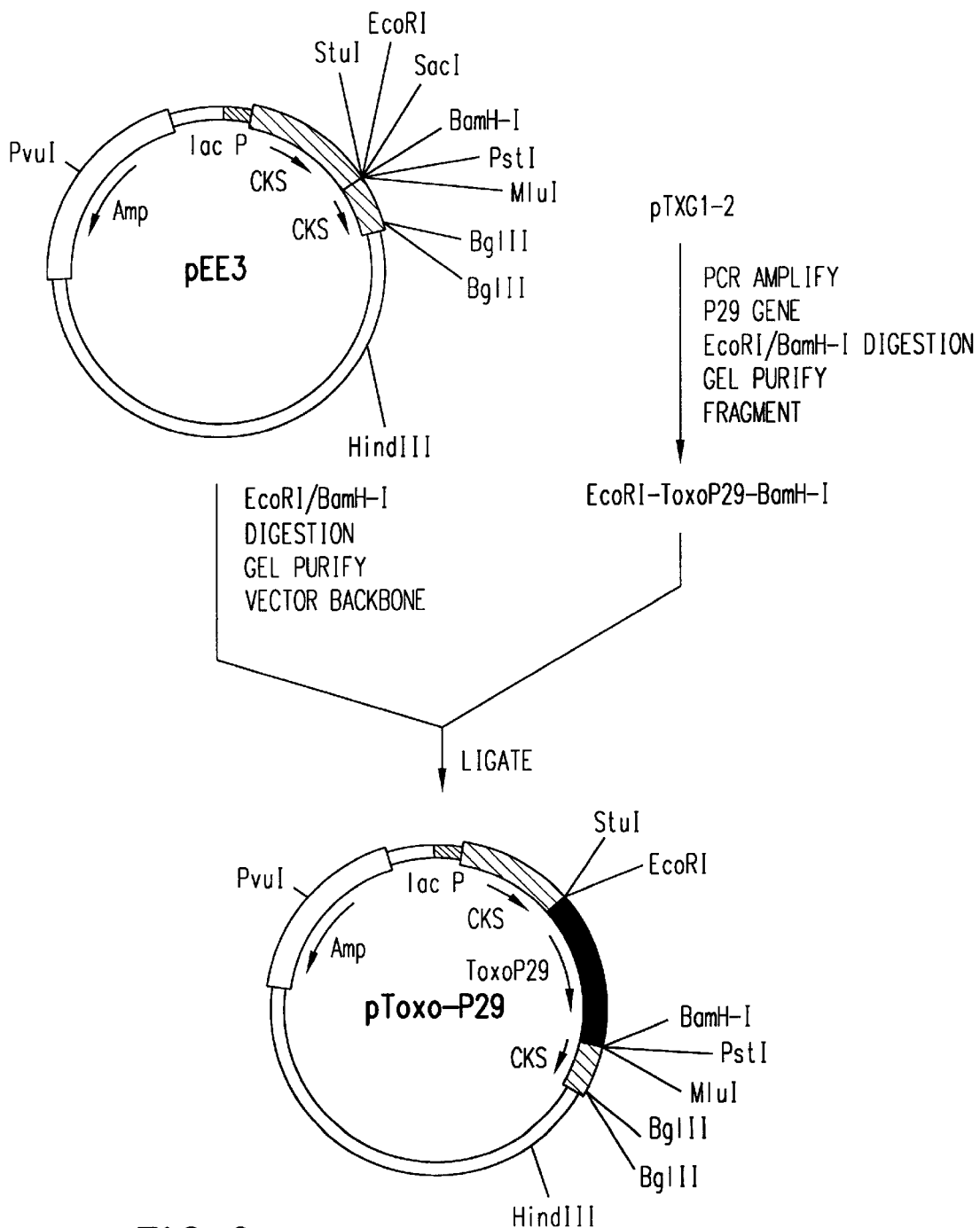
FIG. 6 is a schematic representation of the construction of plasmid pToxo-P29.

The plasmid pToxo-P29, a derivative of plasmid Pee3 (FIG. 6), was constructed by cloning a DNA fragment containing Toxo P29, obtained by PCR amplification of Toxo P29 DNA contained in plasmid Ptxg1-2 (Example 9C), into the EcoRI/BamH-I sites of Pee3. Plasmid pToxo-P29 was deposited with the ATCC, 10801 University Boulevard, Manassas, Va. 20110-2209, under terms of the Budapest Treaty on May 19, 1998, and was accorded Accession No. ATCC 98758.

Large scale plasmid DNAs (Ptxg1-2 and Pee3) were isolated by general methods. Plasmid Pee3 was digested with EcoRI and BamH-I, and the vector backbone, Pee3/EcoRI/BamH-I, was purified on an agarose gel. A sense primer, starting at nucleotide 358 of the P29 gene (FIGS. 3A, 3B, 3C, and 3D) containing an EcoRI site, and an antisense primer containing a BamH-I site, starting at nucleotide 1065 of the P29 gene, were synthesized as shown below:

Sense Primer [SEQ ID NO:35]

5'-ACTTA<u>GAATTC</u>GATGGCCCGACACGCAATTTTTTCC-3'

(EcoRI site is underlined)

Antisense Primer [SEQ ID NO:36]

5'-ACAT<u>GGATCC</u>GCTGGCGGGCATCCTCCCCATCTTC-3'

(BamH-I site is underlined)

The sense and antisense primers were added to a PCR reaction mixture containing plasmid Ptxg1-2. After PCR amplification, the reaction mixture was digested with EcoRI and BamH-I, and the 708 base pair DNA fragment containing P29 was purified on an agarose gel. The purified 708 base pair DNA fragment was ligated to Pee3/EcoRI/BamH-I overnight at 16° C. The ligation mixture was transformed the next day into competent XL-1 Blue cells. Miniprep DNA was prepared from the transformants and screened for the presence of the P29 DNA sequence by restriction enzyme analysis. Plasmid pToxo-P29 contained the P29 gene embedded at the EcoRI/BamH-I sites of Pee3. This CKS-ToxoP29-CKS fusion construct was designated:

"CKS(1-171aa)-N-S-ToxoP29(1-236aa)-R-I-R-L-Q-T-R-CKS (171-260aa)"

where N, S, R, I, R, L, Q, T, R are the asparagine, serine, arginine, isoleucine, arginine, leucine, glutamine, threonine, and arginine residues, respectively, encoded by the polylinker DNA sequence of the vector. The complete DNA sequence [SEQ ID NO:37] of plasmid pToxo-P29 and the corresponding amino acid sequence [SEQ ID NO:52] of the CKS-P29-CKS fusion protein are shown are FIGS. 7A through 7J.

Step B: Construction of pToxo-P30:CKS-P30(1-236aa)-CKS

Figure 8:
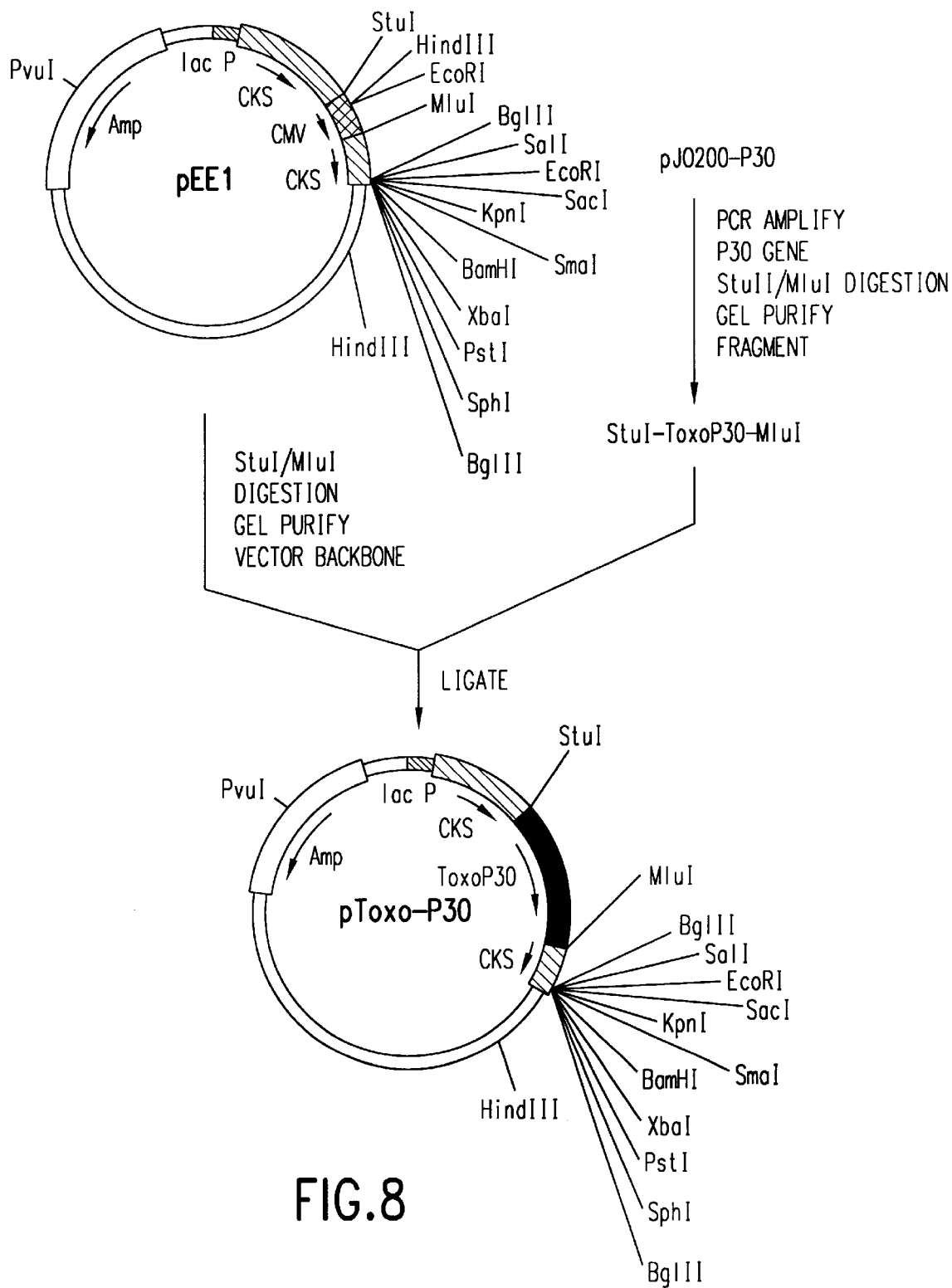
FIG. 8 is a schematic representation of the construction of plasmid pToxo-P30.

The plasmid pToxo-P30, a derivative of plasmid Pee1 (FIG. 8), was constructed by cloning a DNA fragment containing Toxo P30, obtained by PCR amplification of Toxo P30 DNA contained in plasmid Pjo200-P30 (Example 3A), into the StuI/MluI sites of Pee1. Plasmid pToxo-P30 was deposited with the ATCC, 10801 University Boulevard, Manassas, Va. 20110-2209, under the terms of the Budapest Treaty on May 19, 1998, and was accorded Acession No. ATCC 98761.

Large scale plasmid DNAs (Pjo200-P30 and Pee1) were isolated by general methods. Plasmid Pee1 was digested with StuI and MluI, and the vector backbone, Pee1/StuI/MluI, was purifed on an agarose gel. A sense primer, starting at nucleotide 464 of the P30 gene containing an StuI site, and an antisense primer containing a MluI site, starting at nucleotide 1318 of the P30 gene (Burg et al. (1988) J. Immunol. 141, 3584–3591) were synthesized as shown below:

Sense Primer [SEQ ID NO:38]

5'-TCCT<u>AGGCCT</u>TAATTCGATGCTTGTTGCCAATCAAG-3'

(StuI site is underlined)
Antisense Primer [SEQ ID NO:39]

5'-ACAT<u>ACGCGT</u>CGCGACACAAGCTGCGATAGAG-3'

(MluI site is underlined)

The sense and antisense primers were added to a PCR reaction mixture containing plasmid Pjo200-P30. After PCR amplification, the reaction mixture was digested with StuI and MluI, and the 855 base pair DNA fragment containing P30 was purified on an agarose gel. The purified 855 base pair DNA fragment was ligated to Pee1/StuI/MluI overnight at 16° C. The ligation mixture was transformed the next day into competent XL-1 Blue cells. Miniprep DNA was prepared from the transformants and screened for the presence of the P30 DNA sequence by restriction enzyme analysis. Plasmid pToxo-P30 contained the P30 gene embedded at the StuI/MluI sites of Pee1. This CKS-ToxoP30-CKS fusion construct was designated:

"CKS(1-171aa)-N-S-M-ToxoP30(5-289aa)-T-R-CKS (171-260aa)"

where N, S, M, T, R are the asparagine, serine, methionine, threonine, and arginine residues, respectively, encoded by the synthetic DNA sequence of the vector. The complete DNA sequence [SEQ ID NO:40] of plasmid pToxo-P30 is shown in FIGS. 9A through 9I and the corresponding amino acid sequence [SEQ ID NO:53] of the CKS-P30-CKS fusion protein are shown in FIGS. 9A through 9I.

Step C: Construction of pToxo-P35S:CKS-P35(1-135aa)-CKS

Figure 10:
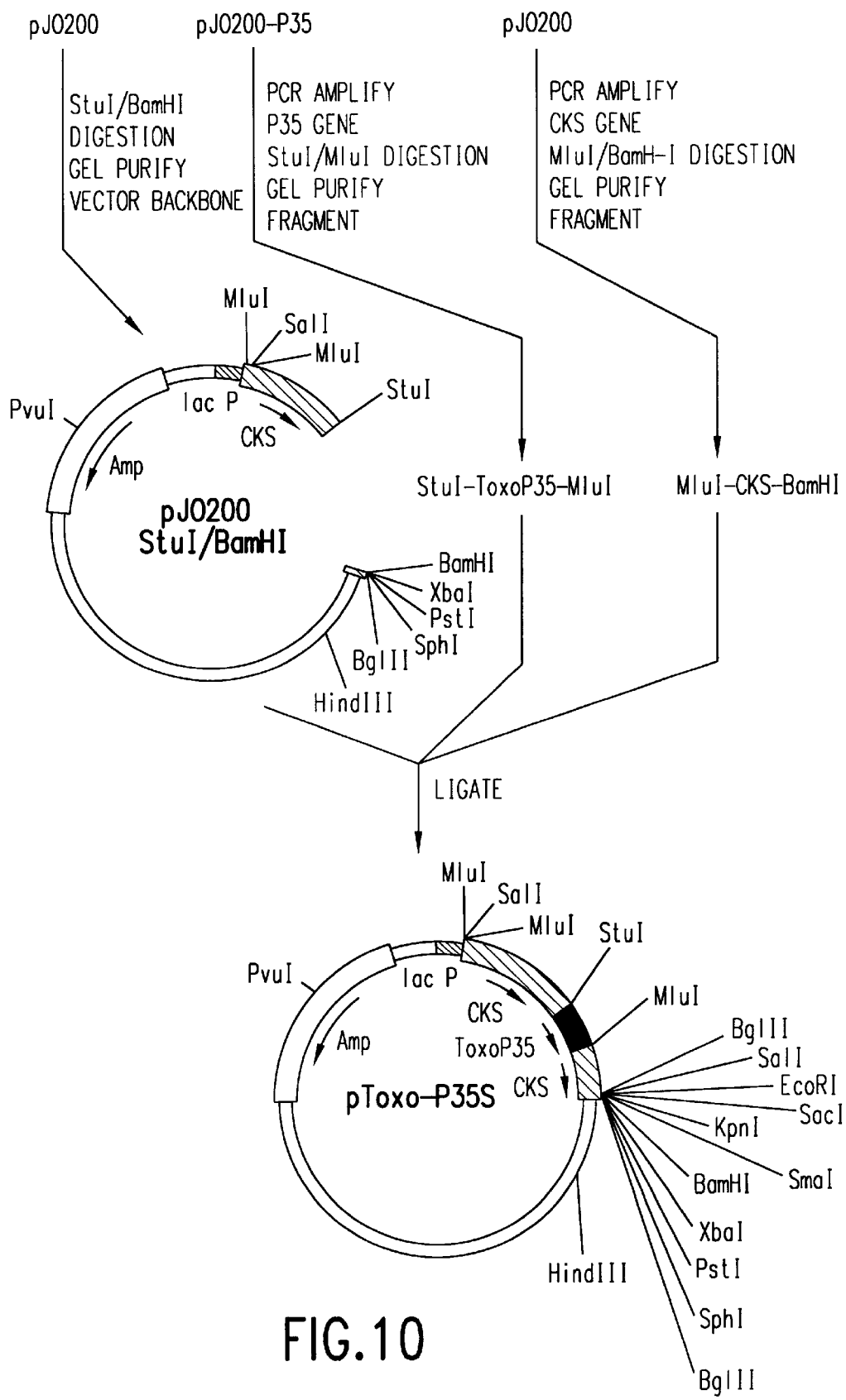
FIG. 10 is a schematic representation of the construction of plasmid pToxo-P35S.

The plasmid pToxo-P35S, a derivative of plasmid Pjo200 (FIG. 10), was constructed by cloning a DNA fragment containing Toxo P35, obtained by PCR amplification of Toxo P35 DNA contained in plasmid Pjo200-P35 (Example 3A), into the StuI site of Pjo200. Plasmid pToxo-P35S was deposited with the ATCC, 10801 University Boulevard, Manassas, Va. 20110-2209, under terms of the Budapest Treaty on May 19, 1998, and was accorded Accession No. ATCC 98759.

Large scale plasmid DNAs (Pjo200-P35 and Pjo200) were isolated by general methods. Plasmid Pjo200 was digested with StuI and BamH-I, and the vector backbone, Pjo200/StuI/BamH-I, was purified on an agarose gel. A sense primer, starting at nucleotide 91 of the P35 gene containing an StuI site, and an antisense primer containing a MluI site, starting at nucleotide 495 of the P35 gene (Knapp et al., 1989 (EPA 431541A2)) were synthesized as shown below:

Sense Primer [SEQ ID NO:41]

5'-GAGCAGA<u>AGGCCT</u>TATGAACGGTCCTTTGAGTTATCATCC-3'

(StuI site is underlined)
Antisense Primer [SEQ ID NO:42]

5'-TTCGCTC<u>ACGCGT</u>ATGGTGAACTGCCGGTATCT-3'

(MluI site is underlined)

The sense and antisense primers were added to a PCR reaction mixture containing plasmid Pjo200-P35. After PCR amplification, the reaction mixture was digested with StuI and MluI, and the 405 base pair DNA fragment containing P35 was purified on an agarose gel. A sense primer, starting at nucleotide 640 of Pjo200 containing an MluI site, and an antisense primer starting at nucleotide 905 of Pjo200 were synthesized as shown below:

Sense Primer [SEQ ID NO:43]

5'-GACGGAG<u>ACGCGT</u>CTTGAACCGTTGGCGATAACT-3'

(MluI site is underlined)
Antisense Primer [SEQ ID NO:44]

5'-GCATGCCTGCAGTCTAGAGGA-3'

The sense and antisense primers were added to a PCR reaction mixture containing plasmid Pjo200. After PCR amplification, the reaction mixture was digested with MluI and BamH-I, and the 266 base pair DNA fragment containing P35 was purified on an agarose gel.

The purified 405 base pair DNA fragment containing the P35 gene and the purified 266 base pair DNA fragment containing the 3' end of the CKS gene, were ligated to Pjo200/StuI/BamH-I overnight at 16° C. The ligation mixture was transformed the next day into competent XL-1 Blue cells. Miniprep DNA was prepared from the transformants and screened for the presence of the P35 DNA sequence by restriction enzyme analysis. Plasmid pToxo-P35S contained the P35 gene embedded at the StuI/MluI sites of Pjo200. This CKS-ToxoP35-CKS fusion construct was designated:

"CKS(1-171aa)-ToxoP35(1-135aa)-T-R-CKS(171-260aa)"

where T and R are the threonine and arginine residues, respectively, encoded by the synthetic DNA sequence of the vector. The complete DNA sequence [SEQ ID NO:45] of plasmid pToxo-P35S and the corresponding amino acid sequence [SEQ ID NO:54] of the CKS-P35-CKS fusion protein are shown in FIGS. 11A through 11I.

Step D: Construction of pToxo-P66q: CKS-P66(26-428aa)-CKS

Figure 12:
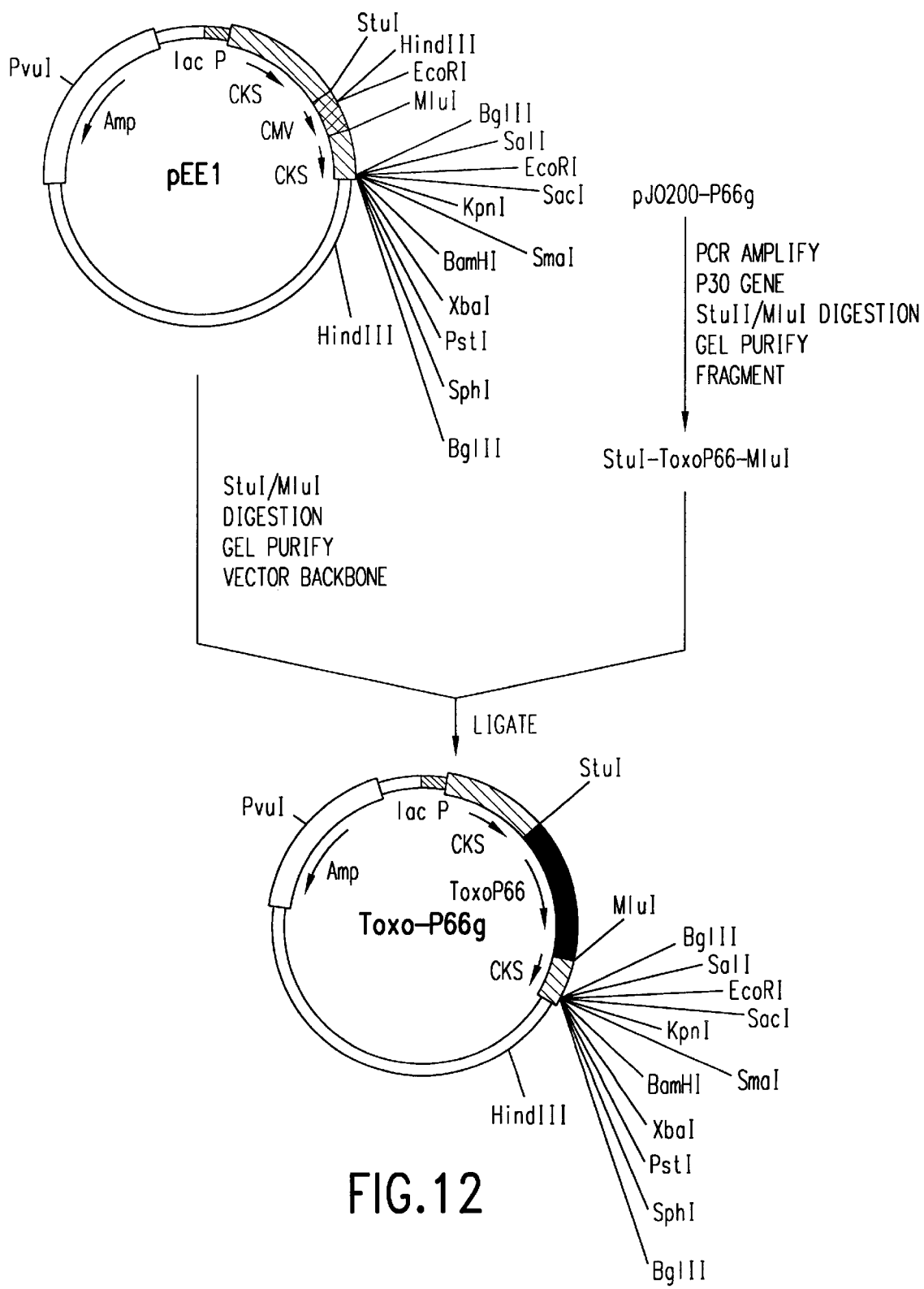
FIG. 12 is a schematic representation of the construction of plasmid pToxo-P66g.
Figure 14:
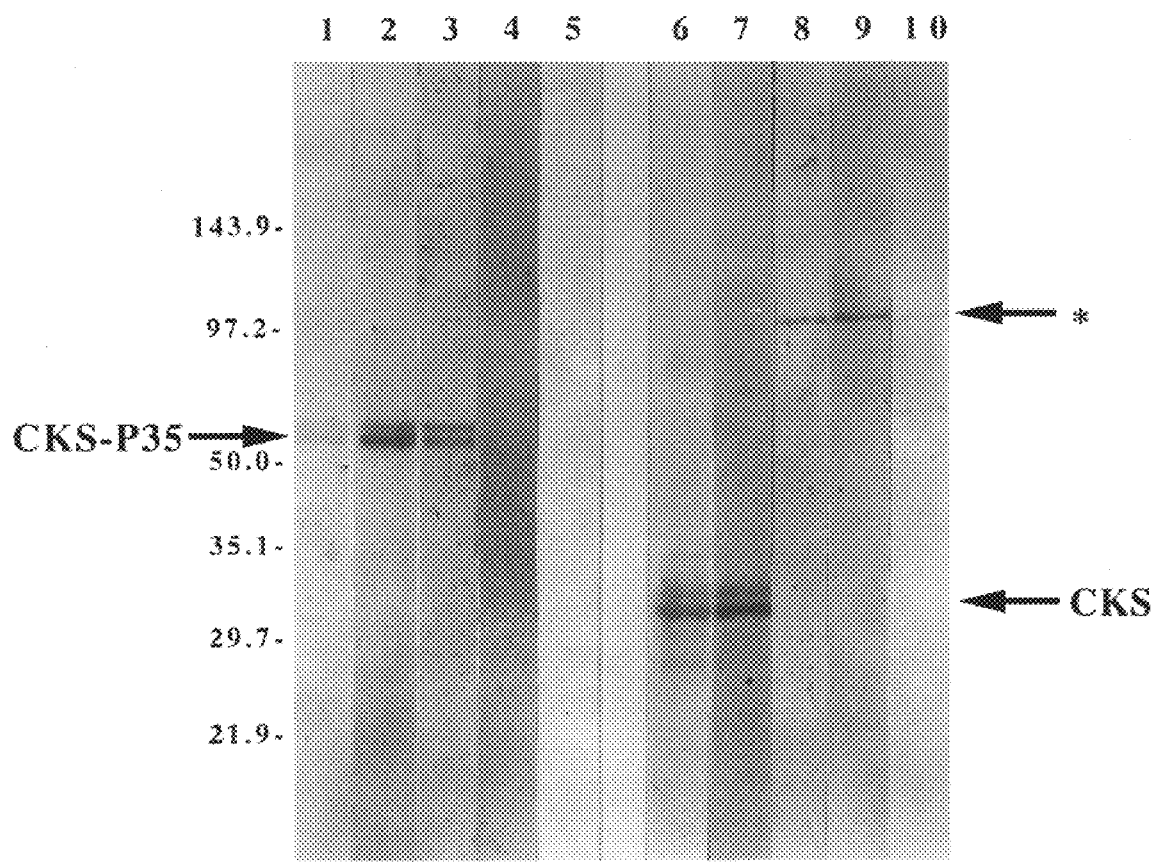
FIG. 14 illustrates the reactivity of *T. gondii* antibodies with rpToxo-P35S and with CKS preparations. Strips of the rpToxo-P35S blot (A) or CKS blot (B) were stained with amido black (lane 1), monoclonal antibody against CKS protein (lane 2), pooled Group I sera (lane 3), pooled Group II sera (lane 4) or pooled Group III sera (lane 5). The position of rpToxo-P35S (approximately 54 kD) and the CKS protein (approximately 34 kD) are indicated with arrows. Molecular weight markers are indicated on the side. Cross-reactive bands in the CKS preparation are also indicated by arrows.

The plasmid pToxo-66g, a derivative of plasmid Pee1 (FIG. 12), was constructed by cloning a DNA fragment containing Toxo P66, obtained by PCR amplification of Toxo P66 DNA contained in plasmid Pjo200-P66g (Example 3A), into the StuI/MluI sites of Pee1. Plasmid pToxo-P66g was deposited with the ATCC, 10801 University Boulevard, Manassas, Va. 20110-2209, under terms of the Budapest Treaty on May 19, 1998, and was accorded Accession No. ATCC 98760.

Large scale plasmid DNAs (Pjo200-P66g and Pee1) were isolated by general methods. Plasmid Pee1 was digested with StuI and MluI, and the vector backbone, Pee1/StuI/MluI, was purified on an agarose gel. A sense primer, starting at nucleotide 122 of the P30 gene containing an StuI site, and an antisense primer containing a MluI site, starting at nucleotide 1330 of the P66 gene (Knapp et al., supra (1989)) were synthesized as shown below:

Sense Primer [SEQ ID NO:46]

5'-ATATT
AGGCCTTATGAGCCACAATGGAGTCCCCGCTTATCC-3'

(StuI site is underlined)
Antisense Primer [SEQ ID NO:47]

5'-CAGTGTACGCGTTTGCGATCCATCATCCTGCTCTCTTC-3'

(MluI site is underlined)

The sense and antisense primers were added to a PCR reaction mixture containing plasmid Pjo200-P66g. After PCR amplification, the reaction mixture was digested with StuI and MluI, and the 1209 base pair DNA fragment containing P66 was purified on an agarose gel. The purified 1209 base pair DNA fragment was ligated to Pee1/StuI/MluI overnight at 16° C. The ligation mixture was transformed the next day into competent XL-1 Blue cells. Miniprep DNA was prepared from the transformants and screened for the presence of the P66 DNA sequence by restriction enzyme analysis. Plasmid pToxo-P66g contained the P66 gene embedded at the StuI/MluI sites of Pee1. This CKS-ToxoP66-CKS fusion construct was designated:

"CKS(1-171aa)-M-ToxoP66(26-428aa)-T-R-CKS(171-260aa)"

where M, T, and R are the methionine, threonine and arginine residues, respectively, encoded by the synthetic DNA sequence of the vector. The complete DNA sequence [SEQ ID NO:48] of plasmid pToxo-P66g and the corresponding amino acid sequence [SEQ ID NO:55] of the CKS-P66-CKS are shown in FIGS. 13A through 13K.

EXAMPLE 12

Development of a Toxo Recombinant Antigen Cocktail for the Detection of Toxoplasma-Specific IgG and IgM The results in Tables 1 and 2 of Example 6B indicated that more than one recombinant antigen would be required to detect Toxoplasma-specific IgG and IgM in order to replace the tachyzoite in an immunoassay. Additional sera were sourced from patients with an acute or chronic Toxolasmosis and tested with the individual antigens coated in separate wells listed in Tables 1 and 2 using the IgG or IgM Microtiter ELISA described in Example 6B. These results indicated that a cocktail of recombinant antigens necessary and sufficient to replace the tachyzoite in an immunoassay should be composed of the following Toxo antigens:

Toxo IgG Immunoassay: P29+P30+P35

Toxo IgM Immunoassay: P29+P35+P66

In order to demonstrate the diagnostic utility of the Toxo recombinant antigens in the proposed above combinations in an immunoassay, i.e. the coating of the Toxo antigens P29, P30, and P35 in a single microtiter plate well (Microtiter format) or other solid phase, e.g. microparticles (MEIA format), to detect Toxoplasma-specific IgG antibodies and the coating of the Toxo antigens P29, P35, and P66 in a single microtiter plate well (Microtiter format) or other solid phase, e.g. microparticles (MEIA format), to detect Toxoplasma-specific IgM antibodies, the following experiments were performed:

Step A: Expression of cloned genes in *E. coli*

Bacterial clones pToxo-P29, pToxo-P30, pToxo-P35S, and pToxo-P66g expressing the CKS fusion proteins rpToxo-P29, rpToxo-P30, rpToxo-P35S, and rpToxo-P66g, respectively, were grown in SUPERBROTH II media containing 100 ug/ml ampicillin to log phase, and the synthesis of the CKS-Toxo fusion protein was induced by the addition of IPTG as previously described (Robinson et al. (1993) J. Clin. Micro. 31, 629–635). After 4 hours post-induction, the cells were harvested, and the cell pellets were stored at -80° C. until protein purification.

Step B: Purification of Recombinant Toxo Antigens

Insoluble recombinant antigens rpToxo-P29, rpToxo-P30, rpToxo-P35S, and rpToxo-P66g were purified after lysis from cell paste by a combination of detergent washes followed by solubilization in 8M urea (Robinson et al., supra (1993)). After solubilization was complete, these proteins were filtered through a 0.2 m filter and either stored at 2–8° C. (w/urea) or dialyzed against 50 Mm Tris, Ph 8.5 and then stored at 2–8° C. (w/o urea)

Step C: Human Sera for Testing

Four groups of serum specimens from a French population were evaluated for the presence of Toxoplasma-specific IgG and IgM antibodies using the Microtiter ELISA. These serum specimens collectively cover the entire span of Toxoplasma infection from early seroconversion (acute toxoplasmosis) to convalesence (latent infection, chronic toxoplasmosis) and represent the types of specimens normally encountered in routine Toxoplasma serology.

Group 1: Negative Serum Specimens

This group contained 200 serum specimens negative for Toxoplasma IgG and IgM antibodies as determined by the Abbott Imx Toxo IgG and IgM immunoassays.

Group 2: "Ancienne" Serum Specimens

This group contained 100 serum specimens negative for Toxoplasma IgM antibodies and positive for Toxoplasma IgG antibodies by the Abbott Imx Toxo IgG and IgM immunoassays. These specimens were negative for Toxoplasma IgA antibodies as determined by an immunocapture assay using a suspension of tachyzoites (IC-A) (Pinon, J. M. (1986) Diag. Immunol. 4:223–227).

Group 3: "Évolutive" Serum Specimens

This group contained 99 serum specimens positive for Toxoplasma IgG antibodies by a high sensitivity direct agglutination assay (HSDA) (Desmonts, G. and Remington, J. S. (1980) J. Clin. Micro. 11:562–568) and positive for Toxoplasma IgM and IgA antibodies using a specific immunocapture assay (IC-M, IC-A).

Group 4: "Précoce" Serum Specimens This group contained 66 specimens sourced from individuals with evidence of a early seroconversion of Toxoplasma-specific antibodies (absence or early manifestation of IgG antibodies and positive for IgM and IgA antibodies using a specific immunocapture assay (IC-M, IC-A)).

Step D: Evaluation of Human Sera in the Recombinant Toxo Antigen Microtiter ELISA Purified recombinant Toxo antigens (Example 12B) were coated onto the wells of the microtiter plate as follows:

For the IgG microtiter ELISA, the three Toxo antigens rpToxo-P29, rpToxo-P30, and rpToxo-P35S (w or w/o urea) were diluted together into PBS to a final concentration of 5 ug/ml for each antigen, and plates were coated and processed as described in Example 6B using a goat anti-human IgG-HRPO conjugate to detect bound human IgG. All three Toxo antigens were coated together into the same microtiter well to detect Toxoplasma-specific IgG. For the IgM microtiter ELISA, the three Toxo antigens rpToxo-P29, rpToxo-P35S, and rpToxo-P66g (w or w/o urea) were diluted together into PBS to a final concentration of 5 mg/ml for each antigen, and plates were coated and processed as described in Example 6B using a goat anti-human IgM-HRPO conjugate to detect bound human IgM. All three Toxo antigens were coated together into the same microtiter well to detect Toxoplasma-specific IgM. The cut-off for these assays was between 2 to 3 standard deviations from the mean of the negative population.

Step E: Results of the Evaluation of Human Sera in the Recombinant Toxo Antigen (P29+P30+P35) IgG Microtiter ELISA The serum specimens from Groups 1–4 (Example 12C) were tested for the presence of Toxoplasma-specific IgG using the recombinant Toxo antigen IgG microtiter ELISA (rpToxo-P29 (P29)+rpToxo-P30 (P30)+rpToxo-P35S (P35)). The results from this evaluation are presented in Tables 4–8.

TABLE 4

Evaluation of Group 1 Negative Serum Specimens by Toxo IgG Microtiter ELISA

| | Abbott Imx Toxo IgG | |
|---|---|---|
| | Pos | Neg |
| Toxo IgG (P29 + P30 + P35) Microtiter ELISA Pos | 0 | 8 |
| Toxo IgG (P29 + P30 + P35) Microtiter ELISA Neg | 0 | 192 |
| Specificity: | 192/200 = 96% | |

TABLE 5

Evaluation of Group 2 "Ancienne" Serum Specimens by Toxo IgG Microtiter ELISA

| | Abbott Imx Toxo IgG | |
|---|---|---|
| | Pos | Neg |
| Toxo IgG (P29 + P30 + P35) Microtiter ELISA Pos | 97 | 0 |
| Toxo IgG (P29 + P30 + P35) Microtiter ELISA Neg | 3 | 0 |
| Sensitivity: | 97/100 = 97% | |

TABLE 6

Evaluation of Group 3 "Évolutive" Serum Specimens by Toxo IgG Microtiter ELISA

| | HSDA IgG | |
|---|---|---|
| | Pos | Neg |
| Toxo IgG (P29 + P30 + P35) Microtiter ELISA Pos | 99 | 0 |
| Toxo IgG (P29 + P30 + P35) Microtiter ELISA Neg | 0 | 0 |
| Sensitivity: | 99/99 = 100% | |

TABLE 7

Evaluation of Group 4 "Précoce" Serum Specimens by Toxo IgG Microtiter ELISA

| | HSDA IgG | |
|---|---|---|
| | Pos | Neg |
| Toxo IgG (P29 + P30 + P35) Microtiter ELISA Pos | 54 | 1 |
| Toxo IgG (P29 + P30 + P35) Microtiter ELISA Neg | 1 | 10 |
| Sensitivity: | 54/55 = 98.1% | |

TABLE 8

Summary of Evaluation of Groups 1–4 Serum Specimens by Toxo IgG Microtiter ELISA

|  |  | Reference Test | |
|---|---|---|---|
|  |  | Pos | Neg |
| Toxo IgG (P29 + P30 + P35) Microtiter ELISA | Pos | 250 | 9 |
|  | Neg | 4 | 202 |
| Specificity: | 202/211 = 95.7% | | |
| Sensitivity: | 250/254 = 98.4% | | |

As can be seen from Tables 4–8, the Toxo IgG microtiter ELISA is both a sensitive and specific assay for the detection of Toxoplasma-specific IgG as demonstrated by the overall high relative diagnostic specificity (95.7%) and sensitivity (98.4%) (Table 8) of the assay. The Toxo recombinant antigen cocktail comprised of the Toxo antigens P29, P30 and P35, in combination with the Toxo IgG assay, is both necessary and sufficient to replace the tachyzoite for the detection of Toxoplasma-specific IgG antibody.

Furthermore, there are several advantages of the recombinant antigen cocktail over the tachyzoite antigen for use in detection of IgG antibodies. First, the antigens are purified, and the amount of each antigen loaded into the immunoassay can be accurately determined and standardized, e.g., protein concentration. This minimizes interlot differences commonly observed in kits manufactured with different tachyzoite antigen lots. Hence, different lots of kits manufactured with different antigen cocktail lots will be very consistent from lot to lot. Secondly, mouse monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Finally, kits manufactured with the antigen cocktail are more stable during storage over time, and the performance of the assay using these antigens remains consistent over the shelf life of the assay. Kits manufactured with the tachyzoite antigen are not as stable and their performance may vary over time.

Additionally, there are many advantages of using a cocktail over using a single antigen alone. For example, an immune response to infection varies by individual. Some individuals produce antibodies to P35 and not to P66, whereas some individuals produce antibodies to P66 and not to P35. Thus, the antigen cocktail of the present invention will detect both groups of individuals.

Moreover, immune responses vary with time. For example. One individual may produce antibodies against P35 first and then later produce antibodies to only P66. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is known from previous Western Blot experiments with tachyzoite proteins that the immune response to Toxoplasma is directed against several antigens. Once again, the present antigen cocktail will allow for the detection of all antibodies produced in response to these antigens.

Step F: Results of the Evaluation of Human Sera in the Recombinant Toxo Antigen (P29+P35+P66) IgM Microtiter ELISA The serum specimens from Groups 1–4 (Example 12C) were tested for the presence of Toxoplasma-specific IgM using the recombinant Toxo antigen IgM microtiter ELISA (rpToxo-P29 (P29)+rpToxo-P35S (P35)+rpToxo-P66g (P66)). The results from this evaluation are presented in Tables 9–13.

TABLE 9

Evaluation of Group 1 Negative Serum Specimens by Toxo IgM Microtiter ELISA

|  |  | Abbott Imx Toxo IgM | |
|---|---|---|---|
|  |  | Pos | Neg |
| Toxo IgM (P29 + P35 + P66) Microtiter ELISA | Pos | 0 | 7 |
|  | Neg | 0 | 193 |
| Specificity: | 193/200 = 96.5% | | |

TABLE 10

Evaluation of Group 2 "Ancienne" Serum Specimens by Toxo IgM Microtiter ELISA

|  |  | Abbott Imx Toxo IgM | |
|---|---|---|---|
|  |  | Pos | Neg |
| Toxo IgM (P29 + P35 + P66) Microtiter ELISA | Pos | 0 | 8 |
|  | Neg | 0 | 92 |
| Specificity: | 92/100 = 92.0% | | |

TABLE 11

Evaluation of Group 3 "Évolutive" Serum Specimens by Toxo IgM Microtiter ELISA

|  |  | IC IgM | |
|---|---|---|---|
|  |  | Pos | Neg |
| Toxo IgM (P29 + P35 + P66) Microtiter ELISA | Pos | 69 | 0 |
|  | Neg | 30 | 0 |
| Sensitivity: | 69/99 = 70.0% | | |

TABLE 12

Evaluation of Group 4 "Précoce" Serum Specimens by Toxo IgM Microtiter ELISA

|  |  | IC IgM | |
|---|---|---|---|
|  |  | Pos | Neg |
| Toxo IgM (P29 + P35 + P66) Microtiter ELISA | Pos | 53 | 1 |
|  | Neg | 2 | 10 |
| Sensitivity: | 53/55 = 96.7% | | |

TABLE 13

Summary of Evaluation of Groups 1–4 Serum Specimens
by Toxo IgM Microtiter ELISA

|  |  | Reference Test | |
|---|---|---|---|
|  |  | Pos | Neg |
| Toxo IgM (P29 + P30 + P35) Microtiter ELISA | Pos | 122 | 16 |
|  | Neg | 32 | 295 |
| Specificity: | 295/311 = 94.9% | | |
| Sensitivity: | 122/154 = 79.2% | | |

As can be seen from Tables 9–13, the Toxo IgM microtiter ELISA is a specific assay for the detection of Toxoplasma-specific IgM as demonstrated by the overall high relative diagnostic specificity (94.9.%) (Table 13) of the assay. However, the assay appeared to be relatively insensitive to detection of Toxoplasma-specific IgM present in serum specimens from Group 3 "évolutive" (relative diagnostic sensitivity=70%, Table 11) but sensitive to detection of Toxoplasma-specific IgM present in serum specimens from Group 4 "précoce" (relative diagnostic sensitivity=96.7%, Table 12). These data suggest that the Toxo IgM microtiter ELISA may be more sensitive to the detection of Toxoplasma-specific IgM indicative of an acute or recent infection than the IC-M immunocapture assay used as the reference assay.

Further resolution testing was performed with the Abbott Imx Toxo IgM assay and a Toxo IgG avidity assay on the 30 discordant specimens listed in Table 11 that were positive for IgM antibody using the IC-M immunocapture assay and negative for IgM antibody by the Toxo IgM microtiter ELISA. Of the 30 specimens that were false negative by the Toxo IgM microtiter assay, 11 were resolved true negative by the Abbott Imx Toxo IgM assay. Furthermore, all 11 specimens contained Toxoplasma IgG with elevated avidity, representative of a past infection. Of the remaining 19 specimens that were false negative by the Toxo IgM microtiter assay, an additional 11 specimens corresponded to Toxoplasma infections which probably occurred greater than 6 months ago, as demonstrated by the presence of Toxoplasma-specific IgG high avidity antibodies. In addition, one specimen was from a patient with reactivation of toxoplasmosis where normally Toxo IgM antibodies are absent (an IC-M and Abbott Imx Toxo IgM false positive), and one specimen was from a patient with congenital toxoplasmosis. Therefore, after resolution by the Abbott Imx Toxo IgM assay followed by consideration of the Toxo IgG avidity data and clinical history of the specimens, of the 32 specimens false negative by the microtiter IgM assay, 11 were resolved true negative, 13 specimens (from congenitally infected patients) were removed from the calculation of relative diagnostic specificity and sensitivity, and 6 specimens remained false negative. The resolved data and recalculated sensitivity and specificity for the Toxo IgM microtiter assay are shown in Tables 14 and 15.

TABLE 14

Evaluation of Group 3 "Évolutive" Serum Specimens by
Toxo IgM Microtiter ELISA
After Resolution of Discordant Specimens

|  |  | IC IgM | |
|---|---|---|---|
|  |  | Pos | Neg |
| Toxo IgM (P29 + P35 + P66) Microtiter ELISA | Pos | 69 | 0 |
|  | Neg | 6 | 11 |
| Sensitivity: | 69/75 = 92.0% | | |

TABLE 15

Summary of Evaluation of Groups 1–4 Serum Specimens
by Toxo IgM Microtiter ELISA
After Resolution of Discordant Specimens

|  |  | Reference Test | |
|---|---|---|---|
|  |  | Pos | Neg |
| Toxo IgM (P29 + P30 + P35) Microtiter ELISA | Pos | 122 | 16 |
|  | Neg | 8 | 306 |
| Specificity: | 306/322 = 95.8% | | |
| Sensitivity: | 122/130 = 93.8% | | |

As can be seen from Tables 14 and 15 after resolution of discordant specimens, the Toxo IgM microtiter ELISA configured with the antigen cocktail is both a sensitive and specific assay for the detection of Toxoplasma-specific IgM as demonstrated by the overall high relative diagnostic specificity (95.0%) and sensitivity (93.8%) (Table 15) of the assay. The Toxo recombinant antigen cocktail comprised of the Toxo antigens P29, P35, and P66 is both necessary and sufficient to replace the tachyzoite for the detection of Toxoplasma-specific IgM indicative of a recent toxoplasmosis.

Furthermore, there are several advantages of this recombinant antigen cocktail over the tachyzoite antigen for use in detection of antibodies to IgM. First, the antigens are purified and the amount of each antigen loaded into the immunoassay can be accurately determined and standardized, e.g., protein concentration. This minimizes interlot differences commonly observed in kits manufactured with different tachyzoite antigen lots. Hence, different lots of kits manufactured with different antigen cocktail lots will be very consistent from lot to lot. Secondly, mouse monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Fourth, an IgM assay with the antigen cocktail will preferentially detect IgM antibodies produced in response to a recent infection. This can be seen in Tables 11 and 14 where specimens with high avidity IgG antibodies (indicative of a past or chronic infection) were negative for Toxo-specific IgM using the antigen cocktail in a microtiter ELISA. Finally, kits manufactured with the antigen cocktail are more stable during storage over time, and the performance of the assay using these antigens remains consistent over the shelf life of the assay. Kits manufactured with the tachyzoite antigen are not as stable, and their performance may vary over time.

Additionally, there are many advantages of using a cocktail over using a single antigen alone. For example, an immune response to infection varies by individual. Some individuals produce antibodies to P35 and not to P30 whereas some individuals produce antibodies to P30 and not to P35. Thus, the antigen cocktail of the present invention will detect both groups of individuals.

Also, immune responses vary with time. For example, one individual may produce antibodies against P35 first and then later produce antibodies to only P30. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is knownn from previous Western Blot experiments with tachyzoite proteins that the immune response to Toxoplasma is directed against several antigens. Once again, the present antigen cocktail will allow for the detection of all antibodies produced in response to these antigens.

EXAMPLE 13

Immunoblot Analysis of *T. gondii* Lysate Antigens

*T. gondii* lysate antigens were prepared from tachyzoites of the RH strain. The parasites were harvested from the peritoneal cavity of Swiss-Webster mice, as previously described (Prince et al., *Molecular Biochemical Parasitology* 43:97–106 (1990)). Reduced lysate was prepared by resuspension of tachyzoites in reducing sample buffer containing 0.5% sodium dodecyl sulfate (SDS), 25 mM Tris-HCl, pH 6.8, 170 mm β-mercaptoethanol, 8.4% glycerol, and 0.01% bromophenol blue. Non-recombinant CKS and rPRoxo-P35S proteins were prepared in reducing sample buffer containing 0.5% sodium dodecyl sulfate (SDS), 25 mM Tris-HCl, pH 6.8, 170 mM 2-mercaptoethanol, 8.4% glycerol, and 0.01% bromophenol blue. All samples were boiled for 5 minutes. Proteins were separated by SDS-PAGE in 10% slab gels and transferred to nitrocellulose membrane. For immunoblot analyses with human sera, the membranes with reduced rPToxo-P35S antigen or non-recombinant CKS antigen were incubated with pools of sera that had been diluted 1:100 in PBS-0.5% Tween 20 (PBS-T) containing 5% nonfat dry milk (Sambrook et al., 1989, Molecular Cloning. A Laboratory Manual, $2^{nd}$ ed. Cold Spring Harbor Laboratory Press, Cold Spring Harbor, N.Y.). The conjugate used was HRPO-conjugated goat anti-human IGG (Caltag Laboratories) at a previously determined optimal dilution of 1:3000 in PBS-T containing 3% bovine serum albumin (BSA). The substrate, 3,3'-diaminobenzidine tetrahydrochloride (Sigma Chemical Company, St. Louis, Mo.), was used at a final concentration of 0.1 mg/ml in PBS. Control immunoblots performed to test for the reactivity of the conjugates to either rPToxo35-P35S antigen or non-recombinant CKS antigen did not reveal any bands.

The results demonstrate that IgG antibodies from sera from humans with a *T. gondii* infection are reacting to a protein of the correct size to be the P35 fusion protein and not an irrelevant *E. coli* protein.

EXAMPLE 14

Preparation of Serum Samples and Performance of ELISA

Serum samples:

Sera were provided by the Toxoplasma Serology Laboratory of the Palo Alto Medical Foundation (Palo Alto, Calif.) and had been stored frozen for no longer than 2 years. The samples were from 141 pregnant women and were divided into three groups based on their serologic test results: Group I was composed of sera from 41 women with a serologic profile consistent with a recently acquired *T. gondi* infection (acute profile) and Group II of sera from 50 women with a serologic profile consistent with chronic infection. The serological tests used to classify these sera were: the Sabin Feldman dye test (DT), the double-sandwich-IgM ELISA (IgM ELISA), and the double-sandwich-IgA ELISA (IgA ELISA), and the AC/HS test (Lisenfeld et al., *Journal of Clinical Microbiology* 34:2526–30(1996); Lisenfeld et al., *Journal of Clinical Microbiology* 35:174–78 (1997); Wong et al., *Clinical Infectious Diseases* 18:853–62 (1994)). These tests comprise the "toxoplasma serological profile" (Lisenfeld et al., *Journal of Clinical Microbiology* 35:174–78 (1997)). Sera from women in Group I had high DT titers (from 1:256 to 1:32,000), positive IgM ELISA titers (from 2.3 to 9.7), positive IgA ELISA titers (from 1 to >28), and acute patterns in the AC/HS test. Sera from women in Group II had low DT (from 1:16 to 1:512), negative IgM ELISA titers (from 0 to 0.8), and chronic patterns in the AC/HS test. The classification of acute or chronic profile was based on the individual's clinical history as well as the combination of the results of the toxoplasma serological profile (Lisenfeld et al., *Journal of Clinical Microbiology* 35:174–78 (1997); Lisenfeld et al., *Journal of Clinical Microbiology* 35:174–78 (1997)). An additional group (Group III) was composed of sera from 50 women who were seronegative for *T. gondii* antibodies in the DT. A pool of serum samples from 5 seronegative individuals, each of whom was negative when their sera were tested undiluted in the DT, was used a negative control for immunoblots and the ELISA. Serum from a patient with a recently acquired toxoplasmic lymphadenopathy was used as a positive control on each ELISA plate.

ELISA:

Each well of a microtiter plate (Nunc, Roskilde, Denmark) was coated with 0.1 ml of a 10 μg/ml of rPToxo-P35S antigen was determined to be the optimal concentration with which to coat the wells of the ELISA plates. Consequently, the control non-recombinant CKS antigen preparation was also used at 10 μg/ml to coat plates. After incubation at 4° C. overnight, the plates were washed three times with PBS-T and post-coated with 200 μl per well of 3% BSA in PBS-T at 37° C. for 2 h. The plates were then washed and 100 μl of test or control serum diluted 1:50 in 1% BSA in PBS-T were applied to each well with rPToxo-P35S antigen preparation, non-recombinant CKS antigen preparation or without antigen. Plates were incubated at 37° C. for 1 h, washed and then 100 μl of HRPO-conjugated goat anti-human IgG at a dilution of 1:1000 was added to each well. The plates were incubated at 37° C. for 1 h, washed and then 100 μl of 0.03% O-phenylenediamine in $H_2O_2$ were added to each well. The optical density values were measured with an automatic ELISA reader (Dynatech Laboratories, Chantilly, Va.) after 15 min. incubation at room temperature. Each sample was run in duplicate wells. Results were determined for each patient by taking the mean value of the absorbency readings of duplicate wells.

Figure 15:
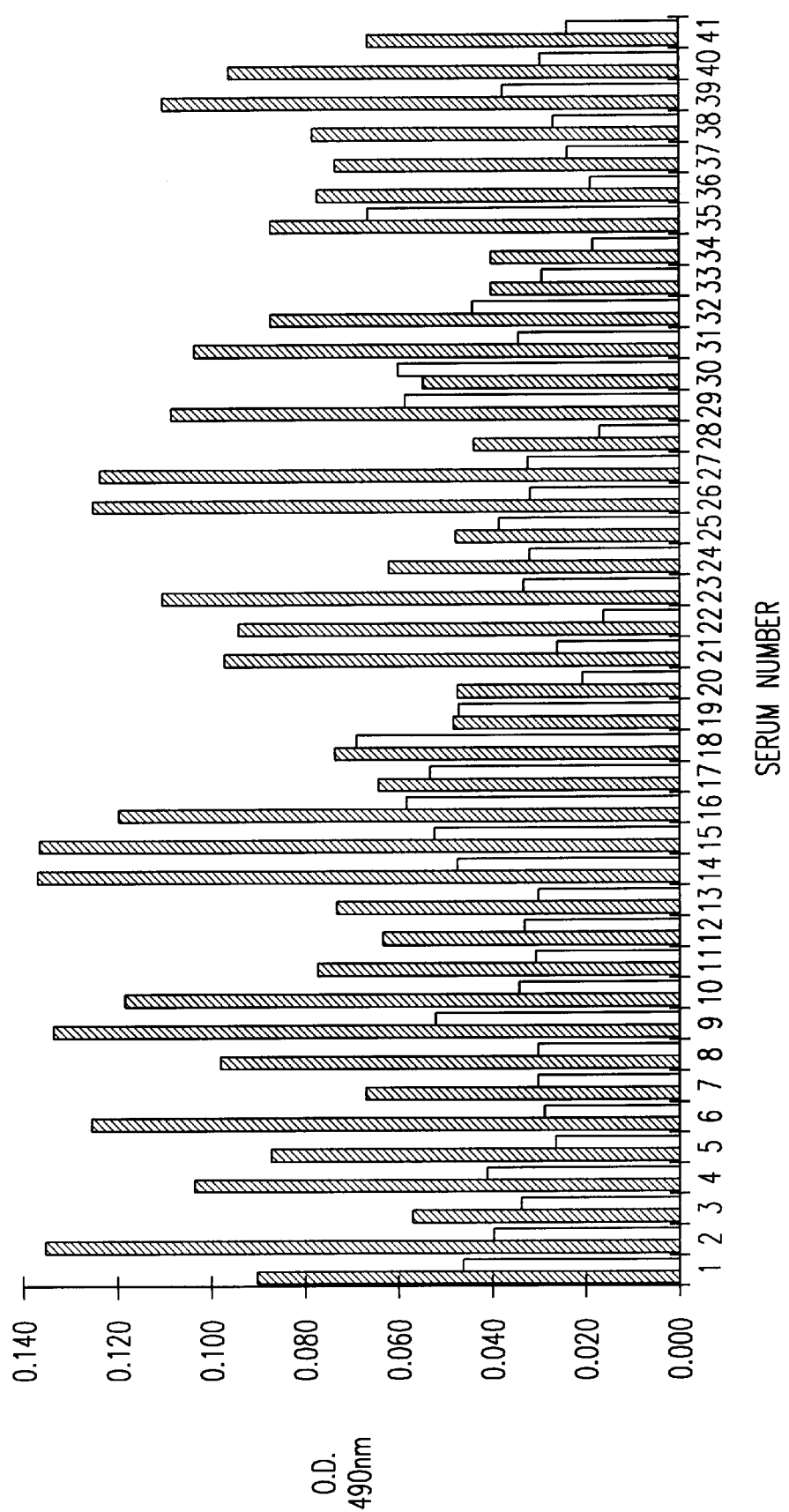
FIG. 15 illustrates ELISA readings in 41 Group I sera. Dark columns are OD 450 readings with rpToxo-P35S preparation and light columns are readings with the CKS preparation.

Of the 41 sera from Group I, 40 (97.6%) had absorbency readings higher in the rPToxo-P35S ELISA than in the control ELISA and 1 had absorbency readings higher in the control ELISA than in the rpToxo-P35S ELISA (FIG. 15). In contrast, of the 50 sera from Group II, 30 (60%) had readings in the control ELISA that were equal to or higher than in the rpToxo-P35S ELISA, and the remaining 20

Figure 16:
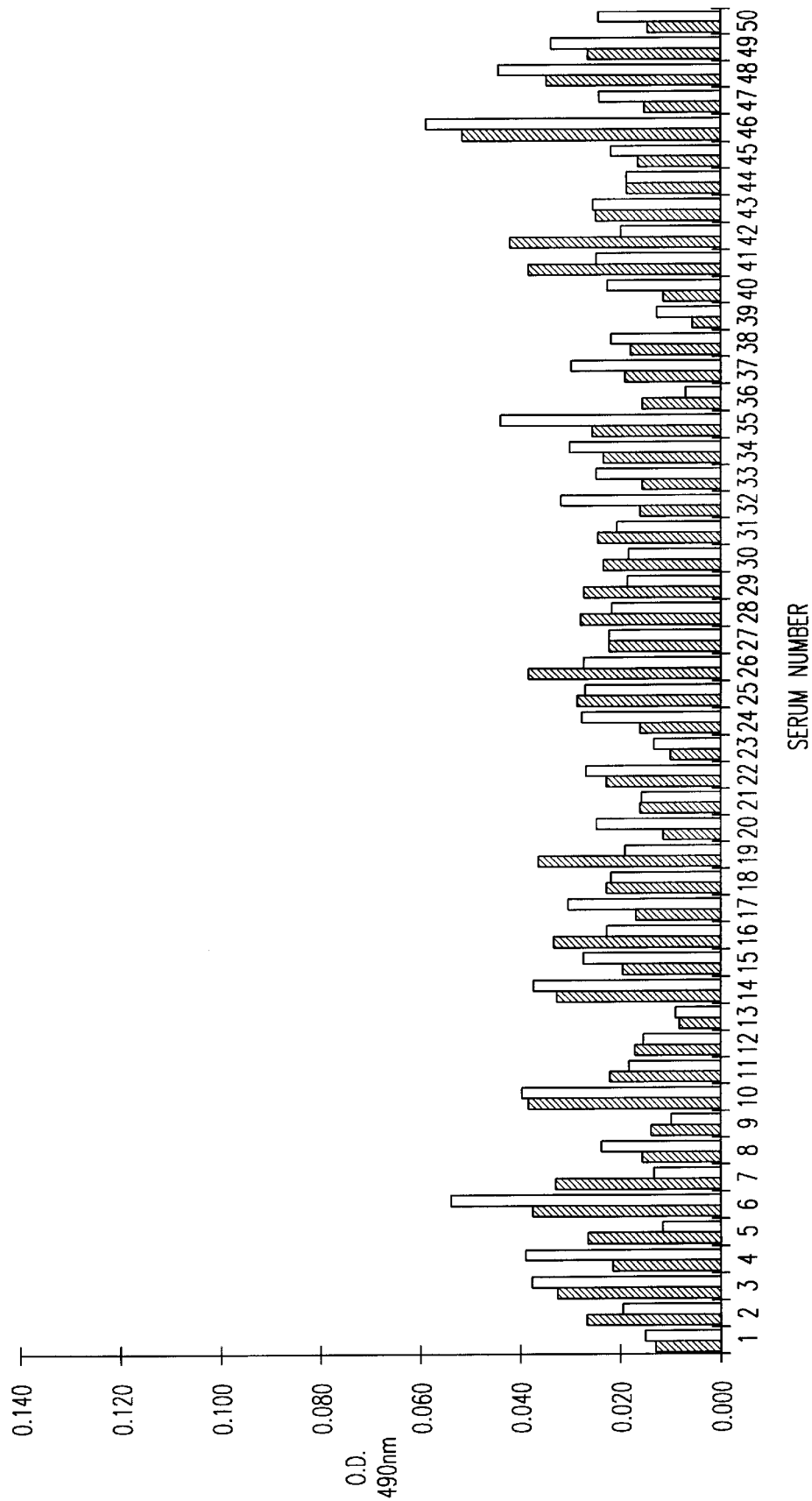
FIG. 16 represents ELISA readings in 50 Group II sera. Dark columns are readings with rpToxo-P35S preparation, and light columns are readings with the CKS preparation.

(40%) had absorbency readings in the rpToxo-P35S ELISA that were only slightly higher than the readings noted in the control ELISA (FIG. 16). The mean of the Group I seara (0.0513+/−0.0045 standard error) was significantly (p=0.0001) higher than the mean of the Group II sera (0.0031+/−0.0008 standard error).

Figure 17:
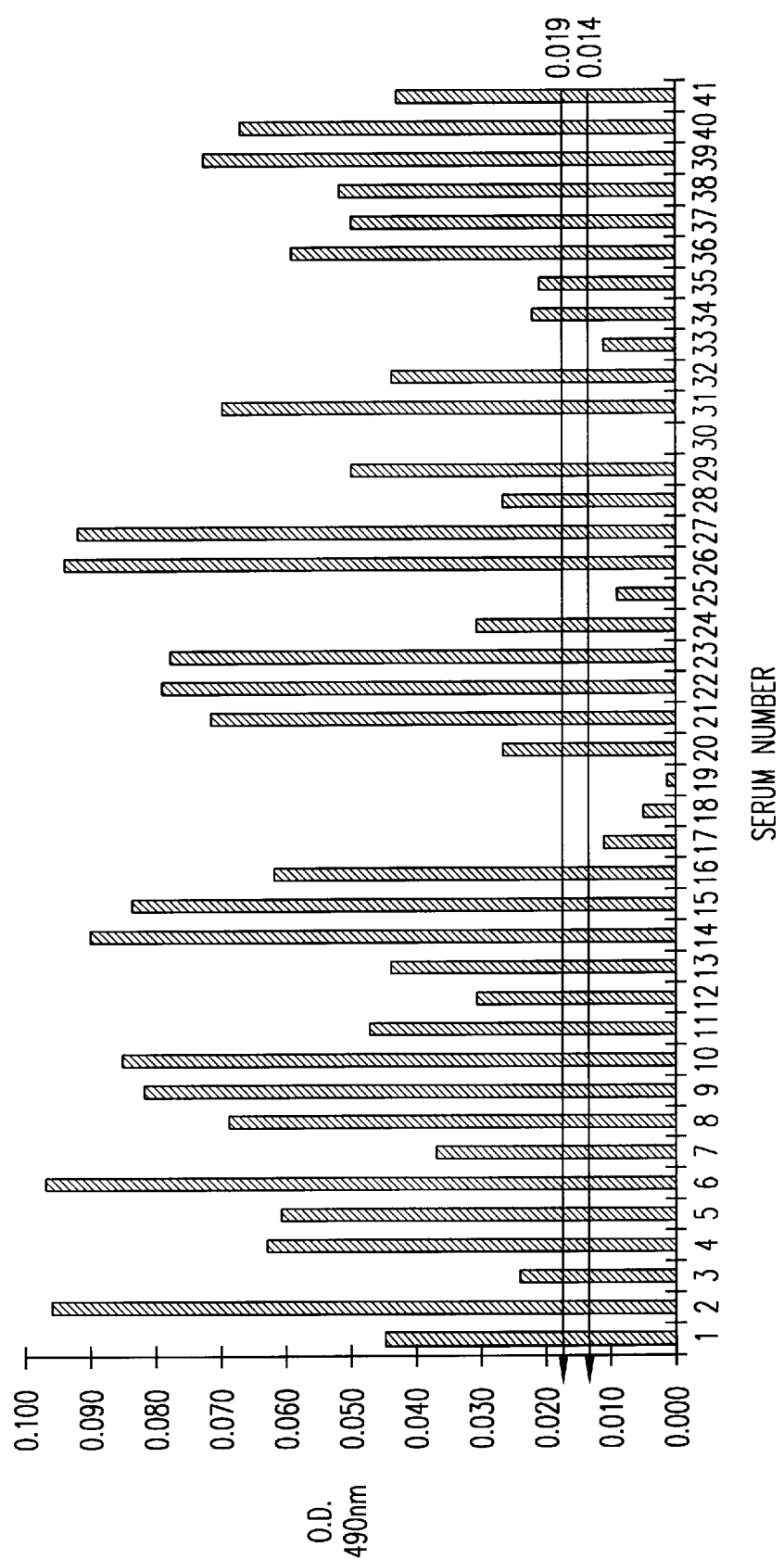
FIG. 17 illustrates rpToxo-P35S ELISA readings of 41 Group I sera after subtraction of the readings of the same sera in the control ELISA. The horizonal lines represent the cut-off values of 0.014 (mean+2 SD) and 0.019 (mean+3 SD) obtained as described in the Examples.
Figure 18:
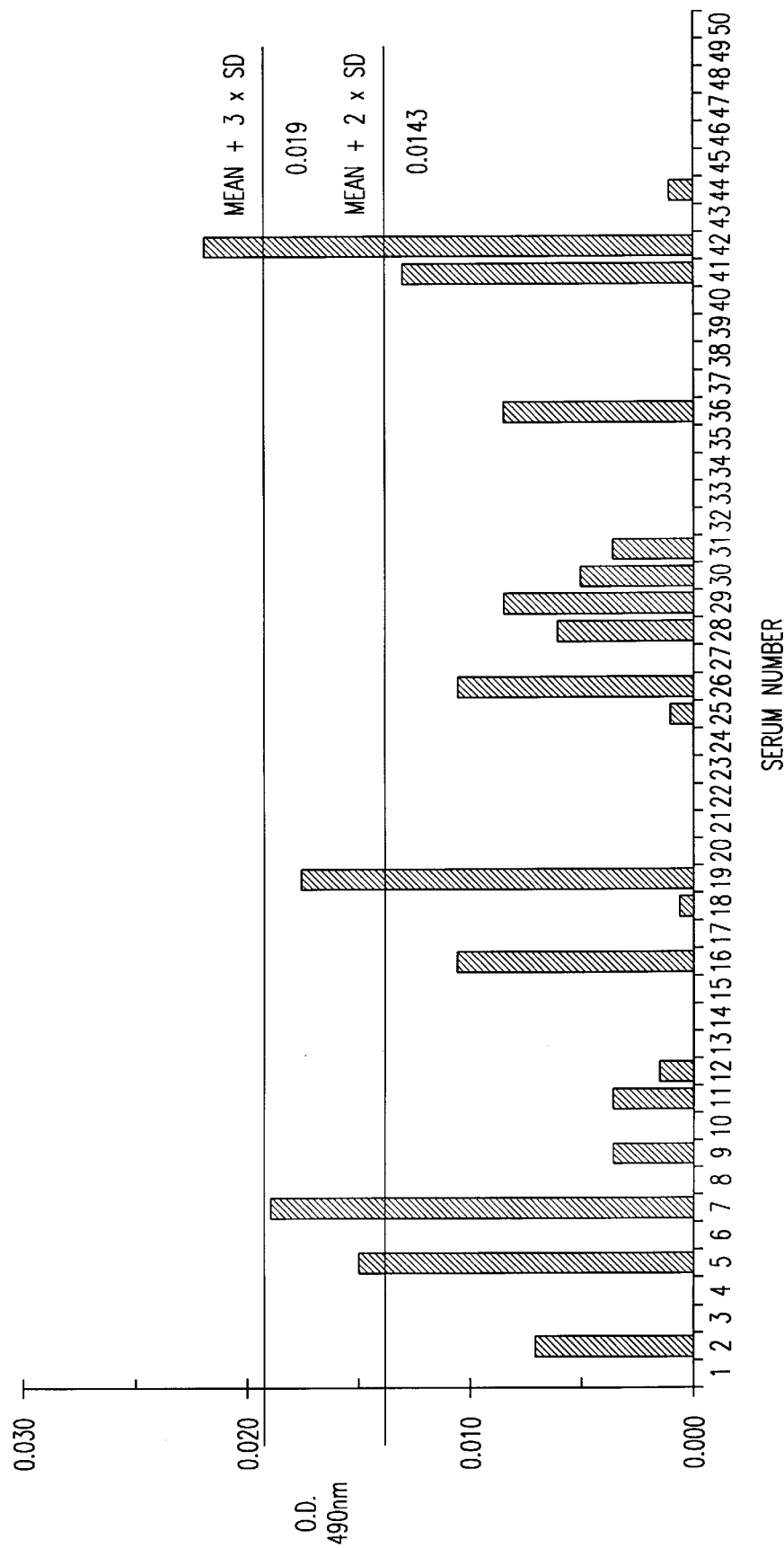
FIG. 18 represents rpToxo-P35S ELISA readings of 50 Group I sera after subtraction of the readings of the same seria in the control ELISA. The horizontal lines represent the cut-off values as in FIG. 17.

With respect to determining whether the reactivity of IgG antibodies with rpToxo-P35S could be used to differentiate Group I from Group II sera, it was observed that 35 (85.3%) of 41 Group I sera had normalized readings higher than the cut-off value (FIG. 17). In contrast, only 4 (8%) of the 50 Group II sera had normalized readings higher than the cut-off value (FIG. 18). When compared with interpretations made based on the toxoplasma serological profile results, the sensitivity of the rpToxo-P35S ELISA for recently acquired infection was 85.3% and the specificity was 92%. Using a cut-off value (0.019) based on the mean plus 3 standard deviations of the Group II readings, 35 (85.3%) of 41 Group I sera (FIG. 17) and only 1 (2%) of the 50 Group II sera (FIG. 18) had normalized readings higher than the cut-off value.

The above results demonstrate that the P35 antigen in the IgG ELISA can be used to distinguish between patient sera obtained from individuals in the acute stage of infection versus individuals in the chronic stage of infection. In particular, it was determined that the patients of Group I has an acute infection and those of Group II had a chronic infection. Thus, P35 may be used to distinguish between acute and chronic Toxoplasmosis.

```
                    FIG. 9  pToxo-P30

10          20          30          40
   1234567890  1234567890  1234567890  1234567890

GAATTAATTC  CCATTAATGT  GAGTTAGCTC  ACTCATTAGG       40

CACCCCAGGC  TTTACACTTT  ATGTTCCGGC  TCGTATTTTG       80

TGTGGAATTG  TGAGCGGATA  ACAATTGGGC  ATCCAGTAAG      120

GAGGTTTAAA  TGAGTTTTGT  GGTCATTATT  CCCGCGCGCT      160
            M  etSerPheVa  lValIleIle  ProAlaArgT

ACGCGACGTC  GCGTCTGCCC  GGTAAACCAT  TGGTTGATAT      200
   yrAlaThrSe  rArgLeuPro  GlyLysProL  euValAspIl

TAACGGCAAA  CCCATGATTG  TTCATGTTCT  TGAACGCGCG      240
   eAsnGlyLys  ProMetIleV  alHisValLe  uGluArgAla

CGTGAATCAG  GTGCCGAGCG  CATCATCGTG  GCAACCGATC      280
   ArgGluSerG  lyAlaGluAr  gIleIleVal  AlaThrAspH

ATGAGGATGT  TGCCCGCGCC  GTTGAAGCCG  CTGGCGGTGA      320
   isGluAspVa  lAlaArgAla  ValGluAlaA  laGlyGlyGl

AGTATGTATG  ACGCGCGCCG  ATCATCAGTC  AGGAACAGAA      360
   uValCysMet  ThrArgAlaA  spHisGlnSe  rGlyThrGlu

CGTCTGGCGG  AAGTTGTCGA  AAAATGCGCA  TTCAGCGACG      400
   ArgLeuAlaG  luValValGl  uLysCysAla  PheSerAspA

ACACGGTGAT  CGTTAATGTG  CAGGGTGATG  AACCGATGAT      440
   spThrValIl  eValAsnVal  GlnGlyAspG  luProMetIl

CCCTGCGACA  ATCATTCGTC  AGGTTGCTGA  TAACCTCGCT      480
   eProAlaThr  IleIleArgG  lnValAlaAs  pAsnLeuAla

CAGCGTCAGG  TGGGTATGAC  GACTCTGGCG  GTGCCAATCC      520
   GlnArgGlnV  alGlyMetTh  rThrLeuAla  ValProIleH
```

What is claimed is:

1. A method for distinguishing between acute and chronic toxoplasmosis in a patient suspected of having either said acute or chronic toxoplasmosis comprising the steps of: a) contacting a test sample, from said patient, with a composition consisting of amino acids 172–306 of SEQ ID NO:54 and optionally, an amino acid sequence of a fusion protein, wherein said amino acids 172–306 of SEQ ID NO:54 are derived from isolated *Toxoplasma gondii* antigen P35; and b) detecting the presence of IgG antibodies, presence of said IgG antibodies indicating acute toxoplasmosis in said patient and lack of said IgG antibodies indicating chronic toxoplasmosis in said patient.

2. The method of claim 1, wherein said amino acids 172–306 of SEQ ID NO:54 are encoded by nucleic acids 643–1047 of SEQ ID NO:45.

3. The method of claim 1, wherein said fusion protein is CMP-KDO synthetase (CKS)—.

* * * * *